(12) United States Patent
Shalev

(10) Patent No.: US 7,640,062 B2
(45) Date of Patent: Dec. 29, 2009

(54) METHODS AND SYSTEMS FOR MANAGEMENT OF ALZHEIMER'S DISEASE

(75) Inventor: Alon Shalev, Ra'anana (IL)

(73) Assignee: Brainsgate Ltd., Caesarea (IL)

( * ) Notice: Subject to any disclaimer, the term of this patent is extended or adjusted under 35 U.S.C. 154(b) by 492 days.

(21) Appl. No.: 10/518,322

(22) Filed: Jul. 8, 2005

(65) Prior Publication Data

US 2006/0020299 A1 Jan. 26, 2006

Related U.S. Application Data

(63) Continuation-in-part of application No. 10/258,714, filed on Jan. 22, 2003, now Pat. No. 7,120,489, which is a continuation-in-part of application No. 10/294,310, filed as application No. PCT/IL01/00402 on May 7, 2001, now Pat. No. 7,146,209.

(60) Provisional application No. 60/388,931, filed on Jun. 14, 2002, provisional application No. 60/400,167, filed on Jul. 31, 2002, provisional application No. 60/364,451, filed on Mar. 15, 2002, provisional application No. 60/203,172, filed on May 8, 2000.

(51) Int. Cl.
*A61N 1/08* (2006.01)
(52) U.S. Cl. .................... 607/45; 607/1; 607/2
(58) Field of Classification Search ............ 607/1, 607/2, 45

See application file for complete search history.

(56) References Cited

U.S. PATENT DOCUMENTS

| | | | |
|---|---|---|---|
| 4,666,829 A | 5/1987 | Glenner et al. |
| 4,866,042 A | 9/1989 | Neuwelt |
| 4,874,694 A | 10/1989 | Gandy et al. |
| 4,979,511 A | 12/1990 | Terry, Jr. |
| 5,011,472 A | 4/1991 | Aebischer et al. |
| 5,031,618 A | 7/1991 | Mullett |
| 5,059,415 A | 10/1991 | Neuwelt |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke |
| 5,205,285 A | 4/1993 | Baker, Jr. |
| 5,215,086 A | 6/1993 | Terry, Jr. |
| 5,215,089 A | 6/1993 | Baker, Jr. |
| 5,222,494 A | 6/1993 | Baker, Jr. |

(Continued)

FOREIGN PATENT DOCUMENTS

EP 1559369 8/2005

(Continued)

OTHER PUBLICATIONS

Tuhrim, S., 2002. "Management of Stroke and Transient Ischemic Attack". The Mount Sinai Journal of Medicine 69: 121-130.

(Continued)

*Primary Examiner*—Carl H Layno
*Assistant Examiner*—Deborah Malamud
(74) *Attorney, Agent, or Firm*—RatnerPrestia

(57) ABSTRACT

A method is provided for treating Alzheimer's disease (AD). The method includes stimulating a sphenopalatine ganglion (SPG) of a subject so that the concentration of a substance in a brain of the subject changes.

7 Claims, 12 Drawing Sheets

U.S. PATENT DOCUMENTS

| | | |
|---|---|---|
| 5,223,254 A | 6/1993 | Paradiso et al. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke |
| 5,268,164 A | 12/1993 | Kozarich et al. |
| 5,269,303 A | 12/1993 | Wernicke et al. |
| 5,299,569 A | 4/1994 | Wernicke |
| 5,304,206 A | 4/1994 | Baker, Jr. et al. |
| 5,304,632 A | 4/1994 | Vaudry et al. |
| 5,330,515 A | 7/1994 | Rutecki et al. |
| 5,335,657 A | 8/1994 | Terry, Jr. |
| 5,351,394 A | 10/1994 | Weinberg |
| 5,540,730 A | 7/1996 | Terry, Jr. |
| 5,540,734 A | 7/1996 | Zabara |
| 5,571,150 A | 11/1996 | Wernicke |
| 5,639,853 A | 6/1997 | Paradiso et al. |
| 5,707,400 A | 1/1998 | Terry, Jr. |
| 5,756,071 A | 5/1998 | Mattern et al. |
| 5,792,100 A * | 8/1998 | Shantha ............ 604/509 |
| 5,830,670 A | 11/1998 | De la Monte et al. |
| 5,833,988 A | 11/1998 | Friden |
| 5,849,600 A | 12/1998 | Nixon et al. |
| 5,928,272 A | 7/1999 | Adkins et al. |
| 5,938,689 A | 8/1999 | Fischell et al. |
| 5,938,690 A | 8/1999 | Law et al. |
| 5,981,194 A | 11/1999 | Jefferies et al. |
| 5,985,581 A | 11/1999 | Nixon et al. |
| 6,001,331 A | 12/1999 | Caprathe et al. |
| 6,005,004 A | 12/1999 | Katz et al. |
| 6,006,124 A | 12/1999 | Fischell et al. |
| 6,016,449 A | 1/2000 | Fischell et al. |
| 6,017,963 A | 1/2000 | Alfonso et al. |
| 6,061,593 A | 5/2000 | Fischell et al. |
| 6,066,163 A | 5/2000 | John |
| 6,071,705 A | 6/2000 | Wands et al. |
| 6,087,118 A | 7/2000 | Aronson et al. |
| 6,114,175 A | 9/2000 | Klunk et al. |
| 6,117,454 A | 9/2000 | Kreuter et al. |
| 6,128,538 A | 10/2000 | Fischell et al. |
| 6,130,048 A | 10/2000 | Nixon |
| 6,132,977 A | 10/2000 | Thompson et al. |
| 6,134,474 A | 10/2000 | Fischell et al. |
| 6,161,045 A | 12/2000 | Fischell et al. |
| 6,200,768 B1 | 3/2001 | Mandelkow et al. |
| 6,210,895 B1 | 4/2001 | Schipper et al. |
| 6,211,235 B1 | 4/2001 | Wu et al. |
| 6,230,049 B1 | 5/2001 | Fischell et al. |
| 6,232,326 B1 | 5/2001 | Nelson |
| 6,277,841 B1 | 8/2001 | Rajagopalan et al. |
| 6,287,793 B1 | 9/2001 | Schenk et al. |
| 6,322,494 B1 | 11/2001 | Bullivant et al. |
| 6,647,296 B2 | 11/2001 | Fischell et al. |
| 6,325,475 B1 | 12/2001 | Hayes et al. |
| 6,329,531 B1 | 12/2001 | Turner et al. |
| 6,338,715 B1 | 1/2002 | Hayes et al. |
| 6,353,754 B1 | 3/2002 | Fischell et al. |
| 6,354,299 B1 | 3/2002 | Fischell et al. |
| 6,358,681 B2 | 3/2002 | Ginsberg et al. |
| 6,360,122 B1 | 3/2002 | Fischell et al. |
| 6,410,046 B1 | 6/2002 | Lerner |
| 6,427,086 B1 | 7/2002 | Fischell et al. |
| 6,597,953 B2 | 7/2002 | Boling |
| 6,432,986 B2 | 8/2002 | Levin |
| 6,459,936 B2 | 10/2002 | Fischell et al. |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 | 2/2003 | Ansarinia |
| 6,529,774 B1 | 3/2003 | Greene |
| 6,531,454 B1 | 3/2003 | Leary et al. |
| 6,587,719 B1 | 7/2003 | Barrett et al. |
| 6,587,724 B2 | 7/2003 | Mann |
| 6,591,137 B1 | 7/2003 | Fischell et al. |
| 6,591,138 B1 | 7/2003 | Fischell et al. |
| 6,597,954 B1 | 7/2003 | Pless et al. |
| 6,606,521 B2 | 8/2003 | Paspa et al. |
| 6,609,025 B2 | 8/2003 | Barrett et al. |
| 6,609,032 B1 | 8/2003 | Woods et al. |
| 6,609,956 B2 | 8/2003 | Margaria |
| 6,618,623 B1 | 9/2003 | Pless et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,662,035 B2 | 12/2003 | Sochor |
| 6,678,553 B2 | 1/2004 | Lerner et al. |
| 6,735,474 B1 | 5/2004 | Loeb et al. |
| 6,735,475 B1 | 5/2004 | Whitehurst et al. |
| 6,905,827 B2 | 6/2004 | Wohlgemuth et al. |
| 6,788,975 B1 | 9/2004 | Whitehurst et al. |
| 6,810,285 B2 | 10/2004 | Pless et al. |
| 6,811,788 B2 | 11/2004 | Yu |
| 6,853,858 B2 | 2/2005 | Shalev |
| 7,146,209 B2 | 12/2006 | Gross et al. |
| 2001/0018191 A1 | 8/2001 | Mercken et al. |
| 2001/0020097 A1 | 9/2001 | Audia et al. |
| 2001/0027309 A1 | 10/2001 | Elsberry |
| 2001/0044126 A1 | 11/2001 | Holtzman et al. |
| 2001/0047014 A1 | 11/2001 | Alanine et al. |
| 2001/0051633 A1 | 12/2001 | Bigge et al. |
| 2002/0002270 A1 | 1/2002 | Zinkowski et al. |
| 2002/0006627 A1 | 1/2002 | Reitz et al. |
| 2002/0009445 A1 | 1/2002 | Du et al. |
| 2002/0019016 A1 | 2/2002 | Vanmechelen et al. |
| 2002/0019412 A1 | 2/2002 | Andersen et al. |
| 2002/0019519 A1 | 2/2002 | Bingham et al. |
| 2002/0022242 A1 | 2/2002 | Small et al. |
| 2002/0022593 A1 | 2/2002 | Yue |
| 2002/0022621 A1 | 2/2002 | Chaturvedula et al. |
| 2002/0022650 A1 | 2/2002 | Posmantur et al. |
| 2002/0025955 A1 | 2/2002 | Han et al. |
| 2002/0026652 A1 | 2/2002 | Allen et al. |
| 2002/0028462 A1 | 3/2002 | Tanzi et al. |
| 2002/0028834 A1 | 3/2002 | Villalobos et al. |
| 2002/0035145 A1 | 3/2002 | Tsai et al. |
| 2002/0042121 A1 | 4/2002 | Riesner et al. |
| 2002/0044919 A1 | 4/2002 | Yu |
| 2002/0052311 A1 | 5/2002 | Solomon et al. |
| 2002/0055501 A1 | 5/2002 | Olson et al. |
| 2002/0066959 A1 | 6/2002 | Joshi |
| 2002/0068080 A1 | 6/2002 | Lerner |
| 2002/0082583 A1 | 6/2002 | Lerner |
| 2002/0099412 A1 | 7/2002 | Fischell et al. |
| 2002/0099417 A1 | 7/2002 | Naritoku et al. |
| 2002/0123678 A1 | 9/2002 | Lerner et al. |
| 2002/0133841 A1 | 9/2002 | Leviten |
| 2002/0169307 A1 | 11/2002 | Klein |
| 2003/0005477 A1 | 1/2003 | Leviten |
| 2003/0013136 A1 | 1/2003 | Balser et al. |
| 2003/0014772 A1 | 1/2003 | Allen |
| 2003/0018988 A1 | 1/2003 | Allen et al. |
| 2003/0018989 A1 | 1/2003 | Brennan et al. |
| 2003/0036781 A1 | 2/2003 | Nuttin et al. |
| 2003/0051268 A1 | 3/2003 | Allen |
| 2003/0056238 A1 | 3/2003 | Wisotzkey |
| 2003/0073917 A1 | 4/2003 | Echauz et al. |
| 2003/0074033 A1 | 4/2003 | Pless et al. |
| 2003/0106083 A1 | 6/2003 | Allen |
| 2003/0131367 A1 | 7/2003 | Guenther et al. |
| 2003/0144711 A1 | 7/2003 | Pless et al. |
| 2003/0149457 A1 | 8/2003 | Tcheng et al. |

| | | | |
|---|---|---|---|
| 2003/0166099 | A1 | 9/2003 | Sabbadini et al. |
| 2003/0166279 | A1 | 9/2003 | Sabbadini et al. |
| 2003/0172390 | A1 | 9/2003 | Wisotzkey et al. |
| 2003/0176892 | A1 | 9/2003 | Shalev |
| 2003/0176898 | A1 | 9/2003 | Gross et al. |
| 2003/0190601 | A1 | 10/2003 | Sabbadini et al. |
| 2003/0190683 | A1 | 10/2003 | Sabbadini et al. |
| 2003/0190749 | A1 | 10/2003 | Surber et al. |
| 2003/0191426 | A1 | 10/2003 | Lerner et al. |
| 2003/0194714 | A1 | 10/2003 | Sabbadini et al. |
| 2003/0195588 | A1 | 10/2003 | Fischell et al. |
| 2003/0195602 | A1 | 10/2003 | Boling |
| 2003/0198995 | A1 | 10/2003 | Sabbadini et al. |
| 2003/0198996 | A1 | 10/2003 | Surber et al. |
| 2003/0199088 | A1 | 10/2003 | Sabbadini et al. |
| 2003/0199089 | A1 | 10/2003 | Surber et al. |
| 2003/0202937 | A1 | 10/2003 | Sabbadini et al. |
| 2003/0203411 | A1 | 10/2003 | Sabbadini et al. |
| 2003/0203481 | A1 | 10/2003 | Surber et al. |
| 2003/0207833 | A1 | 11/2003 | Berkley et al. |
| 2003/0211086 | A1 | 11/2003 | Berkley et al. |
| 2003/0211599 | A1 | 11/2003 | Sabbadini et al. |
| 2003/0219408 | A1 | 11/2003 | Sabbadini et al. |
| 2003/0219888 | A1 | 11/2003 | Segall et al. |
| 2003/0224369 | A1 | 12/2003 | Surber et al. |
| 2003/0224444 | A1 | 12/2003 | Sabbadini et al. |
| 2003/0232335 | A1 | 12/2003 | Surber et al. |
| 2004/0015068 | A1 | 1/2004 | Shalev et al. |
| 2004/0033491 | A1 | 2/2004 | Alsobrook et al. |
| 2004/0054297 | A1 | 3/2004 | Wingeier et al. |
| 2004/0133248 | A1 | 7/2004 | Frei et al. |
| 2004/0136951 | A1 | 7/2004 | Ni et al. |
| 2004/0153129 | A1 | 8/2004 | Pless et al. |
| 2004/0210269 | A1 | 10/2004 | Shalev et al. |
| 2004/0220644 | A1 | 11/2004 | Shalev et al. |
| 2005/0020519 | A1 | 1/2005 | Albiston et al. |
| 2005/0054939 | A1 | 3/2005 | Ben-Ari et al. |
| 2005/0074506 | A1 | 4/2005 | Natan et al. |
| 2005/0112090 | A9 | 5/2005 | Ni et al. |
| 2005/0118187 | A1 | 6/2005 | Yu |
| 2005/0137646 | A1 | 6/2005 | Wallace et al. |
| 2005/0137647 | A1 | 6/2005 | Wallace et al. |
| 2005/0159790 | A1 | 7/2005 | Shalev et al. |
| 2005/0177514 | A1 | 8/2005 | Sasselli |

FOREIGN PATENT DOCUMENTS

| | | |
|---|---|---|
| JP | 08-229141 | 9/1996 |
| WO | WO 97/18855 | 5/1997 |
| WO | WO 99/03473 | 1/1999 |
| WO | WO 00/44432 | 8/2000 |
| WO | WO 00/73343 | 12/2000 |
| WO | WO 01/00402 | 1/2001 |
| WO | WO 01/43733 | 6/2001 |
| WO | WO 01/85094 | 11/2001 |
| WO | WO 01/97905 | 12/2001 |
| WO | WO 02/094191 | 11/2002 |
| WO | WO 2004/010923 | 2/2004 |
| WO | WO 2004/043217 | 5/2004 |
| WO | WO 2004/043218 | 5/2004 |
| WO | WO 2004/043334 | 5/2004 |
| WO | WO 2004/044947 | 5/2004 |
| WO | WO 2004/045242 | 5/2004 |
| WO | WO-2004/064918 A1 | 8/2004 |

OTHER PUBLICATIONS

Cooke, B., and Ernst, E., 2000. "Aromatherapy: a systematic review". British Journal of General Practice 50: 493-496.

Zatorre, et al., 1992. "Functional localization and lateralization of human olfactory cortex". Nature 360: 339-340.

Henkin, et al., 2000. "Taste and Smell Phantoms Revealed by Brain Functional MRI (fMRI)". Journal of Computer Assisted Tomography 24: 106-123.

Fox, P., and Raichle, M., 1984. "Stimulus Rate Dependence of Regional Cerebral Blood Flow in Human Striate Cortex, Demonstrated by Positron Emission Tomography". Journal of Neurophysiology 51: 1109-1120.

Walker, et al., 2001. "Human Responses to Propionic Acid. II. Quantification of Breathing Responses and their Relationship to Perception". Chemical Senses 26: 351-358.

Encarta World Dictionary (2003) Online. http://encarta.nnsn.com/encnet/features/dictionary/DictionaryResults.aspx?refid=1861589580.

Suzuki, N. et al., "Effect on Cortical Blood Flow of Electrical Stimulation of Trigeminal Cerebrovascular Nerve Fibers in the Rat", Acta Physiol. Scand., 138, 307-315, 1990.

Major A. Silver, W., "Odorants presented to the rat nasal cavity increase cortical blood flow, "Chem. Senses, 24, 665-669 (1999).

Fusco BM, Fiore G, Gallo F, Martelletti P, Giacovazzo M, "Capsaicin-senstive' sensory neurons in cluster headache: pathophysiological aspects and therapeutic indications," Headache, 34, 132-137 (1994).

Lambert GA, Bogduk N, Goadsby PJ, Duckworth JW, Lance JW, "Decreased cartoid arterial resistance in cats in response to trigeminal stimulation," Journal of Nerosurgery, 61, 307-315.

Silver WL, "Neural and pharmacological basis for nasal irritation," in tucker WG, Leaderer BP, Molhave L. Cain WS (eds), Sources of Indoor Air Contaminants, Ann. NY Acad. Sci., 641, 152-163 (1992).

J.M. Gallo, et al., "The Effect of P-glycoprotein on Paclitaxel Brain Tumor Distributuion in Mice", Cancer Research 63, 5114-5117, Aug. 2003.

Brainimir I. Sikic, et al., "Modulation and prevention of multidrug resistance by inihibitors of P-glycoprotein", Cancer Chemother Pharmocol (1997), 40 (Suppl): S13-S19.

Fu Yung-Hui, et al., "Improved bioavailability of orally administered drugs by Chinese herbal enhancers through modulation of P-glycoprotein", ASHP 39$^{th}$ Midyear Clinical Meeting and Exhibits, Dec. 5-9, 2004.

U.S. Appl. No. 10/428,743, Todd K. Whitehurst.

U.S. Appl. No. 60/265,008, filed Jan. 30, 2001.

U.S. Appl. No. 60/383,317, filed May 24, 2002.

European Search Report, dated Dec. 13, 2006 for Application No. EP 06 01 7239.

Hotta H et al., in an article entitled, "Effects of stimulating the nucleus basalis of Meynert on blood flow and delayed neuronal death following transient ischemia in rat cerebral cortes," Jap J Phys 52:383-393 (2002).

Segher O et al., in an article entitled, "Spinal cord stimulation reducing infract volume in model of focal cerebral ischemia in rats," J Neurosurg 99(1):131-137 (2003).

Goadsby PJ et al., "Effect of stimulation of trigeminal ganglion on regional cerebral blood flow in cats," Am J Physiol 253:R270-R274 (1987).

Matsui T et al., in an article entitled, "The effects of cervical spinal cord stimulation (cSCS) on experimental stroke," Pacing Clin Electrophysiol 12(4 Pt 2):726-32 (1989).

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989).

Walters BB et al., "Cerebrovascular projections from the sphenopalatine and otic ganglia to the middle cerebral artery of the cat," Stroke 17:488-494 (1986).

Branston NM, "The physiology of the cerebrovascular parasympathetic innervation," British Journal of Neurosurgery 9:319-329 (1995).

Branston NM et al., "Contribution of cerebrovascular parasympathetic and sensory innervation to the short-term control of blood flow in rat cerebral cortex," J Cereb Blood Flow Metab 15(3) 525-31 (1995).

Sun Y et al., "Neuronal nitric oxide synthase and ischemia-induced neurogenesis," J Cereb Blood Flow Metab 25(4):485-92 (2005).

Zhang F et al., "Nitric oxide donors increase blood flow and reduce brain damage in focal ischemia: evidence that nitric oxide is beneficial in the early stages of cerebral ischemia," J Cereb Blood Flow Metab 14(2):217-26 (1994).

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998).

Jolliet-Riant P, Tillement JP, "Drug transfer across the blood-brain barrier and improvement of brain delivery," Fundam. Clin. Pharmacol., 13, 16-25 (1999).

Syelaz J, Hara H, Pinard E, Mraovitch S, MacKenzie ET, Edvinsson L, "Effects of stimulation of the sphenopalatine ganglion on cortical blood flow in the rat," Journal of Cerebral Blood Flow and Metabolism, 8, 875-878 (1988).

Toda N. et al., "Cerebral vasodilation induced by stimulation of the pterygopalatine ganglion and greater petrosal nerve in anesthetized monkeys," Neuroscience 96(2):393-398 (2000).

Varghese et al., "Endoscopic transnasal neurolytic sphenopalatine ganglion block for head and neck cancer pain," J Laryngol Otol 115(5):385-7 (2001).

Roman GC, "Cholinergic dysfunction in vascular dementia," Curr Psychiatry Rep 7(1):18-26 (2005).

Van Gijn J et al., "Subarachnoid haemorrhage: diagnosis, causes and management," Brain 124.249-278 (2001).

Davis SM et al., "Advances in penumbra imaging with MR," Cerebrovasc Dis 17 Suppl 3:23-7 (2004).

Zausinger VS et al., "Neurological impairment in rats after transient middle cerebral artery occlusion: a comparative study under various treatment paradigms," Brain Research 863(1-2):94-105 (2000).

Phan TG et al., "Salvaging the ischaemic penumbra: more than just reperfusion?" Clin Exp Pharmacol Physiol 29(1-2):1-10 (2002).

Zhang ZG et el., "VEGF enhances angiogenesis and promotes blood-brain barrier leakage in the ischemic brain," J Clin Invest 106:829-838 (2000).

Kawamata T et al., "Intracisternal basic fibroblast growth factor (bFGF) enhances behavioral recovery following focal cerebral infarction in the rat," J Cereb Blood Flow Metab 16:542-547 (1996).

Ziche M et al., "Nitric oxide and angiogenesis," J Neurooncol 50:139-148 (2000).

Zhang R et al., "A nitric oxide donor induces neurogenesis and reduces functional deficits after stroke in rats," Ann Neurol 50:602-611 (2001).

de la Torre JC, "Vascular basis of Alzheimer's pathogenesis," Ann NY Acad Sci 977:196-215 (2002).

Hunter AJ et al., "To what extent have functional studies of ischemia in animals been useful in the assessment of potential neuroprotective agents?" Trends Pharmacol Sci 19:59-66 (1998).

Kanner AA et al., "Serum S100beta: a noninvasive marker of blood-brain barrier function and brain lesions," Cancer 97(11):2806-13 (2003).

Lee,JFL, "Nitric oxide and the cerebral vascular function," J Biomed Sci 7:16-26 (2000).

Sandgren K et al., "Vasoactive intestinal peptide and nitric oxide promote survival of adult rat myenteric neurons in culture," J Neurosci Res 72(5):595-602 (2003).

Laude K et al., "NO produced by endothelial NO synthase is a mediator of delayed preconditioning-induced endothelial protection," Am J Physiol Heart Circ Physiol 284(6):H2053-60 (2003) (Epub Jan. 9, 2003).

Khan M et al., "S-Nitrosoglutathione reduces inflammation and protects brain against focal cerebral ischemia in a rat model of experimental stroke," J Cereb Blood Flow Metab 25(2):177-92 (2005).

Pluta RM, "Delayed cerebral vasospasm and nitric oxide: review, new hypothesis, and proposed treatment," Pharmacol Ther 105(1):23-56 (2005).

Reis DJ et al., "Electrical stimulation of cerebellar fastigial nucleus reduces ischemic infarction elicited by middle cerebral artery occlusion in rat," J Cereb Blood Flow Metab 11(5):810-8 (1991).

Nollet H et al., "Transcranial magnetic stimulation: review of the technique, basic principles and applications," The Veterinary Journal 166:28-42 (2003).

Devoghel JC, "Cluster headache and sphenopalatine block," Acta Anaesthesiol Belg., 32(1):101-7 (1981)—an abstract.

Delephine et al., "Plasma Protein Extravasation Induced in the Rat Dura Mater by Stimulation of the Parasympathetic Sphenopalatine Ganglion", Experimental Neurology, 147, 389-400, 1997.

Hara et al., "Parasympathetic Cerebrovascular Innervation: An Anterograde Tracing from the Sphenopalatine Ganglion in the Rat", Neurosurgery, 32, 822-827, 1993.

G.L. Ruskell, "The Orbital Branches of the Pterygopalatine Ganglion and their Relationship with Internal Carotid Nerve Branches in Primates", J. Anat. 1970, 106, 2, pp. 323-339.

Kroll RA, Neuwelt EA, "Outwitting the Blood Brain Barrier for Therapeutic Purposes: Osmotic Opening and Other Means", Neurosurgery, 42, 1083-1100, 1998.

Sanders M, et al., "Efficacy of Sphenopalatine Ganglion Blockade in 66 Patients Suffering from Cluster Headache: A 12-70 Month Follow-Up Evaluation", Journal of Neurosurgery, 87, 876-880, 1997.

Suzuki, N. et al., "Selective Electrical Stimulation of postganglionic Cerebrovascular Parasympathetic Nerve Fibers Originating from the Sphenopalatine Ganglion Enhances Cortical Blood Flow in the Rat", Journal of Cerebral Blood Flow and Metabolism, 10, 383-391 (1990).

Samad TA et al., in an article entitled, "Interleukin-1beta-mediated induction of Cox-2 in the CNS contributes to inflammatory pain hypersensitivity," in Nature 410(6827):471-5 (2001).

Van de WaterBeemd, et al., "Estimation of Blood Brain Barrier Crossing of Drugs Using Molecular Size and Shape and H bonding Descriptors", Journal of Drug Targeting, 6, 151-165, 1998.

Ronald F. Young, "Electrical Stimulation of the Trigeminal nerve root for the Treatment of Chronic Facial Pain", J Neurosurg 83:72-78, 1995.

N. Suzuki, et al, "Origins and Pathways of Cerebrovascular Vasoactive Intestinal Polypeptide-Positive Nerves in Rat", J Cereb Blood Flow Metab. vol. 8 No. 5, 1988.

Zhang, R. et al., "Nitric Oxide Enhances Angiogenesis via the Synthesis of Vascular Endothelial Growth Factor and cGMP After Stroke in the Rat", Circ. Res. 2003; 92; 308-313.

Japanese Office Action dated Sep. 16, 2008, which issued during the prosecution of Applicant's Japanese Patent Application No. 2001-581749.

* cited by examiner

FIG. 10A
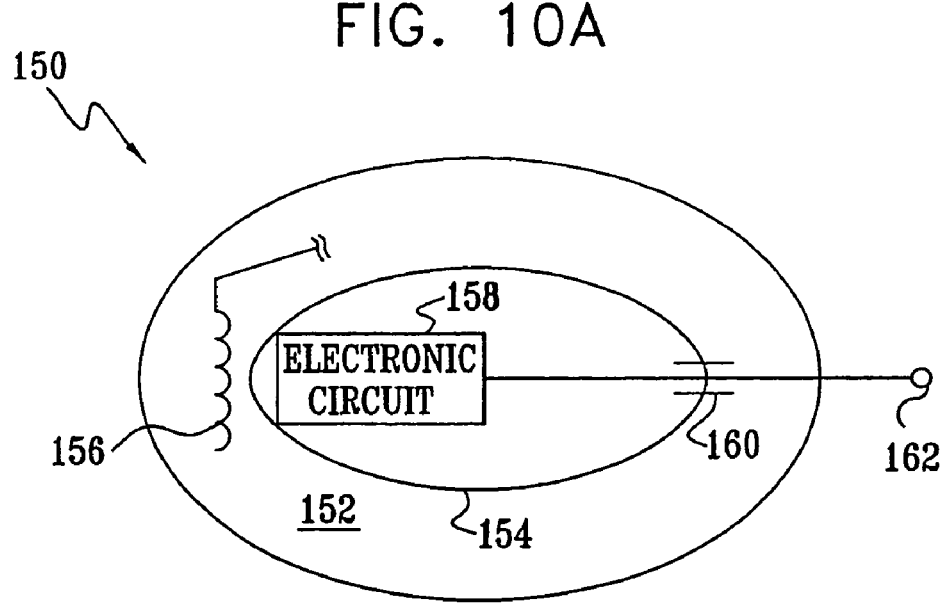
FIG. 10B
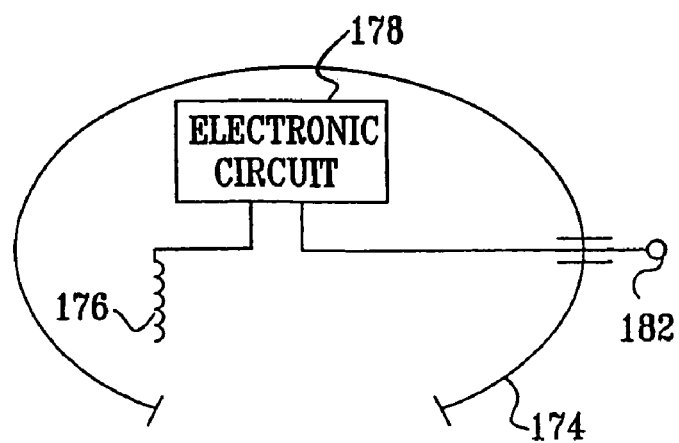

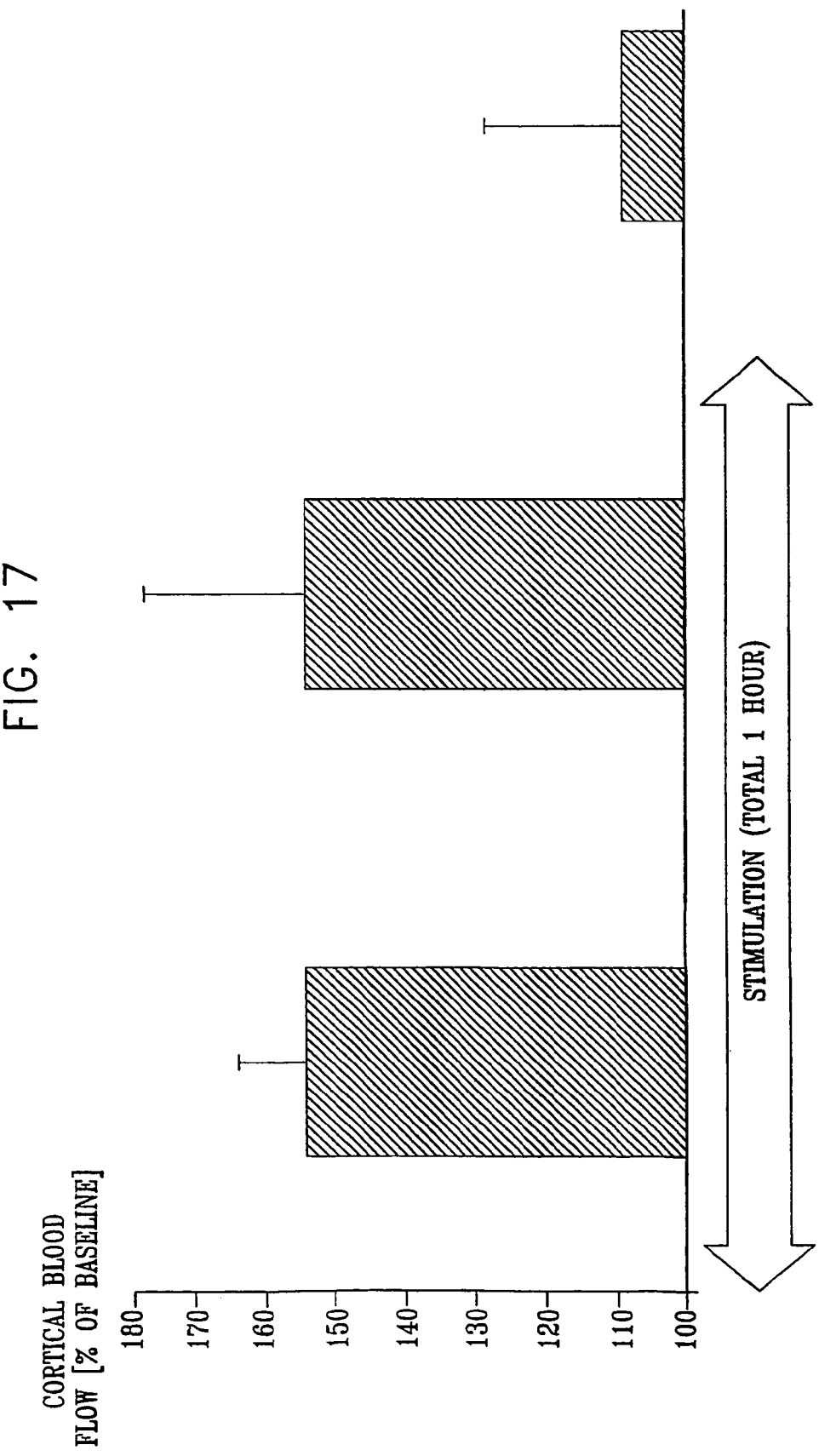

METHODS AND SYSTEMS FOR MANAGEMENT OF ALZHEIMER'S DISEASE

CROSS-REFERENCES TO RELATED APPLICATIONS

This application claims the priority of all of the following patent applications, which are assigned to the assignee of the present patent application and are incorporated herein by reference:

(a) U.S. Provisional Patent Application 60/388,931, filed Jun. 14, 2002, entitled, "Methods and systems for management of Alzheimer's disease"; and (b) This application is a continuation-in-part of U.S. patent application Ser. No. 10/294,310 to Gross et al., entitled, "Stimulation for treating eye pathologies," filed Nov. 14, 2002, now U.S. Pat. No. 7,146,209 which is a continuation-in-part of U.S. patent application Ser. No. 10/258,714 to Shalev and Gross, filed Jan. 22, 2003, now U.S. Pat. No. 7,120,489 entitled, "Method and apparatus for stimulating the sphenopalatine ganglion to modify properties of the BBB and cerebral blood flow," which is a US national phase application corresponding to PCT Patent Application PCT/IL 01/00402, filed May 7, 2001, entitled, "Method and apparatus for stimulating the sphenopalatine ganglion to modify properties of the BBB and cerebral blood flow," which claims priority from U.S. Provisional Patent Application 60/203,172, filed May 8, 2000, entitled, "Method and apparatus for stimulating the sphenopalatine ganglion to modify properties of the BBB and cerebral blood flow." U.S. patent application Ser. No. 10/294,310 also claims priority from: (i) U.S. Provisional Patent Application 60/400,167, filed Jul. 31, 2002, entitled, "Delivering compounds to the brain by modifying properties of the BBB and cerebral circulation" and (ii) U.S. Provisional Patent Application 60/364,451, filed Mar. 15, 2002, entitled, "Applications of stimulating the sphenopalatine ganglion (SPG)."

FIELD OF THE INVENTION

This invention relates to methods and systems used for therapeutic, prophylactic and diagnostic purposes in the management of a disease. More specifically, this invention relates to methods and systems used for therapeutic, prophylactic and diagnostic purposes in the management of Alzheimer's disease (AD).

BACKGROUND OF THE INVENTION

Alzheimer's disease (AD) is the most common form of both senile and presenile dementia in the world and is recognized clinically as relentlessly progressive loss of memory and intellectual function and disturbances in speech (Merritt, 1979, *A Textbook of Neurology*, 6th edition, pp. 484-489, Lea & Febiger, Philadelphia, which is incorporated herein by reference). Alzheimer's disease begins with mildly inappropriate behavior, uncritical statements, irritability, a tendency towards grandiosity, euphoria, and deteriorating performance at work; it progresses through deterioration in operational judgment, loss of insight, depression, and loss of recent memory; and it ends in severe disorientation and confusion, apraxia of gait, generalized rigidity, and incontinence (Gilroy & Meyer, 1979, *Medical Neurology*, pp. 175-179, MacMillan Publishing Co., which is incorporated herein by reference,). Alzheimer's disease is found in about 10% of the population over the age of 65 and 47% of the population over the age of 85 (Evans et al., 1989, JAMA, 262:2551-2556, which is incorporated herein by reference).

Alzheimer's Disease is characterized by the accumulation of insoluble, 10 nm filaments containing β-amyloid (Aβ) peptides, localized in the extracellular space of the cerebral cortex and vascular walls. These 40 or 42 amino acid long Aβ peptides are derived from the larger β-amyloid precursor protein (βAPP) through the endopeptidase action of β and γ secretases. In addition, the post-translational action of putative aminopeptidases results in a heterogeneous shortening of the 40 or 42 amino acid long Aβ peptides that either terminate at residue 40 or 42 and, therefore, are designated as AβN-40 and AβN-42. In familial forms of AD, the pathological appearance of the Aβ peptides in the brain is driven by the presence of mutations in the βAPP gene or in the genes coding for the proteins presenilin 1 and 2.

Sporadic AD accounts for more than 95% of the known AD cases. Its etiology, however, remains obscure. An accepted view is that sporadic AD results from the interplay between an individual's genetic factors and the environment, leading to the deposition of Aβ, neurodegeneration, and dementia. Despite this emerging perspective, insufficient effort has been made in identifying factors responsible for Aβ accumulation in the brain.

The etiology of Alzheimer's disease is unknown. Evidence for a genetic contribution comes from several important observations such as the familial incidence, pedigree analysis, monozygotic and dizygotic twin studies, and the association of the disease with Down's syndrome (for review see Baraitser, 1990, *The Genetics of Neurological Disorders*, 2nd edition, pp. 85-88, which is incorporated herein by reference). Nevertheless, this evidence is far from definitive, and it is clear that other factors are involved.

Alzheimer's Disease is a neurodegenerative disease characterized by a progressive decline of cognitive functions, including loss of declarative and procedural memory, decreased learning ability, reduced attention span, and severe impairment in thinking ability, judgment, and decision making. Mood disorders and depression are also often observed in AD patients. It is estimated that AD affects about 4 million people in the USA and 20 million people worldwide. Because AD is an age-related disorder (with an average onset at 65 years), the incidence of the disease in industrialized countries is expected to rise dramatically as the population of these countries ages.

AD is characterized by the following neuropathological features:

massive loss of neurons and synapses in the brain regions involved in higher cognitive functions (association cortex, hippocampus, amygdala). Cholinergic neurons are particularly affected.

neuritic (senile) plaques that are composed of a core of amyloid material surrounded by a halo of dystrophic neurites, reactive type I astrocytes, and numerous microglial cells (Selkoe, D. J., Annu Rev Neurosci 17:489-517, 1994; Selkoe, D. J., J Neuropathol Exp Neurol 53:438-447, 1994; Dickson, D. W., J Neuropathol Exp Neurol 56:321-339, 1997; Hardy, J. et al., Science 282: 1075-1079, 1998; Selkoe, D. J., Cold Spring Harb Symp Quant Biol 61:587-596, 1996, all of which are incorporated herein by reference. The major component of the core is a peptide of 39 to 42 amino acids called the amyloid β protein, or Aβ. Although the Aβ protein is produced by the intracellular processing of its precursor, APP, the amyloid deposits forming the core of the plaques are extracellular. Studies have shown that the longer form of Aβ (Aβ42) is much more amyloidogenic than the shorter forms (Aβ40 or Aβ39).

neurofibrillary tangles that are composed of paired-helical filaments (PHF) (Ray et al., Mol Med Today 4:151-157, 1998; Brion, Acta Neurol Belg 98:165-174, 1998, both of which are incorporated herein by reference). Biochemical analyses revealed that the main component of PHF is a hyper-phosphorylated form of the microtubule-associated protein τ. These tangles are intracellular structures, found in the cell body of dying neurons, as well as some dystrophic neurites in the halo surrounding neuritic plaques.

Both plaques and tangles are found in the same brain regions affected by neuronal and synaptic loss.

Although the neuronal and synaptic loss is universally recognized as the primary cause of the decline of cognitive functions, the cellular, biochemical, and molecular events responsible for this neuronal and synaptic loss are subject to fierce controversy. The number of tangles shows a better correlation than the amyloid load with the cognitive decline (Albert, Proc Natl Acad Sci USA 93:13547-13551, 1996, which is incorporated herein by reference). On the other hand, a number of studies showed that amyloid can be directly toxic to neurons, resulting in behavioral impairment (Ma et al., Neurobiol Aging 17:773-780, 1996, which is incorporated herein by reference). It has also been shown that the toxicity of some compounds (amyloid or tangles) could be aggravated by activation of the complement cascade, suggesting the possible involvement of inflammatory process in the neuronal death.

Genetic and molecular studies of some familial forms of AD (FAD) have recently provided evidence that boosted the amyloid hypothesis (Ii, Drugs Aging 7:97-109, 1995; Price et al., Curr Opin Neurol 8:268-274, 1995; Hardy, Trends Neurosci 20:154-159, 1997; Selkoe, J Biol Chem 271:18295-18298, 1996, all of which are incorporated herein by reference). The assumption is that since the deposition of Aβ in the core of senile plaques is observed in all Alzheimer cases, if Aβ is the primary cause of AD, then mutations that are linked to FAD should induce changes that, in one way or another, foster Aβ deposition. There are 3 FAD genes known so far (Hardy et al., Science 282:1075-1079, 1998; Ray et al., Mol Med Today 4:151-157, 1998, both of which are incorporated herein by reference), and the activity of all of them results in increased Aβ deposition, a very compelling argument in favor of the amyloid hypothesis.

The first of the 3 FAD genes codes for the Aβ precursor, APP (Selkoe, J Biol Chem 271:18295-18298, 1996, which is incorporated herein by reference). Mutations in the APP gene are very rare, but all of them cause AD with 100% penetrance and result in elevated production of either total Aβ or Aβ42, both in vitro (transfected cells) and in vivo (transgenic animals). The other two FAD genes code for presenilin 1 and 2 (PS1, PS2) (Hardy, Trends Neurosci 20:154-159, 1997, which is incorporated herein by reference). The presenilins contain 8 transmembrane domains and several lines of evidence suggest that they are involved in intracellular protein trafficking, although their exact function is still unknown. Mutations in the presenilin genes are more common than in the APP genes, and all of them also cause FAD with 100% penetrance. In addition, in vitro and in vivo studies have demonstrated that PS1 and PS2 mutations shift APP metabolism, resulting in elevated Aβ42 production. For a recent review on the genetics of AD, see Lippa, J Mol Med 4:529-536, 1999, which is incorporated herein by reference.

In spite of these compelling genetic data, it is still unclear whether Aβ generation and amyloid deposition are the primary cause of neuronal death and synaptic loss observed in AD. Moreover, the biochemical events leading to Aβ production, the relationship between APP and the presenilins, and between amyloid and neurofibrillary tangles are poorly understood. Thus, the picture of interactions between the major Alzheimer proteins is very incomplete, and it is clear that a large number of novel proteins are yet to be discovered.

The diagnosis of Alzheimer's disease at autopsy is definitive. Gross pathological changes are found in the brain, including low weight and generalized atrophy of both the gray and white matter of the cerebral cortex, particularly in the temporal and frontal lobes (Adams & Victor, 1977, *Principles of Neurology*, pp. 401-407 and Merritt, 1979, *A Textbook of Neurology*, 6th edition, Lea & Febiger, Philadelphia, pp. 484-489, both of which are incorporated herein by reference). The histological changes include neurofibrillary tangle (Kidd, Nature 197:192-193, 1963; Kidd, Brain 87:307-320, 1964, both of which are incorporated herein by reference), which consists of a tangled mass of paired helical and straight filaments in the cytoplasm of affected neurons (Oyanagei, Adv. Neurol. Sci. 18:77-88, 1979 and Grundke-Iqbal et al., Acta Neuropathol. 66:52-61, 1985, both of which are incorporated herein by reference).

The diagnosis of Alzheimer's disease during life is more difficult than at autopsy since the diagnosis depends upon inexact clinical observations. In the early and middle stages of the disease, the diagnosis is based on clinical judgment of the attending physician. In the late stages, where the symptoms are more recognizable, clinical diagnosis is more straightforward. But, in any case, before an unequivocal diagnosis can be made, other diseases, with partially overlapping symptoms, must be ruled out. Usually a patient must be evaluated on a number of occasions to document the deterioration in intellectual ability and other signs and symptoms. The necessity for repeated evaluation is costly, generates anxiety, and can be frustrating to patients and their families. Furthermore, the development of an appropriate therapeutic strategy is hampered by the difficulties of rapid diagnosis, particularly in the early stages where early intervention could leave the patient with significant intellectual capacity and a reasonable quality of life. In brief, no unequivocal laboratory test specific for Alzheimer's disease has been reported.

Alzheimer's disease is associated with degeneration of cholinergic neurons, in the basal forebrain, which play a fundamental role in cognitive functions, including memory (Becker et al., Drug Development Research 12:163-195, 1988, which is incorporated herein by reference). Progressive, inexorable decline in cholinergic function and cholinergic markers in the brain of Alzheimer's disease patients has been observed in numerous studies, and includes, for example, a marked reduction in acetylcholine synthesis, choline acetyltransferase activity, acetylcholinesterase activity, and choline uptake (Davis, Brain Res. 171:319-327, 1979 and Hardy et al., Neurochem. Int. 7:545-563, 1985, which are incorporated herein by reference). Even more, decreased cholinergic function may be an underlying cause of cognitive decline seen in Alzheimer's-disease patients (Kish et al., J. Neurol., Neurosurg., and Psych 51:544-548, 1988, which is incorporated herein by reference). Choline acetyltransferase and acetylcholinesterase activities decrease significantly as plaque count rises, and, in demented subjects, the reduction in choline acetyl transferase activity was found to correlate with intellectual impairment (Perry, et al., Brit. Med. J. 25, Nov. 1978, p. 1457, which is incorporated herein by reference).

Nerve cells produce nerve growth factors, proteins that regulate cell maturation during prenatal development and also play an important role in cell survival, repair, and regeneration during adult life. Because of their significance in cell maintenance and repair, these factors have attracted attention as potential treatments in Alzheimer's disease, stroke, spinal cord injury, and other neurodegenerative conditions. However, nerve growth factors are usually too large to cross the blood-brain barrier (BBB), a protective shield that restricts passage of molecules to the brain.

The BBB is functionally situated at the brain capillaries endothelium layer and covers a surface area of 12 m2/g of brain parenchyma. The total length of this capillary network is 650 km. The cerebral capillary endothelial cell displays some peculiar morphologic characteristics that form the anatomic basis of the blood-brain barrier. It differs from the peripheral capillary endothelial cell (referring to all non-CNS sites) in a number of ways:

First, the CNS endothelial cell layer is not fenestrated. Cells are joined by tight junctions composed of 6 to 8 pentalaminar structures. They actively block protein movements, hydrophilic transfer and even ionic diffusion. Thus, there is very little movement of compounds between endothelial cells from the blood to the CNS.

Second, and in contrast to the peripheral capillary endothelial cell, transcellular movement of molecules through the non-specific mechanism of fluid-phase endocytosis is generally absent. The cerebral vascular endothelial cell possesses a transcellular lipophilic pathway, allowing diffusion of small lipophilic compounds. In addition to this route, specific receptor-mediated transport systems are present for given molecules, like insulin, transferrin, glucose, purines and amino acids. These transport systems are highly selective and asymmetric.

Third, the CNS endothelial cell displays a net negative charge at its endoluminal side and at the basement membrane. This provides an additional selective mechanism by impeding anionic molecules to cross the membrane.

Fourth, the cerebral endothelial cell has very few pinocytic vesicles, and these vesicles are not involved in any transport function.

Fifth, astrocyte foot processes surround the microvascular endothelium and cover more than 95 percent of its surface, therefore interposing between capillaries and cerebral neuropil.

By virtue of this selective barrier, the CNS can preferentially regulate the extracellular concentration of certain solutes, growth factors and neurotransmitters, keep certain molecules in the CNS and isolate itself from some others, and further isolate itself from sudden systemic homeostatic changes. It is therefore an integral component of the mechanisms involved in the tight regulation of the extra-cellular homeostasis necessary to the normal CNS function. This relatively impermeable barrier has some drawbacks, however, when considering the therapeutic delivery of a molecule to the CNS.

The delivery of therapeutic molecules across the BBB has proven to be a major obstacle in treating various brain disorders. The normal blood-brain barrier prevents passage of ionized water-soluble compounds with a molecular weight greater than 180 Daltons. Therefore, the BBB is a major impediment to the treatment of CNS diseases as many drugs are unable to reach this organ at therapeutic concentrations. More than 98% of the CNS-targeted drugs do not cross the BBB. Example of such disorders are: primary brain tumors, metastatic brain tumors, AD, addiction, ALS, head injury, Huntington's disease, multiple sclerosis (MS), depression, Cerebral Palsy, schizophrenia, epilepsy, stress and anxiety. Many new neurotherapeutic agents are being discovered, but because of a lack of suitable strategies for drug delivery across the BBB, these agents are ineffective. Such drugs will only become effective if strategies for brain delivery are developed in parallel.

Apart from molecular parameters, the permeability of the BBB and active transport mechanisms, a major determinant of molecular transport across the BBB is their concentration gradient—between the CNS and the cerebral circulation.

Additionally, the functioning BBB inhibits clearance of neurotoxic compounds, such as β-Amyloid, tau, PS1, and PS2, from the CNS into the systemic circulation. These neurotoxic compounds are therefore not metabolized and removed from the body to the extent desired, and therefore continue to have undesired effects in the CNS.

U.S. Pat. No. 5,752,515 to Jolesz et al., which is incorporated herein by reference, describes apparatus for image-guided ultrasound delivery of compounds through the blood-brain barrier. Ultrasound is applied to a site in the brain to effect in the tissues and/or fluids at that location a change detectable by imaging. At least a portion of the brain in the vicinity of the selected location is imaged, e.g., via magnetic resonance imaging, to confirm the location of that change. A compound, e.g., a neuropharmaceutical, in the patients bloodstream is delivered to the confirmed location by applying ultrasound to effect opening of the blood-brain barrier at that location and, thereby, to induce uptake of the compound there.

The following references, which are incorporated herein by reference, may be useful:

Delepine L, Aubineau P, "Plasma protein extravasation induced in the rat dura mater by stimulation of the parasympathetic sphenopalatine ganglion," Experimental Neurology, 147, 389-400 (1997)

Hara H, Zhang Q J, Kuroyanagi T, Kobayashi S, "Parasympathetic cerebrovascular innervation: An anterograde tracing from the sphenopalatine ganglion in the rat," Neurosurgery, 32, 822-827 (1993)

Jolliet-Riant P, Tillement J P, "Drug transfer across the blood-brain barrier and improvement of brain delivery," Fundam. Clin. Pharmacol., 13, 16-25 (1999)

Kroll R A, Neuwelt E A, "Outwitting the blood brain barrier for therapeutic purposes: Osmotic opening and other means," Neurosurgery, 42, 1083-1100 (1998)

Sanders M, Zuurmond W W, "Efficacy of sphenopalatine ganglion blockade in 66 patients suffering from cluster headache: A 12-70 month follow-up evaluation," Journal of Neurosurgery, 87, 876-880 (1997)

Syelaz J, Hara H, Pinard E, Mraovitch S, MacKenzie E T, Edvinsson L, "Effects of stimulation of the sphenopalatine ganglion on cortical blood flow in the rat," Journal of Cerebral Blood Flow and Metabolism," 8, 875-878 (1988)

Van de Waterbeemd H, Camenisch G, Folkers G, Chretien J R, Raevsky O A, "Estimation of blood brain barrier crossing of drugs using molecular size and shape and h bonding descriptors," Journal of Drug Targeting," 6, 151-165, (1998)

Suzuki N, Hardebo J E, Kahrstrom J, Owman C, "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383-391 (1990)

Suzuki N, Hardebo J E, Kahrstrom J, Owman C H, "Effect on cortical blood flow of electrical stimulation of trigeminal cerebrovascular nerve fibres in the rat," Acta Physiol. Scand., 138, 307-315 (1990)

Major A, Silver W, "Odorants presented to the rat nasal cavity increase cortical blood flow," Chem. Senses, 24, 665-669 (1999)

Fusco B M, Fiore G, Gallo F, Martelletti P, Giacovazzo M, "'Capsaicin-sensitive' sensory neurons in cluster headache: pathophysiological aspects and therapeutic indications," Headache, 34, 132-137 (1994)

Lambert G A, Bogduk N, Goadsby P J, Duckworth J W, Lance J W, "Decreased carotid arterial resistance in cats in response to trigeminal stimulation," Journal of Neurosurgery, 61, 307-315 (1984)

Silver W L, "Neural and pharmacological basis for nasal irritation," in Tucker W G, Leaderer B P, Mølhave L, Cain W S (eds), Sources of Indoor Air Contaminants, Ann NY Acad. Sci., 641, 152-163 (1992)

Silver W, "Chemesthesis: the burning questions," ChemoSense, Vol. 2 No. 1, 1-2 (1999)

Asaba H, Hosoya K, Takanaga H, Ohtsuki S, Tamura E, Takizawa T, Terasaki T, "Blood-Brain barrier is involved in the efflux transport of a neuroactive steroid, dehydroepiandrosterone sulfate, via organic anion transporting polypeptide 2," J. Neurochem. 75(5):1907-1916 (2000)

Isakovica A J, Segalb M B, Milojkovica B A, Dacevica M P, Misirlica S T, Rakicc M L, Redzicb Z B, "The efflux of purine nucleobases and nucleosides from the rat brain," Neuroscience Letters 318:65-68 (2002)

Kakee A, Terasaki T, Sugiyama Y, "Brain efflux index as a novel method of analyzing efflux transport at the blood-brain barrier," J. Pharmacol. Exp. Ther. 277:1550-1559 (1996)

Kakee A, Terasaki T, Sugiyama Y, "Selective brain to blood efflux transport of para-aminohippuric acid across the blood-brain barrier: in vivo evidence by use of the brain efflux index method," J. Pharmacol. Exp. Ther. 283:1018-1025 (1997)

Takasawa K, Terasaki T, Suzuki H, Sugiyama Y, "In vivo evidence for carrier-mediated efflux transport of 39-azido-39-deoxythymidine and 29,39-dideoxyinosine across the blood-brain barrier via a probenecid-sensitive transport system," J. Pharmacol. Exp. Ther. 281:369-375 (1997)

Hosoya K, Sugawara M, Asaba H, Terasaki T, "Blood-brain barrier produces significant efflux of L-aspartic acid, but not D-aspartic acid: in vivo evidence using the brain efflux index method," J. Neurochem. 73:1206-1211 (1999)

Boado R J, "Antisense delivery through the blood brain barrier," Adv. Drug. Del. Rev. 15:73-107 (1995)

SUMMARY OF THE INVENTION

It is an object of some aspects of the present invention to provide improved methods and apparatus for delivery of compounds to the brain, particularly through the BBB.

It is also an object of some aspects of the present invention to provide such methods and apparatus as can be employed to deliver such compounds through the BBB with a minimally invasive approach.

It is a further object of some aspects of the present invention to provide such methods and apparatus as can facilitate delivery of large molecular weight compounds through the BBB.

It is yet a further object of some aspects of the present invention to provide cost-effective methods and apparatus for delivery of compounds through the BBB.

It is still a further object of some aspects of the present invention to provide improved methods and apparatus for remedying or modifying neurological activities and disorders via delivery of compounds through the BBB.

It is also a further object of some aspects of the present invention to modulate cerebral blood flow.

It is an additional object of some aspects of the present invention to provide improved methods and apparatus for treating and/or preventing neurological diseases, whose prognosis and evolution of pathological symptoms are influenced by cerebral blood flow.

It is still an additional object of some aspects of the present invention to provide improved methods and apparatus for treating and/or preventing Alzheimer's disease.

It is also an object of some aspects of the present invention to provide improved methods and apparatus for diagnosing neurological diseases.

It is a further object of some aspects of the present invention to provide improved methods and apparatus for diagnosing Alzheimer's disease.

It is yet a further object of some aspects of the present invention to provide implantable apparatus which affects a property of the brain, without actually being implanted in the brain.

It is still a further object of some aspects of the present invention to provide methods which affect a property of the brain without the use of implantable apparatus.

It is also a further object of some aspects of the present invention to affect a property of the brain by using the neuroexcitatory and/or neuroinhibitory effects of odorants on nerves in the head.

These and other objects of the invention will become more apparent from the description of preferred embodiments thereof provided hereinbelow.

In preferred embodiments of the present invention, an electrical stimulator drives current into the sphenopalatine ganglion (SPG) or into related neuroanatomical structures, including neural tracts originating or reaching the SPG, including outgoing and incoming parasympathetic and sympathetic tracts and other parasympathetic centers. Typically, the stimulator drives the current in order to control and/or modify SPG-related behavior, e.g., in order to induce changes in cerebral blood flow and/or to modulate permeability of the blood-brain barrier (BBB). These embodiments may be used in many medical applications, such as, by way of illustration and not limitation, (a) the treatment of cerebrovascular disorders such as stroke, (b) the treatment of migraine, cluster and other types of headaches, or (c) the facilitation of drug transport across the BBB.

In the specification of the present patent application, unless indication to the contrary is stated, stimulation of the SPG is to be understood to alternatively or additionally include stimulation of one or more of the following nerves or ganglions:

an anterior ethmoidal nerve;
a posterior ethmoidal nerve;
a communicating branch between the anterior ethmoidal nerve and the SPG (retro orbital branch);
a communicating branch between the posterior ethmoidal nerve and the SPG (retro orbital branch)
a nerve of the pterygoid canal (also called a vidian nerve), such as a greater superficial
a petrosal nerve (a preganglionic parasympathetic nerve) or a lesser deep petrosal nerve (a postganglionic sympathetic nerve);
a greater palatine nerve;
a lesser palatine nerve;
a sphenopalatine nerve;
a communicating branch between the maxillary nerve and the sphenopalatine ganglion;
a nasopalatine nerve;

a posterior nasal nerve;

an infraorbital nerve;

an otic ganglion;

an afferent fiber going into the otic ganglion; and/or an efferent fiber going out of the otic ganglion.

It is to be appreciated that, whereas some preferred embodiments of the present invention are described with respect to driving current into the SPG or into neural structures directly related thereto, the scope of the present invention includes driving current into other sites in the brain which upon stimulation modulate cerebral blood flow or modulate permeability properties of the BBB, as appropriate for a given application.

It is also to be appreciated that electrical "stimulation," as provided by preferred embodiments of the present invention, is meant to include substantially any form of current application to designated tissue, even when the current is configured to block or inhibit the activity of nerves.

It is further to be appreciated that implantation and stimulation sites, methods of implantation, and parameters of stimulation are described herein by way of illustration and not limitation, and that the scope of the present invention includes other possibilities which would be obvious to someone of ordinary skill in the art who has read the present patent application.

It is yet further to be appreciated that while preferred embodiments of the invention are generally described herein with respect to electrical transmission of power and electrical stimulation of tissue, other modes of energy transport may be used as well. Such energy includes, but is not limited to, direct or induced electromagnetic energy, RF transmission, ultrasonic transmission, optical power, and low power laser energy (via, for example, a fiber optic cable).

It is additionally to be appreciated that whereas preferred embodiments of the present invention are described with respect to application of electrical currents to tissue, this is to be understood in the context of the present patent application and in the claims as being substantially equivalent to applying an electrical field, e.g., by creating a voltage drop between two electrodes.

The SPG is a neuronal center located in the brain behind the nose. It consists of parasympathetic neurons innervating the middle cerebral and anterior cerebral lumens, the facial skin blood vessels, and the lacrimal glands. Activation of this ganglion is believed to cause vasodilation of these vessels. A second effect of such stimulation is the opening of pores in the vessel walls, causing plasma protein extravasation (PPE). This effect allows better transport of molecules from within these blood vessels to surrounding tissue.

The middle and anterior cerebral arteries provide the majority of the blood supply to the cerebral hemispheres, including the frontal and parietal lobes in their entirety, the insula and the limbic system, and significant portions of the following structures: the temporal lobes, internal capsule, basal ganglia and thalamus. These structures are involved in many of the neurological and psychiatric diseases of the brain, and preferred embodiments of the present invention are directed towards providing improved blood supply and drug delivery to these structures.

There is also animal evidence for the presence of SPG-originated parasympathetic innervation in the posterior cerebral and basilar arteries. Consistent with the assumption that this is also the case in humans, many regions of the human brain are within the reach of treatments provided by preferred embodiments of the present invention, as described hereinbelow.

Currently the SPG is a target of manipulation in clinical medicine, mostly in attempted treatments of severe headaches such as cluster headaches. The ganglion is blocked either on a short-term basis, by applying lidocaine, or permanently, by ablation with a radio frequency probe. In both cases the approach is through the nostrils. In some preferred embodiments of the present invention, similar methods for approaching the SPG are utilized, to enable the electrical stimulation or electrical blocking thereof.

According to a preferred embodiment of the instant invention, a method and apparatus are provided to enhance delivery of therapeutic molecules across the BBB by stimulation of the SPG and/or its outgoing parasympathetic tracts and/or another parasympathetic center. The apparatus typically stimulates the parasympathetic nerve fibers of the SPG, thereby inducing the middle and anterior cerebral arteries to dilate, and also causing the walls of these cerebral arteries to become more permeable to large molecules. In this manner, the movement of large pharmaceutical molecules from within blood vessels to the cerebral tissue is substantially increased. Preferably, therefore, this method can serve as a neurological drug delivery facilitator, without the sacrifices in molecular weight required by techniques of the prior art.

Advantageously (and even in the absence of BBB permeability changes), patients with these and other disorders are generally helped by the vasodilation secondary to stimulation of the SPG, and the resultant improvement in oxygen supply to neurons and other tissue. For some applications, this treatment is given on a long-term basis, e.g., in the chronic treatment of Alzheimer's patients. For other applications, the treatment is performed on a short-term basis, e.g., to minimize the damage following an acute stroke event and initiate neuronal and therefore functional rehabilitation.

Alternatively or additionally, the changes induced by electrical stimulation as described hereinabove are achieved by presenting odorants to an air passage of a patient, such as a nasal cavity or the throat. There is animal evidence that some odorants, such as propionic acid, cyclohexanone, and amyl acetate, significantly increase cortical blood flow when presented to the nasal cavity. This has been interpreted by some researchers as evidence that these odorants (e.g., environmental pollutants) may be involved in the formation of various headaches by increasing cerebral blood flow. The temporal profile and other quantitative characteristics of such odorant stimulation are believed by the present inventors to have a mechanism of action that has a neuroanatomical basis overlapping with that of the electrical stimulation of the SPG. Furthermore, experimental animal evidence collected by the inventors and described in a U.S. provisional patent application to Shalev and Gross entitled, "SPG stimulation," filed Mar. 28, 2002, which is assigned to the assignee of the present invention and is incorporated herein by reference, suggest a correlation between the mechanisms of increasing cerebral blood flow and increased cerebrovascular permeability. It is hypothesized that such increased cerebral blood flow caused by odorants is a result of stimulation of parasympathetic and/or trigeminal fibers. These fibers may mediate cerebral blood flow changes directly, by communicating with the SPG, or by some other mechanism. It is also hypothesized that these odorants stimulate via reflex arcs the SPG or other autonomic neural structures that innervate the cerebrovascular system. Therefore, the inventors hypothesize, odorant "stimulation" may increase cerebral blood flow in general, and cortical blood flow in particular, by some or all of the same mechanisms as electrical stimulation, as described hereinabove. Alternatively or additionally, odorants may cause increased cortical blood flow by other mechanisms, such as by entering the blood stream and reaching the affected blood vessels in the brain or by parasympathetic stimulation via the olfactory nerve. In addition to the effect on cerebral blood flow, the introduction of odorants into an air passage is also believed by the inventors to induce an increase in the permeability of the anterior two thirds of the cerebrovascular system to circulating agents of various sizes, i.e. to increase the permeability of the BBB. Similarly, presenting certain other odorants to an air passage decreases cerebral blood flow and decreases the permeability of the BBB.

Odorants that may increase or decrease cerebral blood flow and/or the permeability of the BBB include, but are not limited to, propionic acid, cyclohexanone, amyl acetate, acetic acid, citric acid, carbon dioxide, sodium chloride, ammonia, menthol, alcohol, nicotine, piperine, gingerol, zingerone, allyl isothiocyanate, cinnamaldehyde, cuminaldehyde, 2-propenyl/2-phenylethyl isothiocyanate, thymol, and eucalyptol.

According to a preferred embodiment of the instant invention, a method is provided to enhance delivery of therapeutic molecules across the BBB by presenting an odorant to an air passage of a patient, such as a nasal cavity or the throat In a preferred application, this method serves as a neurological drug delivery facilitator. The odorant is preferably presented using apparatus known in the art, such as aqueous spray nasal inhalers; metered dose nasal inhalers; or air-dilution olfactometers. Alternatively or additionally, the odorant is presented by means of an orally-dissolvable capsule that releases the active odorants upon contact with salivary liquids. The odorants reach the appropriate neural structures and induce vasodilatation, vasoconstriction and/or cerebrovascular permeability changes. Delivery of a drug can be achieved by mixing the drug with the odorant; by intravenously, intraperitoneally, or intramuscularly administering the drug, or by other delivery methods known in the art. For some applications, it is desirable to combine a local analgesic with the odorant in order to diminish any possible sensation of pain or discomfort that may directly or indirectly (e.g., via a reflex arc) accompany the odorant action upon nerves in the head. For example, preventing neural transmission in the neighboring pain fibers may be performed as a "pre-odorant" treatment, by topical administration of capsaicin together with a local analgesic for several days prior to the use of odorant stimulation. In this manner, the odorants typically induce the SPG-related response with a reduced or eliminated sensation of pain or discomfort.

Alternatively or additionally, a method is provided for increasing or reducing cortical blood flow and/or inducing or inhibiting vasodilation (even in the absence of BBB permeability changes) by presenting an odorant to an air passage of a patient, such as a nasal cavity or the throat, for treatment of a condition. Patients with the aforementioned disorders and other disorders are generally helped by vasodilation and the resultant improvement in oxygen supply to neurons and other tissue. For some applications, this treatment is given on a long-term basis, e.g., in the chronic treatment of Alzheimer's patients. For other applications, the treatment is performed on a short-term basis, e.g., to minimize the damage following an acute stroke event and initiate neuronal and therefore functional rehabilitation. Alternatively or additionally, the method provided above can be used for diagnostic purposes or in conjunction with other diagnostic methods and/or apparatus known in the art, in order to enhance diagnostic results, reduce procedure risk, reduce procedure time, or otherwise improve such diagnostic procedures and/or diagnostic results. For example, methods and apparatus described herein may be used to increase the uptake into the brain of a radio-opaque material, in order to facilitate a CT scan.

In general, it is believed that substantially all pharmacological treatments aimed at cerebral cells for neurological and psychiatric disorders are amenable for use with these embodiments of the present invention. In particular, these embodiments may be adapted for use in the treatment of disorders such as brain tumors, epilepsy, Parkinson's disease, Alzheimer's disease, multiple sclerosis, schizophrenia, depression, stress, anxiety, disorders requiring the administration of various growth factors, and other CNS disorders that are directly or indirectly affected by changes in cerebral blood flow or by BBB permeability changes.

There is therefore provided, in accordance with a preferred embodiment of the present invention, apparatus for modifying a property of a brain of a patient, including:

one or more electrodes, adapted to be applied to a site selected from a group of sites consisting of: a sphenopalatine ganglion (SPG) of the patient and a neural tract originating in or leading to the SPG; and a control unit, adapted to drive the one or more electrodes to apply a current to the site capable of inducing an increase in permeability of a blood-brain barrier (BBB) of the patient.

There is also provided, in accordance with a preferred embodiment of the present invention, apparatus for modifying a property of a brain of a patient, including:

one or more electrodes, adapted to be applied to a site selected from a group of sites consisting of a sphenopalatine ganglion (SPG) of the patient and a neural tract originating in or leading to the SPG; and a control unit, adapted to drive the one or more electrodes to apply a current to the site capable of inducing an increase in cerebral blood flow of the patient.

There is further provided, in accordance with a preferred embodiment of the present invention, apparatus for modifying a property of a brain of a patient, including:

one or more electrodes, adapted to be applied to a site selected from a group of sites consisting of: a sphenopalatine ganglion (SPG) of the patient and a neural tract originating in or leading to the SPG; and a control unit, adapted to drive the one or more electrodes to apply a current to the site capable of inducing a decrease in cerebral blood flow of the patient.

There is still further provided, in accordance with a preferred embodiment of the present invention, apparatus for modifying a property of a brain of a patient, including:

one or more electrodes, adapted to be applied to a site selected from a group of sites consisting of: a sphenopalatine ganglion (SPG) of the patient and a neural tract originating in or leading to the SPG; and a control unit, adapted to drive the one or more electrodes to apply a current to the site capable of inhibiting parasympathetic activity of the SPG.

Preferably, the one or more electrodes are adapted for a period of implantation in the patient greater than about one month.

In a preferred embodiment, the apparatus includes a wire, adapted to connect the control unit to the one or more electrodes, wherein the control unit is adapted to drive the one or more electrodes from a position external to the patient.

Alternatively or additionally, the control unit is adapted to drive the one or more electrodes by wireless communication from a position external to the patient. In a preferred embodiment, the apparatus includes an electromagnetic coupling, adapted to couple the control unit and the one or more electrodes. Alternatively or additionally, the control unit is adapted to be in electro-optical communication with the one or more electrodes. Further alternatively or additionally, the control unit is adapted to be in electro-acoustic communication with the one or more electrodes. Still further alternatively or additionally, the control unit is adapted to be implanted in a nasal cavity of the patient.

Preferably, the one or more electrodes are adapted to be implanted in a nasal cavity of the patient. For some applications, at least one of the one or more electrodes includes a flexible electrode, adapted for insertion through a nostril of the patient and to extend therefrom to the site.

The apparatus preferably includes at least one biosensor, adapted to measure a physiological parameter of the patient and to generate a signal responsive thereto. The control unit, in turn, is preferably adapted to modify a parameter of the applied current responsive to the signal. As appropriate, the biosensor may include one or more of the following:

- a blood flow sensor.
- a temperature sensor.
- a chemical sensor.
- an ultrasound sensor.
- transcranial Doppler (TCD) apparatus.
- laser-Doppler apparatus.
- a systemic blood pressure sensor.
- an intracranial blood pressure sensor.
- a detecting element adapted to be fixed to a cerebral blood vessel, and wherein the control unit is adapted to analyze the signal to detect an indication of a change in blood pressure indicative of a clot.
- a kinetics sensor (in this case, the control unit is typically adapted to analyze the signal to detect an indication of a change in body disposition of the patient).
- an electroencephalographic (EEG) sensor.
- a blood vessel clot detector.

In a preferred embodiment, the control unit is adapted to configure the current so as to facilitate uptake of a drug through the BBB when the permeability of the BBB is increased.

Alternatively or additionally, the control unit is adapted to configure the current so as to increase a diameter of a blood vessel and allow an embolus that is located at a site in the blood vessel to move from the site in the blood vessel.

Further alternatively or additionally, the control unit is adapted to drive the one or more electrodes to apply the current responsive to an indication of stroke.

Still further alternatively or additionally, the control unit is adapted to drive the one or more electrodes to apply the current responsive to an indication of migraine of the patient.

There is also provided, in accordance with a preferred embodiment of the present invention, a method for modifying a property of a brain of a patient, including:

selecting a site from a group of sites consisting of: a sphenopalatine ganglion (SPG) of the patient and a neural tract originating in or leading to the SPG; and applying a current to the site capable of inducing an increase in permeability of a blood-brain barrier (BBB) of the patient.

There is additionally provided, in accordance with a preferred embodiment of the present invention, a method for modifying a property of a brain of a patient, including:

selecting a site from a group of sites consisting of: a sphenopalatine ganglion (SPG) of the patient and a neural tract originating in or leading to the SPG; and applying a current to the site capable of inducing an increase in cerebral blood flow of the patient.

There is yet additionally provided, in accordance with a preferred embodiment of the present invention, a method for modifying a property of a brain of a patient, including:

selecting a site from a group of sites consisting of: a sphenopalatine ganglion (SPG) of the patient and a neural tract originating in or leading to the SPG; and applying a current to the site capable of inducing a decrease in cerebral blood flow of the patient.

There is still additionally provided, in accordance with a preferred embodiment of the present invention, a method for modifying a property of a brain of a patient, including:

selecting a site from a group of sites consisting of: a sphenopalatine ganglion (SPG) of the patient and a neural tract originating in or leading to the SPG; and applying a current to the site capable of inhibiting parasympathetic activity of the SPG.

For some applications, the one or more electrodes are adapted for a period of implantation in the patient less than about one week.

There is further provided, in accordance with a preferred embodiment of the present invention, vascular apparatus, including:

a detecting element, adapted to be fixed to a blood vessel of a patient and to generate a signal responsive to energy coming from the blood vessel; and a control unit, adapted to analyze the signal so as to determine an indication of an embolus in the blood vessel.

Preferably, the detecting element includes an energy transmitter and an energy receiver. For example, the energy transmitter may include an ultrasound transmitter or a transmitter of electromagnetic energy.

There is yet further provided, in accordance with a preferred embodiment of the present invention, a method for detecting, including:

fixing a detecting element to a blood vessel of a patient;

generate a signal responsive to energy coming from the blood vessel; and analyzing the signal so as to determine an indication of an embolus in the blood vessel.

There is still further provided, in accordance with a preferred embodiment of the present invention, a method for treating Alzheimer's disease (AD), including stimulating a sphenopalatine ganglion (SPG) of a subject so that the concentration of a substance in a brain of the subject changes.

In a preferred embodiment, the stimulation causes increased clearance of the substance from the brain. As appropriate, the substance may be one or more of the following:

- amyloid;
- tau protein;
- PS1;
- PS2;
- RNA fragments;
- cytokine;
- a marker of neuronal death;
- a marker of neuronal degeneration;
- a marker of an inflammatory process; and
- a neurotoxic substance.

Alternatively or additionally, the substance may include DNA.

In another preferred embodiment, the stimulation causes increased clearance of the substance from cerebrospinal fluid (CSF). As appropriate, the substance may be one or more of the following:

- amyloid;
- tan protein;
- PS1;
- PS2;
- RNA fragments;
- cytokine;
- a marker of neuronal death;

a marker of neuronal degeneration;
a marker of an inflammatory process; and
a neurotoxic substance.

Alternatively or additionally, the substance may include DNA

There is additionally provided, in accordance with a preferred embodiment of the present invention, a method for treating Alzheimer's disease (AD), including:
supplying a pharmaceutical agent to blood of a subject; and
stimulating a sphenopalatine ganglion (SPG) of the subject so that the concentration of the pharmaceutical agent in a brain of the subject increases.

As appropriate, the pharmaceutical agent may be one or more of the following:
a glutamate receptor antagonist;
a β-amyloid inhibitor;
an NMDA-receptor blocker;
a combination of an AD vaccine and an anti-inflammatory drug;
a microglial activation modulator;
a cholinesterase inhibitor;
a stimulant of nerve regeneration;
a nerve growth factor,
a compound that stimulates production of nerve growth factor,
an antioxidant;
a hormone;
an inhibitor of protein tyrosine phosphatases;
medium chain triglycerides;
an endogenous protein;
a gene therapy agent;
an anti-inflammatory drug;
a non-steroidal anti-inflammatory drug; and
an AD vaccine. More specifically, the AD vaccine may contain antibodies against a specific protein that is characteristic of AD. Still more specifically, the AD vaccine may contain antibodies against β-amyloid and/or antibodies against tau protein.

Alternatively, the pharmaceutical agent is adapted to have an inhibitory effect on the derivation of β-amyloid from amyloid precursor protein.

There is yet additionally provided, in accordance with a preferred embodiment of the present invention, a method for diagnosing Alzheimer's disease (AD), including stimulating a sphenopalatine ganglion (SPG) of a subject so that molecular passage increases between a central nervous system (CNS) of the subject and another body compartment of the subject.

Preferably, the method includes measuring a constituent of the other body compartment. As appropriate, the other body compartment may be one of the following:
blood of the subject;
a plasma of the subject;
serum of the subject; and
ascites of the subject.

There is still additionally provided, in accordance with a preferred embodiment of the present invention, a method for diagnosing Alzheimer's disease (AD), including stimulating a sphenopalatine ganglion (SPG) of a subject so that molecular passage increases between cerebrospinal fluid (CSF) of the subject and another body fluid of the subject.

Preferably, the method includes measuring a constituent of the other body fluid. More preferably, the method includes correlating an abnormal concentration of the constituent to a pathology of AD. As appropriate, the constituent may be selected from the group consisting of the following: a protein, a hormone, an antibody, an electrolyte, a neuropeptide, and an enzyme.

Alternatively or additionally, the measurement is performed by sampling a fluid selected from the group consisting of the following: whole blood, plasma, serum, and ascites. Further alternatively or additionally, the measurement is performed by extracting the fluid from tissue of the subject.

Optionally, the measurement may be performed by measuring more than one constituent In this case, a diagnostic result may be determined according to the interrelation between concentrations of the constituents.

There is also provided, in accordance with a preferred embodiment of the present invention, a method for diagnosing Alzheimer's disease (AD), including stimulating a sphenopalatine ganglion (SPG) of a subject so that molecular passage increases between cerebrospinal fluid (CSF) of the subject and a tissue of the subject.

Preferably, the method includes measuring a constituent of the tissue. More preferably, the method includes correlating an abnormal concentration of the constituent to a pathology of AD. As appropriate, the constituent may be selected from the group consisting of the following: a protein, a hormone, an antibody, an electrolyte, a neuropeptide, and an enzyme.

Optionally, the measurement may be performed by measuring more than one constituent. In this case, a diagnostic result may be determined according to the interrelation between concentrations of the constituents.

There is further provided, in accordance with a preferred embodiment of the present invention, a system for treating Alzheimer's disease (AD), including a stimulator for stimulating the sphenopalatine ganglion (SPG) of a subject, so that the concentration of a substance in a brain of the subject changes.

There is yet further provided, in accordance with a preferred embodiment of the present invention, a pharmaceutical agent delivery system for treating Alzheimer's disease (AD), including:
a pharmaceutical agent supplied to a body of a subject for delivery to a brain of the subject via blood of said subject; and
a stimulator for stimulating a sphenopalatine ganglion (SPG) of the subject, so that the concentration of the pharmaceutical agent in the brain increases.

There is still further provided, in accordance with a preferred embodiment of the present invention, a system for diagnosing Alzheimer's disease (AD), including a stimulator for stimulating a sphenopalatine ganglion (SPG) of a subject, so that molecular passage increases between a CNS of the subject and another body compartment of the subject.

There is additionally provided, in accordance with a preferred embodiment of the present invention, a system for diagnosing Alzheimer's disease (AD), including a stimulator for stimulating a sphenopalatine ganglion (SPG) of a subject, so that molecular passage increases between cerebrospinal fluid (CSF) of the subject and another body fluid of the subject.

There is yet additionally provided, in accordance with a preferred embodiment of the present invention, a system for diagnosing Alzheimer's disease (AD), including a stimulator for stimulating a sphenopalatine ganglion (SPG) of a subject, so that molecular passage increases between cerebrospinal fluid (CSF) of the subject and a tissue of the subject.

There is therefore provided, in accordance with an embodiment of the present invention, a method for treating Alzheimer's disease (AD), including:
stimulating sphenopalatine ganglion (SPG)-related tissue of a subject by applying an electrical signal to the SPG-related tissue, the SPG-related tissue selected from: an SPG of the subject and nerve fibers of the subject which are directly anatomically connected to the SPG; and configuring the stimulation so as to cause an increase in clearance of an AD-related constituent of a central nervous system (CNS) of the subject, from a brain of the subject to a systemic blood circulation of the subject, so as to treat the AD.

There is further provided, in accordance with an embodiment of the present invention, a method for treating Alzheimer's disease (AD), including:

stimulating sphenopalatine ganglion (SPG)-related tissue of a subject by presenting an odorant to an air passage of the subject, the SPG-related tissue selected from: an SPG of the subject and nerve fibers of the subject which are directly anatomically connected to the SPG; and configuring the stimulation so as to cause an increase in clearance of an AD-related constituent of a central nervous system (CNS) of the subject, from a brain of the subject to a systemic blood circulation of the subject, so as to treat the AD.

There is still further provided, in accordance with an embodiment of the present invention, a method for treating Alzheimer's disease (AD), including:

stimulating sphenopalatine ganglion (SPG)-related tissue of a subject by applying an electrical signal to the SPG-related tissue, the SPG-related tissue selected from: an SPG of the subject and nerve fibers of the subject which are directly anatomically connected to the SPG; and configuring the stimulation so as to cause an increase in clearance of an AD-related constituent of a central nervous system (CNS) of the subject, from cerebrospinal fluid (CSF) of the subject to a systemic blood circulation of the subject, so as to treat the AD.

There is yet further provided, in accordance with an embodiment of the present invention, a method for treating Alzheimer's disease (AD), including:

stimulating sphenopalatine ganglion (SPG)-related tissue of a subject by presenting an odorant to an air passage of the subject, the SPG-related tissue selected from: an SPG of the subject and nerve fibers of the subject which are directly anatomically connected to the SPG; and configuring the stimulation so as to cause an increase in clearance of an AD-related constituent of a central nervous system (CNS) of the subject, from cerebrospinal fluid (CSF) of the subject to a systemic blood circulation of the subject, so as to treat the AD.

In an embodiment, stimulating the SPG-related tissue includes directly stimulating the SPG.

For some applications, the AD-related constituent includes an inflammatory-related constituent, tau protein, PS1, PS2, a DNA fragment, an RNA fragment, a cytokine, a marker of neuronal death or degeneration, a marker of an inflammatory process, a neurotoxic substance, amyloid protein, an amyloid protein selected from the list consisting of: wild amyloid protein and mutated amyloid protein, and/or an amyloid protein selected from the list consisting of: fragmented amyloid protein and whole amyloid protein, and configuring the stimulation includes configuring the stimulation so as to cause the increase in the clearance of the inflammatory-related constituent, tau protein, PS1, PS2, DNA fragment, RNA fragment, cytokine, marker of neuronal death or degeneration, marker of an inflammatory process, neurotoxic substance, amyloid protein, amyloid protein selected from the list consisting of wild amyloid protein and mutated amyloid protein, and/or amyloid protein selected from the list consisting of: fragmented amyloid protein and whole amyloid protein.

There is also provided, in accordance with an embodiment of the present invention, a method for treating Alzheimer's disease (AD), including:

supplying a pharmaceutical agent to a systemic blood circulation of a subject;

stimulating sphenopalatine ganglion (SPG)-related tissue of the subject by applying an electrical signal to the SPG-related tissue, the SPG-related tissue selected from: an SPG of the subject and nerve fibers of the subject which are directly anatomically connected to the SPG; and configuring the stimulation so as to cause an increase in passage of the pharmaceutical agent from the systemic blood circulation into a central nervous system (CNS) of the subject, so as to treat the AD.

There is additionally provided, in accordance with an embodiment of the present invention, a method for treating Alzheimer's disease (AD), including:

supplying a pharmaceutical agent to a systemic blood circulation of a subject;

stimulating sphenopalatine ganglion (SPG)-related tissue of the subject by presenting an odorant to an air passage of the subject, the SPG-related tissue selected from: an SPG of the subject and nerve fibers of the subject which are directly anatomically connected to the SPG; and configuring the stimulation so as to cause an increase in passage of the pharmaceutical agent from the systemic blood circulation into a central nervous system (CNS) of the subject, so as to treat the AD.

In an embodiment, supplying the pharmaceutical agent includes administering the pharmaceutical agent to the systemic blood circulation using a technique selected from the list consisting of: per-oral administration, intravenous administration, intra-arterial administration, intraperitoneal administration, subcutaneous administration, and intramuscular administration.

For some applications, the pharmaceutical agent includes a glutamate receptor antagonist, an NMDA receptor blocker, an agent having an inhibitory effect on derivation of β-amyloid from amyloid precursor protein, a cholinesterase inhibitor, a stimulant of nerve regeneration, a nerve growth factor, a compound that stimulates production of nerve growth factor, a microglial activation modulator, an antioxidant, a hormone, an inhibitor of protein tyrosine phosphatases, a medium chain triglyceride, a gene therapy agent, a β-amyloid inhibitor, an endogenous protein, an anti-inflammatory agent, a non-steroidal anti-inflammatory drug (NSAID), or a pharmaceutical agent selected from the list consisting of: an AD vaccine, a component of an AD vaccine, and a derivative of an AD vaccine (for example, the selected pharmaceutical agent including (a) an anti-inflammatory drug, (b) antibodies against a specific protein that is characteristic of AD, (c) antibodies against β-amyloid, or (d) antibodies against tau protein), and configuring the stimulation includes configuring the stimulation so as to cause the increase in the passage of the pharmaceutical agent.

In an embodiment, supplying the pharmaceutical agent includes administering the pharmaceutical agent for inhalation by the subject. For example, administering the pharmaceutical agent for inhalation by the subject may include administering the pharmaceutical agent mixed with the odorant.

There is still additionally provided, in accordance with an embodiment of the present invention, a method for treating Alzheimer's disease (AD), including:

stimulating sphenopalatine ganglion (SPG)related tissue of the subject by applying an electrical signal to the SPG-related tissue, the SPG-related tissue selected from: an SPG of the subject and nerve fibers of the subject which are directly anatomically connected to the SPG; and configuring the stimulation so as to cause an increase in cerebral blood flow (CBF) of the subject, so as to treat the AD.

There is yet additionally provided, in accordance with an embodiment of the present invention, a method for treating Alzheimer's disease (AD), including:

stimulating sphenopalatine ganglion (SPG)-related tissue of the subject by presenting an odorant to an air passage of the subject, the SPG-related tissue selected from: an SPG of the subject and nerve fibers of the subject which are directly anatomically connected to the SPG; and configuring the stimulation so as to cause an increase in cerebral blood flow (CBF) of the subject, so as to treat the AD.

In an embodiment, configuring the stimulation includes configuring the stimulation so as to cause an improvement in a metabolic state of a central nervous system (CNS) of the subject.

There is also provided, in accordance with an embodiment of the present invention, a method for diagnosing Alzheimer's disease (AD), including:

stimulating sphenopalatine ganglion (SPG)-related tissue of a subject by applying an electrical signal to the SPG-related tissue, the SPG-related tissue selected from an SPG of the subject and nerve fibers of the subject which are directly anatomically connected to the SPG; and configuring the stimulation so as to cause an increase in molecular passage between a central nervous system (CNS) of the subject and another body compartment of the subject, so as to facilitate a diagnosis of the AD.

There is additionally provided, in accordance with an embodiment of the present invention, a method for diagnosing Alzheimer's disease (AD), including:

stimulating sphenopalatine ganglion (SPG)related tissue of a subject by presenting an odorant to an air passage of the subject, the SPG-related tissue selected from: an SPG of the subject and nerve fibers of the subject which are directly anatomically connected to the SPG; and configuring the stimulation so as to cause an increase in molecular passage between a central nervous system (CNS) of the subject and another body compartment of the subject, so as to facilitate a diagnosis of the AD.

In an embodiment, the method includes measuring a constituent of the other body compartment.

For some applications, the other body compartment includes a systemic blood circulation of the subject, and configuring the stimulation includes configuring the stimulation so as to cause the increase in molecular passage between the CNS and the systemic blood circulation. Alternatively or additionally, the other body compartment includes plasma of the subject, and configuring the stimulation includes configuring the stimulation so as to cause the increase in molecular passage between the CNS and the plasma. Further alternatively or additionally, the other body compartment includes serum of the subject, and configuring the stimulation includes configuring the stimulation so as to cause the increase in molecular passage between the CNS and the serum. Still further alternatively or additionally, the other body compartment is ascites of the subject, and configuring the stimulation includes configuring the stimulation so as to cause the increase in molecular passage between the CNS and the ascites.

There is yet additionally provided, in accordance with an embodiment of the present invention, a method for diagnosing Alzheimer's disease (AD), including:

stimulating sphenopalatine ganglion (SPG)related tissue of a subject by applying an electrical signal to the SPG-related tissue, the SPG-related tissue selected from: an SPG of the subject and nerve fibers of the subject which are directly anatomically connected to the SPG; and configuring the stimulation so as to cause an increase in molecular passage between cerebrospinal fluid (CSF) of the subject and another body fluid of the subject, so as to facilitate a diagnosis of the AD.

There is still additionally provided, in accordance with an embodiment of the present invention, a method for diagnosing Alzheimer's disease (AD), including:

stimulating sphenopalatine ganglion (SPG)-related tissue of a subject by presenting an odorant to an air passage of the subject, the SPG-related tissue selected from: an SPG of the subject and nerve fibers of the subject which are directly anatomically connected to the SPG; and configuring the stimulation so as to cause an increase in molecular passage between cerebrospinal fluid (CSF) of the subject and another body fluid of the subject, so as to facilitate a diagnosis of the AD.

In an embodiment, the method includes measuring a constituent of the other body fluid.

In an embodiment, the method includes correlating an abnormal concentration of the constituent to a pathology of AD.

For some applications, the constituent is selected from the group consisting of: a protein, a hormone, an antibody, an electrolyte, a neuropeptide, and an enzyme, and measuring the constituent includes measuring the selected constituent Alternatively or additionally, the other body fluid is selected from the list consisting of: whole blood, plasma, serum, and ascites, and measuring the constituent includes sampling the selected fluid.

Measuring the constituent typically includes extracting the other body fluid from tissue of the subject, and, for some applications, measuring a plurality of constituents. In an embodiment, the method includes determining a diagnostic result according to the interrelation between concentrations of the constituents.

There is also provided, in accordance with an embodiment of the present invention, a method for diagnosing Alzheimer's disease (AD), including:

stimulating sphenopalatine ganglion (SPG)-related tissue of a subject by applying an electrical signal to the SPG-related tissue, the SPG-related tissue selected from: an SPG of the subject and nerve fibers of the subject which are directly anatomically connected to the SPG; and configuring the stimulation so as to cause an increase in molecular passage between cerebrospinal fluid (CSF) of the subject and a tissue of the subject, so as to facilitate a diagnosis of the AD.

There is further provided, in accordance with an embodiment of the present invention, a method for diagnosing Alzheimer's disease (AD), including:

stimulating sphenopalatine ganglion (SPG)-related tissue of a subject by presenting an odorant to an air passage of the subject, the SPG-related tissue selected from: an SPG of the subject and nerve fibers of the subject which are directly anatomically connected to the SPG; and configuring the stimulation so as to cause an increase in molecular passage between cerebrospinal fluid (CSF) of the subject and a tissue of the subject, so as to facilitate a diagnosis of the AD.

For some applications, the method includes measuring a constituent of the tissue and/or correlating an abnormal concentration of the constituent to a pathology of AD.

In accordance with an embodiment of the present invention, the constituent is selected from the group consisting of:

a protein, a hormone, an antibody, an electrolyte, a neuropeptide, and an enzyme, and measuring the constituent includes measuring the selected constituent.

In an embodiment, measuring the constituent includes measuring a plurality of constituents of the tissue. In this case, for some applications, the method includes determining a diagnostic result according to the interrelation between concentrations of the constituents of the tissue.

There is still further provided, in accordance with an embodiment of the present invention, a method for treating Alzheimer's disease (AD), including:

applying an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject; and configuring the signal so as to cause an increase in clearance of an AD-related constituent of a central nervous system (CNS) of the subject, from a brain of the subject to a systemic blood circulation of the subject, so as to treat the AD.

There is yet further provided, in accordance with an embodiment of the present invention, a method for treating Alzheimer's disease (AD), including presenting an odorant to an air passage of a subject, the odorant having been selected for presentation to the air passage because it is such as to cause an increase in clearance of an AD-related constituent of a central nervous system (CNS) of the subject from cerebrospinal fluid (CSF) of the subject to a systemic blood circulation of the subject, so as to treat the AD.

There is also provided, in accordance with an embodiment of the present invention, a method for treating Alzheimer's disease (AD), including:

supplying a pharmaceutical agent to a systemic blood circulation of a subject;

applying an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject; and configuring the signal so as to cause an increase in passage of the pharmaceutical agent from the systemic blood circulation into a central nervous system (CNS) of the subject, so as to treat the AD.

There is additionally provided, in accordance with an embodiment of the present invention, a method for treating Alzheimer's disease (AD), including:

supplying a pharmaceutical agent to a systemic blood circulation of a subject; and presenting an odorant to an air passage of the subject, the odorant having been selected for presentation to the air passage because it is such as to cause an increase in passage of the pharmaceutical agent from the systemic blood circulation into a central nervous system (CNS) of the subject, so as to treat the AD.

There is still additionally provided, in accordance with an embodiment of the present invention, a method for treating Alzheimer's disease (AD), including:

applying an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject; and configuring the signal so as to cause an increase in cerebral blood flow (CBF) of the subject, so as to treat the AD.

There is yet additionally provided, in accordance with an embodiment of the present invention, a method for treating Alzheimer's disease (AD), including presenting an odorant to an air passage of the subject, the odorant having been selected for presentation to the air passage because it is such as to cause an increase in cerebral blood flow (CBF) of the subject, so as to treat the AD.

There is also provided, in accordance with an embodiment of the present invention, a method for diagnosing Alzheimer's disease (AD), including:

applying an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject; and configuring the signal so as to cause an increase in molecular passage between a central nervous system (CNS) of the subject and another body compartment of the subject, so as to facilitate a diagnosis of the AD.

There is further provided, in accordance with an embodiment of the present invention, a method for diagnosing Alzheimer's disease (AD), including presenting an odorant to an air passage of the subject, the odorant having been selected for presentation to the air passage because it is such as to cause an increase in molecular passage between a central nervous system (CNS) of the subject and another body compartment of the subject, so as to facilitate a diagnosis of the AD.

There is still further provided, in accordance with an embodiment of the present invention, a method for diagnosing Alzheimer's disease (AD), including:

applying an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject; and configuring the signal so as to cause an increase in molecular passage between cerebrospinal fluid (CSF) of the subject and another body fluid of the subject, so as to facilitate a diagnosis of the AD.

There is yet further provided, in accordance with an embodiment of the present invention, a method for diagnosing Alzheimer's disease (AD), including presenting an odorant to an air passage of the subject, the odorant having been selected for presentation to the air passage because it is such as to cause an increase in molecular passage between cerebrospinal fluid (CSF) of the subject and another body fluid of the subject, so as to facilitate a diagnosis of the AD.

There is also provided, in accordance with an embodiment of the present invention, a method for diagnosing Alzheimer's disease (AD), including:

applying an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject; and configuring the signal so as to cause an increase in molecular passage between cerebrospinal fluid (CSF) of the subject and a tissue of the subject, so as to facilitate a diagnosis of the AD.

There is additionally provided, in accordance with an embodiment of the present invention, a method for diagnosing Alzheimer's disease (AD), including presenting an odorant to an air passage of the subject, the odorant having been selected for presentation to the air passage because it is such as to cause an increase in molecular passage between cerebrospinal fluid (CSF) of the subject and a tissue of the subject, so as to facilitate a diagnosis of the AD.

In an embodiment, the method includes presenting in association with the odorant an analgesic in a dosage configured to reduce a sensation associated with the presenting of the odorant. For some applications, the air passage includes a nasal cavity or a throat of the patient, and presenting the odorant includes presenting the odorant to the nasal cavity or the throat.

For some applications, the odorant is selected from the list consisting of: propionic acid, cyclohexanone, and amyl acetate, and presenting the odorant includes presenting the selected odorant.

Alternatively or additionally, the odorant is selected from the list consisting of: acetic acid, citric acid, carbon dioxide, sodium chloride, and ammonia, and presenting the odorant includes presenting the selected odorant.

Further alternatively or additionally, the odorant is selected from the list consisting of: menthol, alcohol nicotine, piperine, gingerol, zingerone, allyl isothiocyanate, cinnamaldehyde, cuminaldehyde, 2-propenyl/2-phenylethyl isothiocyanate, thymol, and eucalyptol, and presenting the odorant includes presenting the selected odorant.

In an embodiment, presenting the odorant includes presenting a capsule for placement within a mouth of the patient, the capsule being configured to dissolve upon contact with salivary liquids of the patient, whereupon the odorant is presented to the air passage.

There is yet additionally provided, in accordance with an embodiment of the present invention, apparatus for treating Alzheimer's disease (AD), including a stimulator adapted to:

stimulate sphenopalatine ganglion (SPG)-related tissue of a subject by applying an electrical signal to the SPG-related tissue, the SPG-related tissue selected from: an SPG of the subject and nerve fibers of the subject which are directly anatomically connected to the SPG, and configure the stimulation so as to cause an increase in clearance of an AD-related constituent of a central nervous system (CNS) of the subject, from a brain of the subject to a systemic blood circulation of the subject, so as to treat the AD.

There is still additionally provided, in accordance with an embodiment of the present invention, apparatus for treating Alzheimer's disease (AD), including a stimulator adapted to:

stimulate sphenopalatine ganglion (SPG)-related tissue of a subject by presenting an odorant to an air passage of the subject, the SPG-related tissue selected from: an SPG of the subject and nerve fibers of the subject which are directly anatomically connected to the SPG, and configure the stimulation so as to cause an increase in clearance of an AD-related constituent of a central nervous system (CNS) of the subject, from a brain of the subject to a systemic blood circulation of the subject, so as to treat the AD.

There is also provided, in accordance with an embodiment of the present invention, apparatus for treating Alzheimer's disease (AD), including a stimulator adapted to:

stimulate sphenopalatine ganglion (SPG)related tissue of a subject by applying an electrical signal to the SPG-related tissue, the SPG-related tissue selected from: an SPG of the subject and nerve fibers of the subject which are directly anatomically connected to the SPG, and configure the stimulation so as to cause an increase in clearance of an AD-related constituent of a central nervous system (CNS) of the subject, from cerebrospinal fluid (CSF) of the subject to a systemic blood circulation of the subject, so as to treat the AD.

There is further provided, in accordance with an embodiment of the present invention, apparatus for treating Alzheimer's disease (AD), including a stimulator adapted to:

stimulate sphenopalatine ganglion (SPG)related tissue of a subject by presenting an odorant to an air passage of the subject, the SPG-related tissue selected from: an SPG of the subject and nerve fibers of the subject which are directly anatomically connected to the SPG, and configure the stimulation so as to cause an increase in clearance of an AD-related constituent of a central nervous system (CNS) of the subject, from cerebrospinal fluid (CSF) of the subject to a systemic blood circulation of the subject, so as to treat the AD.

In an embodiment, the stimulator is adapted to directly stimulate the SPG.

There is still further provided, in accordance with an embodiment of the present invention, apparatus for treating Alzheimer's disease (AD), including a stimulator adapted to:

stimulate sphenopalatine ganglion (SPG)related tissue of the subject by applying an electrical signal to the SPG-related tissue, the SPG-related tissue selected from: an SPG of the subject and nerve fibers of the subject which are directly anatomically connected to the SPG, and configure the stimulation so as to cause an increase in passage from a systemic blood circulation of the subject into a central nervous system (CNS) of the subject, of a pharmaceutical agent supplied to the systemic blood circulation, so as to treat the AD.

There is yet further provided, in accordance with an embodiment of the present invention, apparatus for treating Alzheimer's disease (AD), including a stimulator adapted to:

stimulate sphenopalatine ganglion (SPG)-related tissue of the subject by presenting an odorant to an air passage of the subject, the SPG-related tissue selected from: an SPG of the subject and nerve fibers of the subject which are directly anatomically connected to the SPG, and configure the stimulation so as to cause an increase in passage from a systemic blood circulation of the subject into a central nervous system (CNS) of the subject, of a pharmaceutical agent supplied to the systemic blood circulation, so as to treat the AD.

There is also provided, in accordance with an embodiment of the present invention, apparatus for treating Alzheimer's disease (AD), including a stimulator adapted to:

stimulate sphenopalatine ganglion (SPG)related tissue of the subject by applying an electrical signal to the SPG-related tissue, the SPG-related tissue selected from: an SPG of the subject and nerve fibers of the subject which are directly anatomically connected to the SPG, and configure the stimulation so as to cause an increase in cerebral blood flow (CBF) of the subject, so as to treat the AD.

There is additionally provided, in accordance with an embodiment of the present invention, apparatus for treating Alzheimer's disease (AD), including a stimulator adapted to:

stimulate sphenopalatine ganglion (SPG)-related tissue of the subject by presenting an odorant to an air passage of the subject, the SPG-related tissue selected from: an SPG of the subject and nerve fibers of the subject which are directly anatomically connected to the SPG, and configure the stimulation so as to cause an increase in cerebral blood flow (CBF) of the subject, so as to treat the AD.

There is still additionally provided, in accordance with an embodiment of the present invention, apparatus for diagnosing Alzheimer's disease (AD), including a stimulator adapted to:

stimulate sphenopalatine ganglion (SPG)related tissue of a subject by applying an electrical signal to the SPG-related tissue, the SPG-related tissue selected from: an SPG of the subject and nerve fibers of the subject which are directly anatomically connected to the SPG, and configure the stimulation so as to cause an increase in molecular passage between a central nervous system (CNS) of the subject and another body compartment of the subject, so as to facilitate a diagnosis of the AD.

There is yet additionally provided, in accordance with an embodiment of the present invention, apparatus for diagnosing Alzheimer's disease (AD), including a stimulator adapted to:

stimulate sphenopalatine ganglion (SPG)related tissue of a subject by presenting an odorant to an air passage of the subject, the SPG-related tissue selected from: an SPG of the subject and nerve fibers of the subject which are directly anatomically connected to the SPG, and configure the stimulation so as to cause an increase in molecular passage between a central nervous system (CNS) of the subject and another body compartment of the subject, so as to facilitate a diagnosis of the AD.

There is also provided, in accordance with an embodiment of the present invention, apparatus for diagnosing Alzheimer's disease (AD), including a stimulator adapted to:

stimulate sphenopalatine ganglion (SPG)related tissue of a subject by applying an electrical signal to the SPG-related tissue, the SPG-related tissue selected from: an SPG of the subject and nerve fibers of the subject which are directly anatomically connected to the SPG, and configure the stimulation so as to cause an increase in molecular passage between cerebrospinal fluid (CSF) of the subject and another body fluid of the subject, so as to facilitate a diagnosis of the AD.

There is further provided, in accordance with an embodiment of the present invention, apparatus for diagnosing Alzheimer's disease (AD), including a stimulator adapted to:

stimulate sphenopalatine ganglion (SPG)-related tissue of a subject by presenting an odorant to an air passage of the subject, the SPG-related tissue selected from: an SPG of the subject and nerve fibers of the subject which are directly anatomically connected to the SPG, and configure the stimulation so as to cause an increase in molecular passage between cerebrospinal fluid (CSF) of the subject and another body fluid of the subject, so as to facilitate a diagnosis of the AD.

There is still further provided, in accordance with an embodiment of the present invention, apparatus for diagnosing Alzheimer's disease (AD), including a stimulator adapted to:

stimulate sphenopalatine ganglion (SPG)-related tissue of a subject by applying an electrical signal to the SPG-related tissue, the SPG-related tissue selected from: an SPG of the subject and nerve fibers of the subject which are directly anatomically connected to the SPG, and configure the stimulation so as to cause an increase in molecular passage between cerebrospinal fluid (CSF) of the subject and a tissue of the subject, so as to facilitate a diagnosis of the AD.

There is yet further provided, in accordance with an embodiment of the present invention, apparatus for diagnosing Alzheimer's disease (AD), including a stimulator adapted to:

stimulate sphenopalatine ganglion (SPG)-related tissue of a subject by presenting an odorant to an air passage of the subject, the SPG-related tissue selected from: an SPG of the subject and nerve fibers of the subject which are directly anatomically connected to the SPG, and configure the stimulation so as to cause an increase in molecular passage between cerebrospinal fluid (CSF) of the subject and a tissue of the subject, so as to facilitate a diagnosis of the AD.

There is also provided, in accordance with an embodiment of the present invention, apparatus for treating Alzheimer's disease (AD), including a stimulator adapted to:

apply an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject, and configure the signal so as to cause an increase in clearance of an AD-related constituent of a central nervous system (CNS) of the subject, from a brain of the subject to a systemic blood circulation of the subject, so as to treat the AD.

There is also provided, in accordance with an embodiment of the present invention, apparatus for treating Alzheimer's disease (AD), including a stimulator adapted to present an odorant to an air passage of a subject, the odorant having been selected for presentation to the air passage because it is such as to cause an increase in clearance of an AD-related constituent of a central nervous system (CNS) of the subject from cerebrospinal fluid (CSF) of the subject to a systemic blood circulation of the subject, so as to treat the AD.

There is additionally provided, in accordance with an embodiment of the present invention, apparatus for treating Alzheimer's disease (AD), including a stimulator adapted to apply an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject, and configure the signal so as to cause an increase in passage from a systemic blood circulation of the subject into a central nervous system (CNS) of the subject, of a pharmaceutical agent supplied to the systemic blood circulation, so as to treat the AD.

There is still additionally provided, in accordance with an embodiment of the present invention, apparatus for treating Alzheimer's disease (AD), including a stimulator adapted to present an odorant to an air passage of the subject, the odorant having been selected for presentation to the air passage because it is such as to cause an increase in passage from a systemic blood circulation of the subject into a central nervous system (CNS) of the subject, of a pharmaceutical agent supplied to the systemic blood circulation, so as to treat the AD.

There is yet additionally provided, in accordance with an embodiment of the present invention, apparatus for treating Alzheimer's disease (AD), including a stimulator adapted to:

apply an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject, and configure the signal so as to cause an increase in cerebral blood flow (CBF) of the subject, so as to treat the AD.

There is also provided, in accordance with an embodiment of the present invention, apparatus for treating Alzheimer's disease (AD), including a stimulator adapted to present an odorant to an air passage of the subject, the odorant having been selected for presentation to the air passage because it is such as to cause an increase in cerebral blood flow (CBF) of the subject, so as to treat the AD.

There is further provided, in accordance with an embodiment of the present invention, apparatus for diagnosing Alzheimer's disease (AD), including a stimulator adapted to:

apply an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject, and configure the signal so as to cause an increase in molecular passage between a central nervous system (CNS) of the subject and another body compartment of the subject, so as to facilitate a diagnosis of the AD.

There is still further provided, in accordance with an embodiment of the present invention, apparatus for diagnosing Alzheimer's disease (AD), including a stimulator adapted to present an odorant to an air passage of the subject, the odorant having been selected for presentation to the air passage because it is such as to cause an increase in molecular passage between a central nervous system (CNS) of the subject and another body compartment of the subject, so as to facilitate a diagnosis of the AD.

There is yet further provided, in accordance with an embodiment of the present invention, apparatus for diagnosing Alzheimer's disease (AD), including a stimulator adapted to:

apply an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject, and configure the signal so as to cause an increase in molecular passage between cerebrospinal fluid (CSF) of the subject and another body fluid of the subject, so as to facilitate a diagnosis of the AD.

There is also provided, in accordance with an embodiment of the present invention, apparatus for diagnosing Alzheimer's disease (AD), including a stimulator adapted to present an odorant to an air passage of the subject, the odorant having been selected for presentation to the air passage because it is such as to cause an increase in molecular passage between cerebrospinal fluid (CSF) of the subject and another body fluid of the subject, so as to facilitate a diagnosis of the AD.

There is additionally provided, in accordance with an embodiment of the present invention, apparatus for diagnosing Alzheimer's disease (AD), including a stimulator adapted to:

apply an electrical signal to at least one site of a subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject, and configure the signal so as to cause an increase in molecular passage between cerebrospinal fluid (CSF) of the subject and a tissue of the subject, so as to facilitate a diagnosis of the AD.

There is still additionally provided, in accordance with an embodiment of the present invention, apparatus for diagnosing Alzheimer's disease (AD), including a stimulator adapted to present an odorant to an air passage of the subject, the odorant having been selected for presentation to the air passage because it is such as to cause an increase in molecular passage between cerebrospinal fluid (CSF) of the subject and a tissue of the subject, so as to facilitate a diagnosis of the AD.

There is yet additionally provided, in accordance with an embodiment of the present invention, apparatus for treating Alzheimer's disease (AD), including:

an odorant-storage vessel;

an odorant for storage within the odorant-storage vessel, the odorant being capable of increasing clearance of an AD-related constituent of a central nervous system (CNS) of the subject from cerebrospinal fluid (CSF) of the subject to a systemic blood circulation of the subject; and an odorant-delivery element, adapted to present the odorant to an air passage of the patient, so as to treat the AD.

There is also provided, in accordance with an embodiment of the present invention, apparatus for treating Alzheimer's disease (AD), including:

an odorant-storage vessel;

an odorant for storage within the odorant-storage vessel, the odorant being capable of increasing passage, from a systemic blood circulation of a subject into a central nervous system (CNS) of the subject, of a pharmaceutical agent supplied to the systemic blood circulation; and an odorant-delivery element, adapted to present the odorant to an air passage of the patient, so as to treat the AD.

There is further provided, in accordance with an embodiment of the present invention, apparatus for treating Alzheimer's disease (AD), including:

an odorant-storage vessel;

an odorant for storage within the odorant-storage vessel, the odorant being capable of increasing cerebral blood flow (CBF) of the subject; and an odorant-delivery element, adapted to present the odorant to an air passage of the patient, so as to treat the AD.

There is still further provided, in accordance with an embodiment of the present invention, apparatus for diagnosing Alzheimer's disease (AD), including:

an odorant-storage vessel;

an odorant for storage within the odorant-storage vessel, the odorant being capable of increasing molecular passage between a central nervous system (CNS) of the subject and another body compartment of the subject; and an odorant-delivery element, adapted to present the odorant to an air passage of the patient, so as to facilitate a diagnosis of the AD.

There is yet further provided, in accordance with an embodiment of the present invention, apparatus for diagnosing Alzheimer's disease (AD), including:

an odorant-storage vessel;

an odorant for storage within the odorant-storage vessel, the odorant being capable of increasing molecular passage between cerebrospinal fluid (CSF) of the subject and another body fluid of the subject; and an odorant-delivery element, adapted to present the odorant to an air passage of the patient, so as to facilitate a diagnosis of the AD.

There is also provided, in accordance with an embodiment of the present invention, apparatus for diagnosing Alzheimer's disease (AD), including:

an odorant-storage vessel;

an odorant for storage within the odorant-storage vessel, the odorant being capable of increasing molecular passage between cerebrospinal fluid (CSF) of the subject and a tissue of the subject; and an odorant-delivery element, adapted to present the odorant to an air passage of the patient, so as to facilitate a diagnosis of the AD.

In an embodiment, the odorant-storage vessel in combination with the odorant-delivery element includes an aqueous spray nasal inhaler.

In an embodiment, the odorant-storage vessel in combination with the odorant-delivery element includes a metered dose nasal inhaler.

In an embodiment, the odorant-storage vessel in combination with the odorant-delivery element includes an air-dilution olfactometer.

The present invention will be more fully understood from the following detailed description of preferred embodiments thereof taken together with the drawings, in which:

BRIEF DESCRIPTION OF THE DRAWINGS

FIGS. 9, 10A, and 10B are schematic diagrams illustrating further circuitry for use with implantable stimulators, in accordance with respective preferred embodiments of the present invention;

FIGS. 15-17 are graph showing the results from SPG stimulation experiments carried out in accordance with embodiments of the present invention.

DETAILED DESCRIPTION OF PREFERRED EMBODIMENTS

Figure 1:
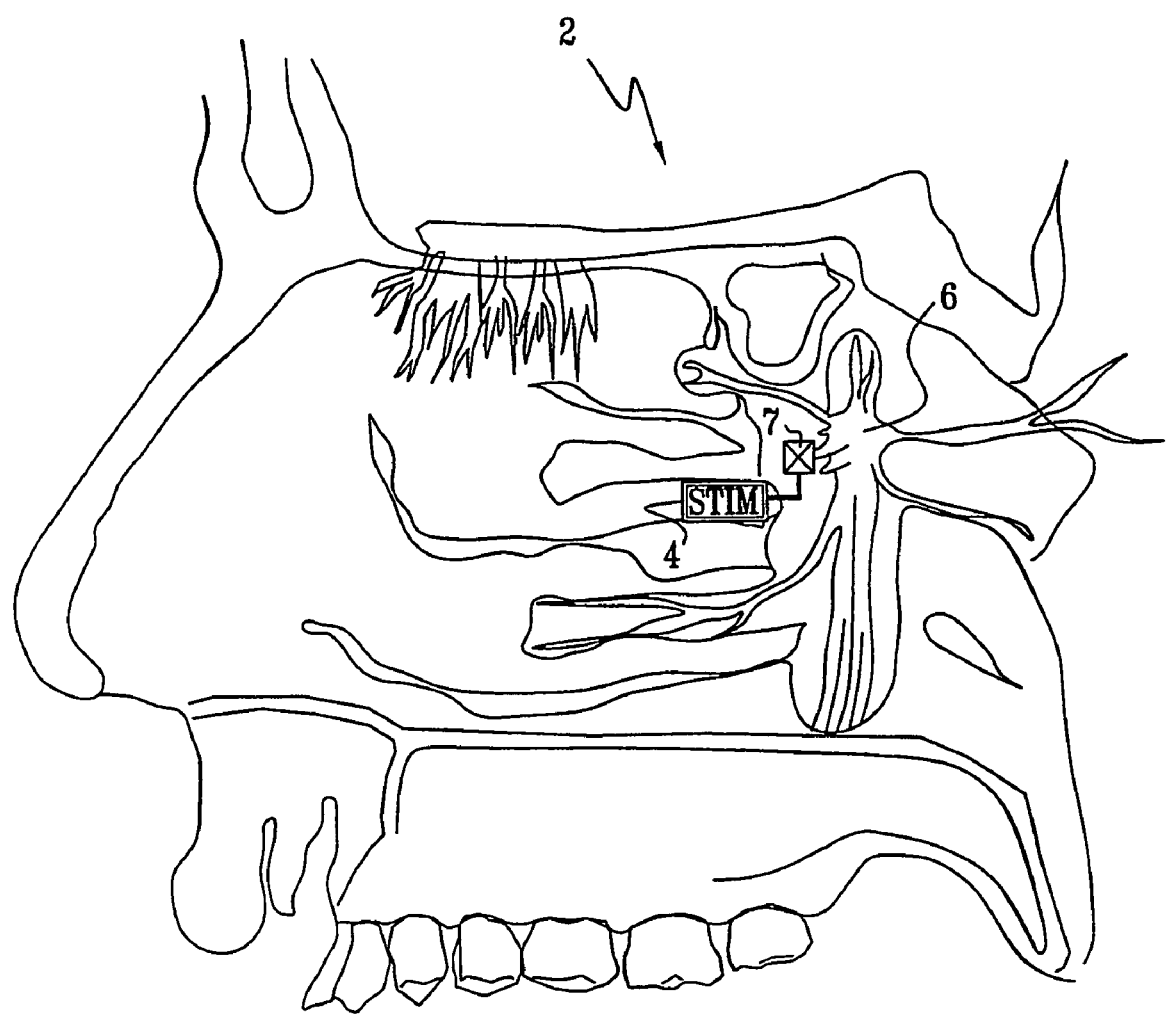
FIG. 1 is a schematic pictorial view of a fully implantable stimulator for stimulation of the SPG, in accordance with a preferred embodiments of the present invention.

FIG. 1 is a schematic pictorial view of a fully-implantable stimulator 4, for stimulation of the sphenopalatine ganglion (SPG) 6 or other parasympathetic site of a patient, in accordance with a preferred embodiments of the present invention. In FIG. 1, a human nasal cavity 2 is shown, and stimulator 4 is implanted adjacent to SPG 6. Branches of parasympathetic neurons coming from SPG 6 extend to the middle cerebral and anterior cerebral arteries (not shown). Preferably, one or more relatively short electrodes 7 extend from stimulator 4 to contact or to be in a vicinity of SPG 6 or of nerves innervating SPG 6 (e.g., postganglionic parasympathetic trunks thereof).

For some applications, stimulator 4 is implanted on top of the bony palate, in the bottom of the nasal cavity. Alternatively or additionally, the stimulator is implanted at the lower side of the bony palate, at the top of the oral cavity. In this instance, one or more flexible electrodes 7 originating in the stimulator are passed through the palatine bone or posterior to the soft palate, so as to be in a position to stimulate the SPG or its parasympathetic tracts. Further alternatively or additionally, the stimulator may be directly attached to the SPG and/or to its postganglionic parasympathetic trunk(s).

For some applications, stimulator 4 is delivered to a desired point within nasal cavity 2 by removably attaching stimulator 4 to the distal end of a rigid or slightly flexible introducer rod (not shown) and inserting the rod into one of the patients nasal passages until the stimulator is properly positioned. As appropriate, the placement process may be facilitated by fluoroscopy, x-ray guidance, fine endoscopic surgery (FES) techniques or by any other effective guidance method known in the art, or by combinations of the aforementioned. Preferably, the ambient temperature and/or cerebral blood flow is measured concurrently with insertion. The cerebral blood flow may be measured with, for example, a laser Doppler unit positioned at the patient's forehead or transcranial Doppler measurements. Verification of proper implantation of the electrodes onto the appropriate neural structure may be performed by activating the device, and generally simultaneously monitoring cerebral blood flow.

The passage of certain molecules from cerebral blood vessels into the brain is hindered by the BBB. The endothelium of the capillaries, the plasma membrane of the blood vessels, and the foot processes of the astrocytes all impede uptake by the brain of the molecules. The BBB generally allows only small molecules (e.g., hydrophilic molecules of molecular weight less than about 200 Da, and lipophilic molecules of less than about 500 Da) to pass from the circulation into the brain.

In accordance with a preferred embodiment of the present invention, parasympathetic activation induced by current from stimulator 4 overcomes the resistance to trans-BBB molecular movement generated by the endothelium of the cerebral capillaries and the plasma membrane. For some applications, therefore, stimulator 4 may be used to transiently remove a substantial obstacle to the passage of drugs from the blood to the brain. For example, the stimulator may cyclically apply current for about two minutes, and subsequently have a rest period of between about 1 and 20 minutes.

It is hypothesized that two neurotransmitters play an important role in this change in properties of the BBB—vasoactive intestinal polypeptide (VIP) and nitric oxide (NO). (Acetylcholine may also be involved.) VIP is a short peptide, and NO is a gaseous molecule. VIP is believed to be a major factor in facilitating plasma protein extravasation (PPE), while NO is responsible for vasodilation. For some applications, stimulator 4 is adapted to vary parameters of the current applied to the SPG, as appropriate, in order to selectively influence the activity of one or both of these neurotransmitters. For example, stimulation of the parasympathetic nerve at different frequencies can induce differential secretion—low frequencies cause secretion of NO, while high frequencies (e.g., above about 10 Hz) cause secretion of peptides (VIP).

For other applications, a constant level DC signal, or a slowly varying voltage ramp is applied, in order to block parasympathetic neural activity in affected tissue. Alternatively, similar results can be obtained by stimulating at a rate higher than about 10 Hz, because this tends to exhaust neurotransmitters. Thus, stimulator 4 may be configured to induce parasympathetic electrical block, in order to cause vasoconstriction by mimicking the overall effect of chemical block on the SPG. This vasoconstrictive effect may be used, for example, to controllable prevent or reverse the formation of migraine headaches. This technique of electrical treatment of migraines stands in contrast to methods of the prior art, in which pharmacological agents such as lidocaine are used to induce SPG block.

Figure 2:
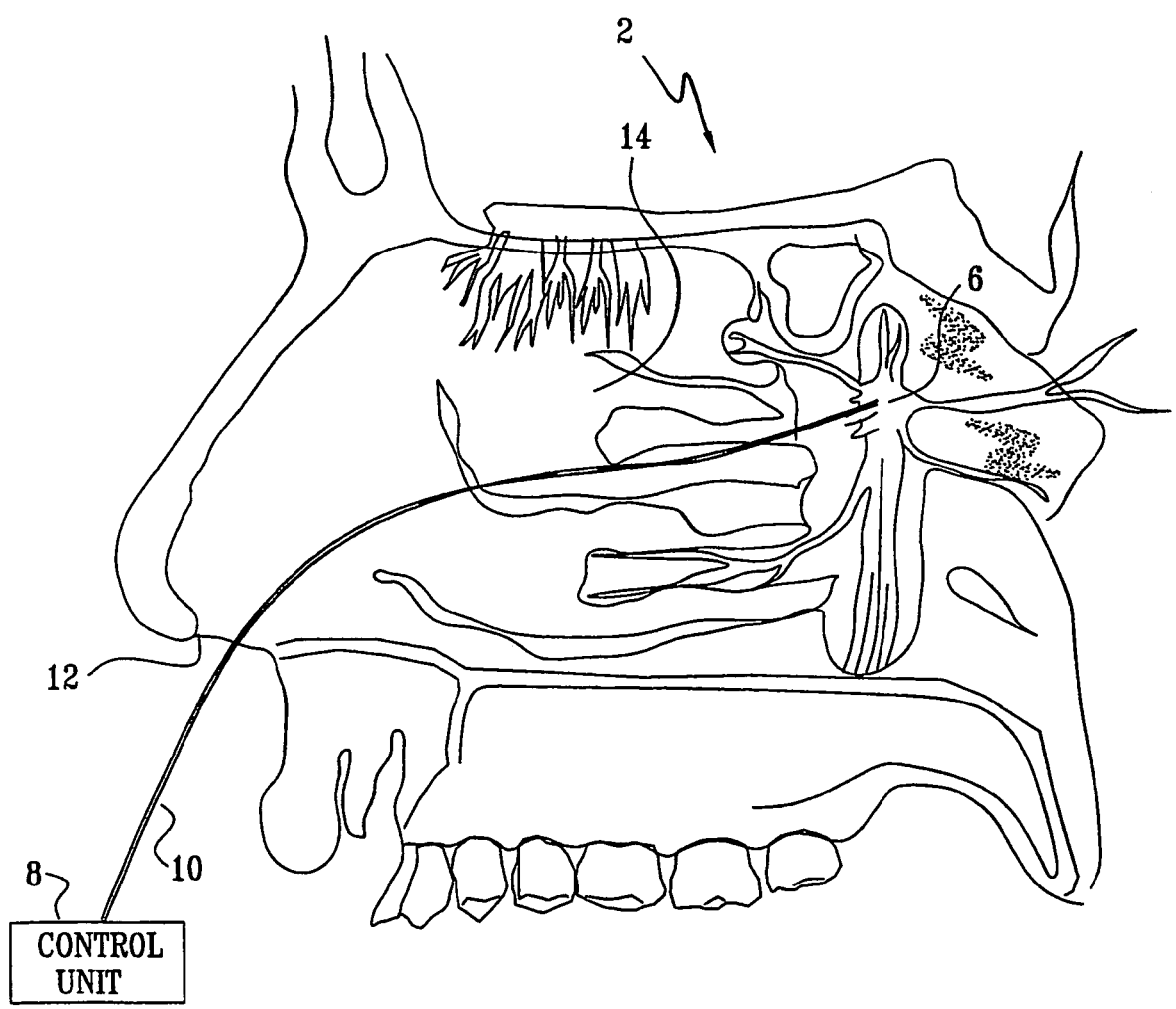
FIG. 2 is a schematic pictorial view of another stimulator for stimulation of the SPG, in accordance with a preferred embodiment of the present invention.

FIG. 2 is a schematic illustration of a stimulator control unit 8 positioned external to a patient's body, in accordance with a preferred embodiment of the present invention. At least one flexible electrode 10 preferably extends from control unit 8, through a nostril 12 of the patient, and to a position within the nasal cavity 14 that is adjacent to SPG 6.

It is to be understood that electrodes 7 (FIG. 1) and 10 may each comprise one or more electrodes, e.g., two electrodes, or an array of microelectrodes. For applications in which stimulator 4 comprises a metal housing that can function as an electrode, then typically one electrode 7 is used, operating in a monopolar mode. Regardless of the total number of electrodes in use, typically only a single or a double electrode extends to SPG 6. Other electrodes 7 or 10 or a metal housing of stimulator 4 are preferably temporarily or permanently implanted in contact with other parts of nasal cavity 2.

Each of electrodes 7 and/or 10 preferably comprises a suitable conductive material, for example, a physiologically-acceptable material such as silver, iridium, platinum, a platinum iridium alloy, titanium, nitinol, or a nickel-chrome alloy. For some applications, one or more of the electrodes have lengths ranging from about 1 to 5 mm, and diameters ranging from about 50 to 100 microns. Each electrode is preferably insulated with a physiologically-acceptable material such as polyethylene, polyurethane, or a co-polymer of either of these. The electrodes are preferably spiral in shape, for better contact, and may have a hook shaped distal end for hooking into or near the SPG. Alternatively or additionally, the electrodes may comprise simple wire electrodes, spring-loaded "crocodile" electrodes, or adhesive probes, as appropriate.

In a preferred embodiment of the invention, each one of electrodes 7 and/or 10 comprises a substantially smooth surface, except that the distal end of each such electrode is configured or treated to have a large surface area. For example, the distal tip may be porous platinized. Alternatively or additionally, at least the tip of electrode 7 or 10, and/or a metal housing of stimulator 4 includes a coating comprising an anti-inflammatory drug, such as beclomethasone sodium phosphate or beclomethasone phosphate. Alternatively, such an anti-inflammatory drug is injected or otherwise applied.

Figure 3:
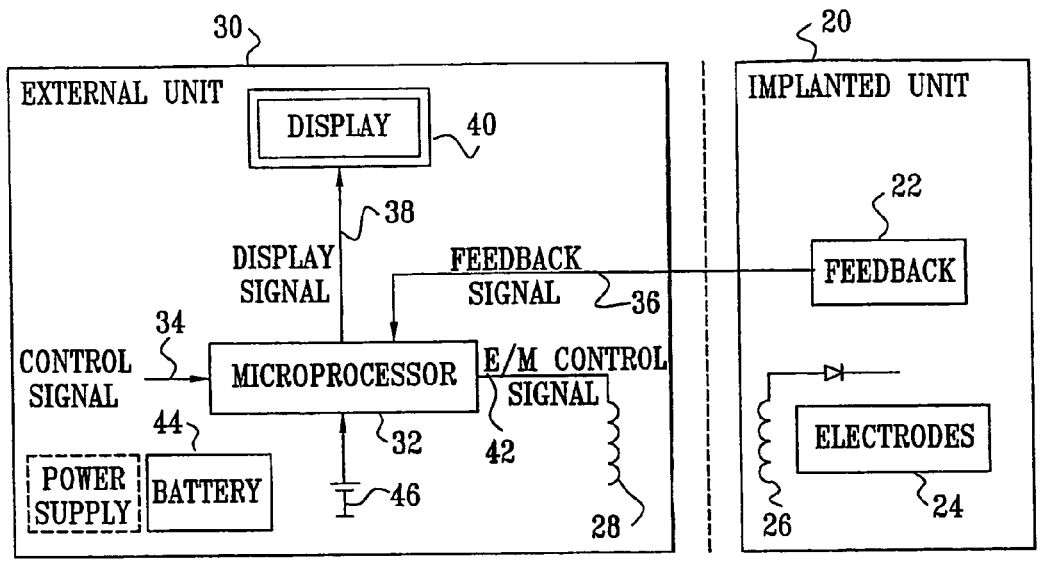
FIG. 3 is a schematic block diagram illustrating circuitry for use with the stimulator shown in FIG. 1, in accordance with a preferred embodiment of the present invention.

FIG. 3 is a schematic block diagram illustrating circuitry comprising an implanted unit 20 and an external unit 30, for use with stimulator 4 (FIG. 1), in accordance with a preferred embodiment of the present invention. Implanted unit 20 preferably comprises a feedback block 22 and one or more sensing or signal application electrodes 24. Implanted unit 20 typically also comprises an electromagnetic coupler 26, which receives power and/or sends or receives data signals to or from an electromagnetic coupler 28 in external unit 30.

External unit 30 preferably comprises a microprocessor 32 which receives an external control signal 34 (e.g., from a physician or from the patient), and a feedback signal 36 from feedback block 22. Control signal 34 may include, for example, operational parameters such as a schedule of operation, patient parameters such as the patient's weight, or signal parameters, such as desired frequencies or amplitudes of a signal to be applied to the SPG. If appropriate, control signal 34 can comprise an emergency override signal, entered by the patient or a healthcare provider to terminate stimulation or to modify it in accordance with a predetermined program. Microprocessor 32, in turn, preferably processes control signal 34 and feedback signal 36 so as to determine one or more parameters of the electric current to be applied through electrodes 24. Responsive to this determination, microprocessor 32 typically generates an electromagnetic control signal 42 that is conveyed by electromagnetic coupler 28 to electromagnetic coupler 26. Control signal 42 preferably corresponds to a desired current or voltage to be applied by electrodes 24 to SPG 6, and, in a preferred embodiment, inductively drives the electrodes. The configuration of couplers 26 and 28 and/or other circuitry in units 20 or 30 may determine the intensity, frequency, shape, monophasic or biphasic mode, or DC offset of the signal (e.g., a series of pulses) applied to designated tissue.

Power for microprocessor 32 is typically supplied by a battery 44 or, optionally, another DC power supply. Grounding is provided by battery 44 or a separate ground 46. If appropriate, microprocessor 32 generates a display signal 38 that drives a display block 40 of external unit 30. Typically, but not necessarily, the display is activated to show feedback data generated by feedback block 22, or to provide a user interface for the external unit.

Implanted unit 20 is preferably packaged in a case made of titanium, platinum or an epoxy or other suitable biocompatible material. Should the case be made of metal, then the case may serve as a ground electrode and, therefore, stimulation typically is performed in a monopolar mode. Alternatively, should the case be made of biocompatible plastic material, two electrodes 24 are typically driven to apply current to the SPG.

For some applications, the waveform applied by one or more of electrodes 24 to designated tissue (e.g., the SPG) comprises a waveform with an exponential decay, a ramp up or down, a square wave, a sinusoid, a saw tooth, a DC component, or any other shape known in the art to be suitable for application to tissue. Alternatively or additionally, the waveform comprises one or more bursts of short shaped or square pulses—each pulse preferably less than about 1 ms in duration. Generally, appropriate waveforms and parameters thereof are determined during an initial test period of external unit 30 and implanted unit 20. For some applications, the waveform is dynamically updated according to measured physiological parameters, measured during a period in which unit 20 is stimulating the SPG, and/or during a non-activation (i.e., standby) period.

Figure 4:
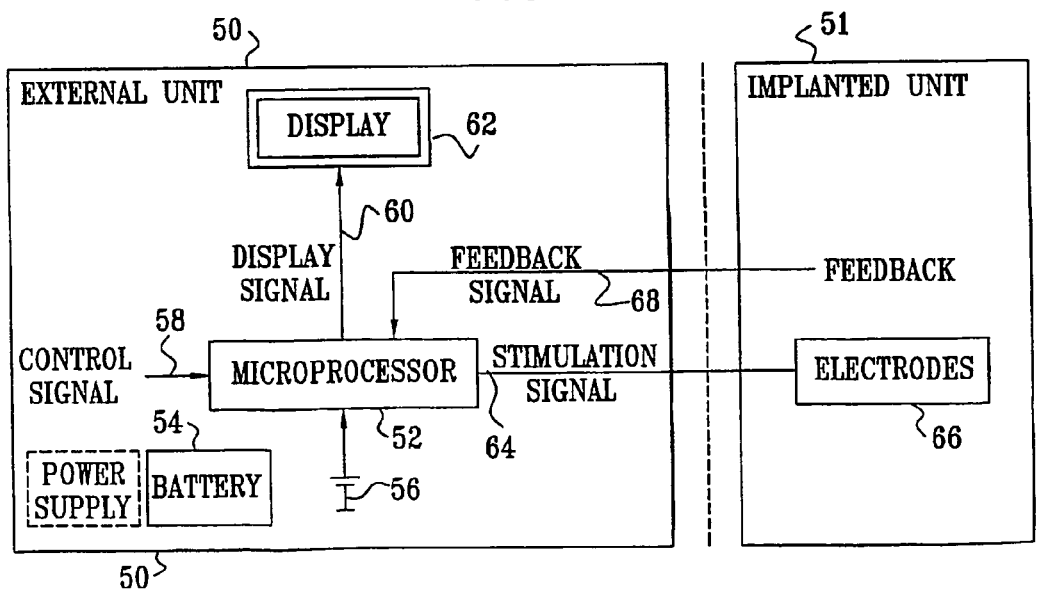
FIG. 4 is a schematic block diagram illustrating circuitry for use with the stimulator shown in FIG. 2, in accordance with a preferred embodiment of the present invention.

FIG. 4 is a schematic block diagram of circuitry for use, for example, in conjunction with control unit 8 (FIG. 2), in accordance with a preferred embodiment of the present invention. An external unit 50 comprises a microprocessor 52 supplied by a battery 54 or another DC power source. Grounding may be provided by battery 54 or by a separate ground 56. Microprocessor 52 preferably receives control and feedback signals 58 and 68 (analogous to signal 34 and 36 described hereinabove), and generates responsive thereto a stimulation signal 64 conveyed by one or more electrodes 66 to the SPG or other tissue. Typically, but not necessarily, feedback signal 68 comprises electrical feedback measured by one or more of electrodes 66 and/or feedback from other sensors on or in the patients brain or elsewhere coupled to the patients body. If appropriate, microprocessor 52 generates a display signal 60 which drives a display block 62 to output relevant data to the patient or the patient's physician. Typically, some or all of electrodes 66 are temporarily implanted in the patient (e.g., following a stroke), and are directly driven by wires connecting the external unit to the implanted unit.

Figure 5A:
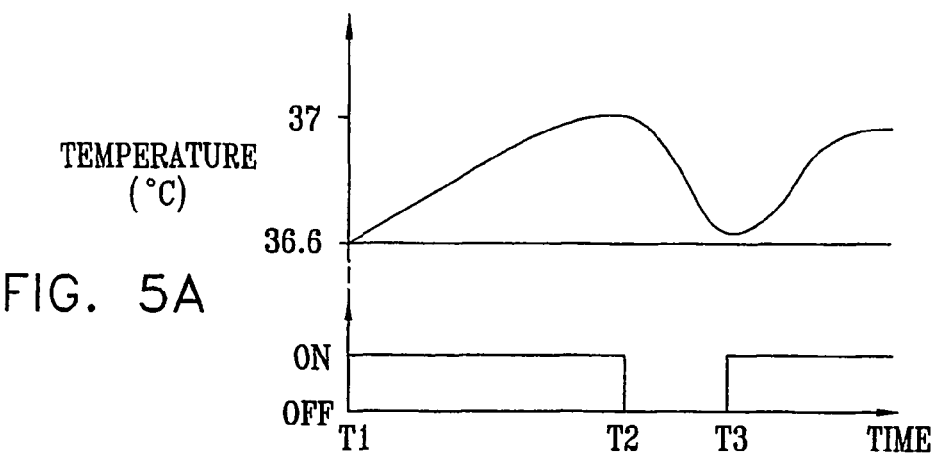
FIGS. 5A and 5B are schematic illustrations depicting different modes of operation of stimulators such as those shown in FIGS. 1 and 2, in accordance with preferred embodiments of the present invention.

FIG. 5A is a graph schematically illustrating a mode of operation of one or more of the devices shown in FIGS. 1-4, in accordance with a preferred embodiment of the present invention. Preferably, the effect of the applied stimulation is monitored by means of a temperature transducer at the SPG or elsewhere in the head, e.g., in the nasal cavity. As shown in FIG. 5A for a step (ON/OFF) mode of stimulation, stimulation of the SPG or related tissue is initiated at a time T1, and this is reflected by a measurable rise in temperature (due to increased blood flow). Once the temperature rises to a predetermined or dynamically-varying threshold (e.g., 37° C.), stimulation is terminated (time T2), responsive to which the temperature falls. As appropriate, when the temperature drops to a designated or dynamically-determined point, the stimulation is reinitiated (time T3). Preferably, suitable temperatures or other physiological parameters are determined for each patient so as to provide the optimal treatment If appropriate, control instructions may also be received from the patient.

Figure 5B:
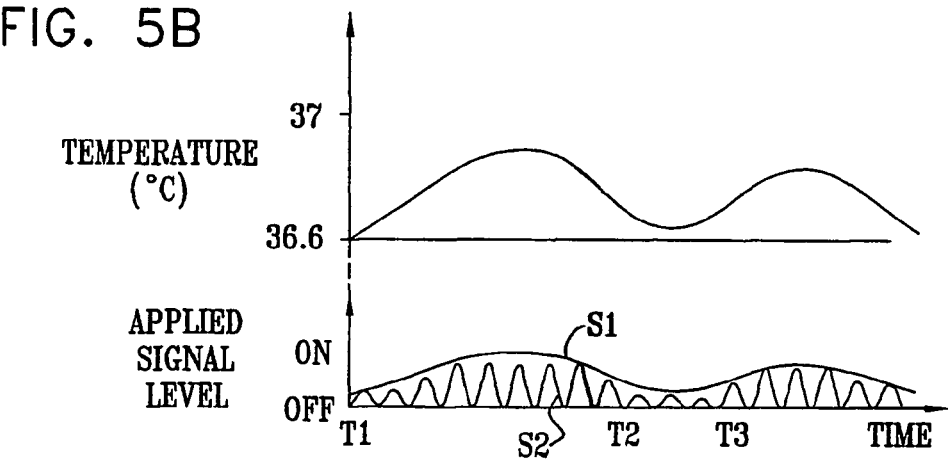

FIG. 5B is a graph schematically illustrating a mode of operation of one or more of the devices shown in FIGS. 1-4, in accordance with another preferred embodiment of the present invention. In this embodiment, the amplitude of the waveform applied to the SPG is varied among a continuous set of values (S1), or a discrete set of values (S2), responsive to the measured temperature, in order to achieve the desired performance. It will be appreciated that other feedback parameters measured in the head (e.g., intracranial pressure and/or cerebral blood flow), as well as measured systemic parameters (e.g., heart rate) and subjective patient inputs may be used in conjunction with or separately from temperature measurements, in order to achieve generally optimal performance of the implanted apparatus.

Figure 6:
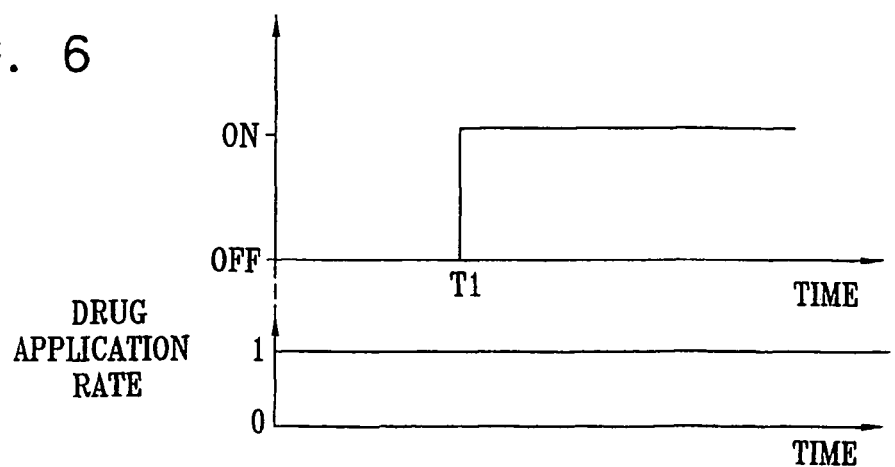
FIG. 6 is a schematic illustration of a mode of operation of the stimulators shown in FIGS. 1 and 2, synchronized with a drug delivery system, in accordance with a preferred embodiment of the present invention.
Figure 14:
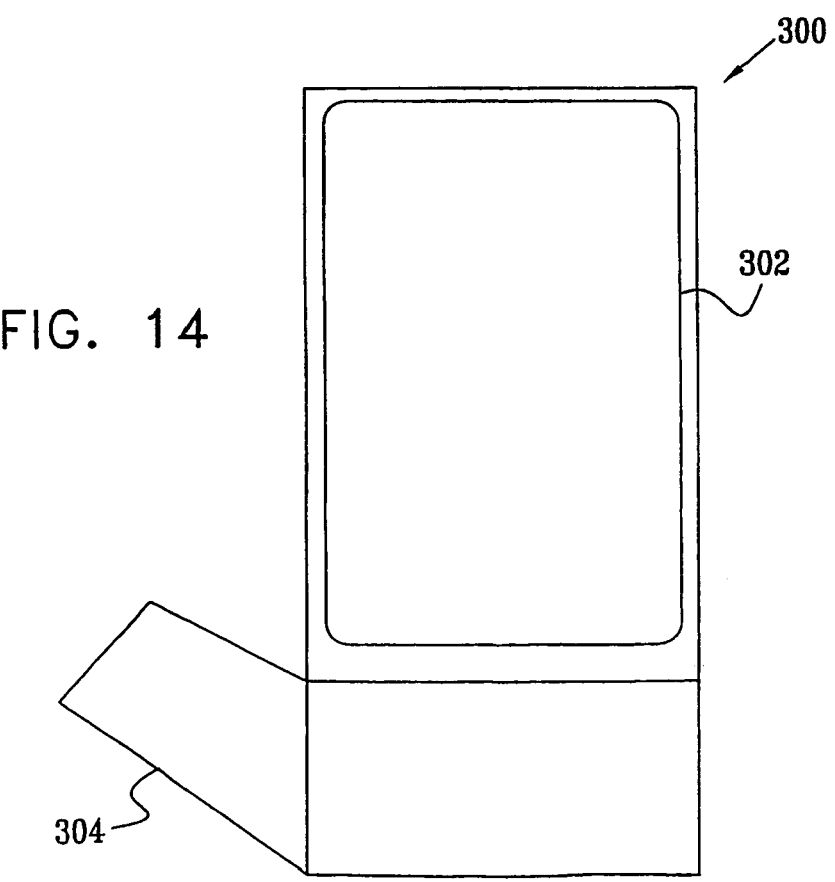
FIG. 14 is a schematic sectional illustration of a nasal inhaler, for use in presenting an odorant to a subject, in accordance with a preferred embodiment of the present invention.

FIG. 6 is a graph schematically illustrating a mode of operation of one or more of the devices shown in FIG. 14, in accordance with a preferred embodiment of the present invention. In this embodiment, a drug is administered to the patient at a constant rate, e.g., intravenously, prior to the initiation of stimulation of the SPG at time T1. Advantageously, this prior generation of heightened concentrations of the drug in the blood tends to provide relatively rapid transfer of the drug across the BBB and into the brain, without unnecessarily prolonging the enhanced permeability of the BBB while waiting for the blood concentration of the drug to reach an appropriate level. Alternatively, for some applications it is desirable to give a single injection of a bolus of the drug shortly before or after initiation of stimulation of the SPG. Typically, combined administration and stimulation schedules are determined by the patient's physician based on the biochemical properties of each drug targeted at the brain.

Figure 7:
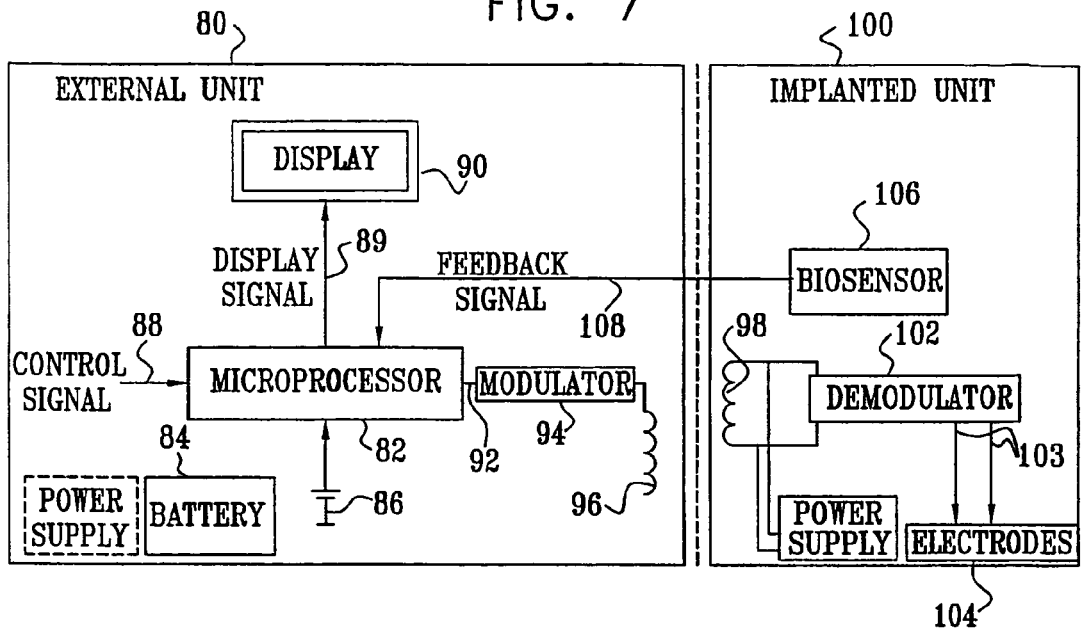
FIG. 7 is a schematic block diagram illustrating circuitry for use with the stimulator shown in FIG. 1, where the stimulator is driven by an external controller and energy source using a modulator and a demodulator, in accordance with a preferred embodiment of the present invention.

FIG. 7 is a schematic block diagram showing circuitry for parasympathetic stimulation, which is particularly useful in combination with the embodiment shown in FIG. 1, in accordance with a preferred embodiment of the present invention. An external unit 80 preferably comprises a microprocessor 82 that is powered by a battery 84 and/or an AC power source. Microprocessor 82 is grounded through battery 84 or through an optional ground 86.

In a typical mode of operation, an external control signal 88 is input to microprocessor 82, along with a feedback signal 108 from one or more biosensors 106, which are typically disposed in a vicinity of an implanted unit 100 or elsewhere on or in the patients body. Responsive to signals 88 and 108, microprocessor 82 preferably generates a display signal 89 which drives a display 90, as described hereinabove. In addition, microprocessor 82 preferably processes external control signal 88 and feedback signal 108, to determine parameters of an output signal 92, which is modulated by a modulator 94. The output therefrom preferably drives a current through an electromagnetic coupler 96, which inductively drives an electromagnetic coupler 98 of implanted unit 100. A demodulator 102, coupled to electromagnetic coupler 98, in turn, generates a signal 103 which drives at least one electrode 104 to apply current to the SPG or to other tissue, as appropriate.

Preferably, biosensor 106 comprises implantable or external medical apparatus including, for example, one or more of the following:

a blood flow sensor,
a temperature sensor,
a chemical sensor,
an ultrasound sensor,
transcranial Doppler (TCD) apparatus,
laser-Doppler apparatus,
a systemic or intracranial blood pressure sensor (e.g., comprising a piezoelectric crystal fixed to a major cerebral blood vessel, capable of detecting a sudden blood pressure increase indicative of a clot),
a kinetics sensor, comprising, for example, an acceleration, velocity, or level sensor (e.g., a mercury switch), for indicating body dispositions such as a sudden change in body attitude (as in collapsing),
an electroencephalographic (EEG) sensor comprising EEG electrodes attached to, or implanted in, the patients head, for indicating changes in neurological patterns, such as symptoms of stroke or migraine,
a blood vessel clot detector (e.g., as described hereinbelow with reference to FIG. 13), or
other monitors of physiological quantities suitable for carrying out the objects of this or other embodiments of the present invention.

Figure 8:
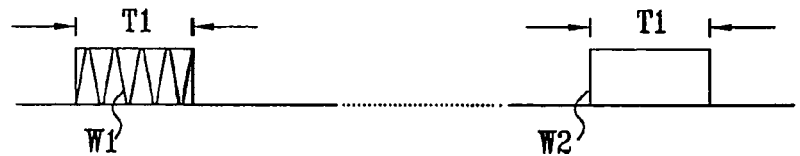
FIG. 8 depicts sample modulator and demodulator functions for use with the circuitry of FIG. 7, in accordance with a preferred embodiment of the present invention.

FIG. 8 is a schematic illustration showing operational modes of modulator 94 and/or demodulator 102, in accordance with a preferred embodiment of the present invention. The amplitude and frequency of signal 92 in FIG. 7 can have certain values, as represented in the left graph; however, the amplitude and frequency are modulated so that signal 103 has different characteristics.

Figure 9:
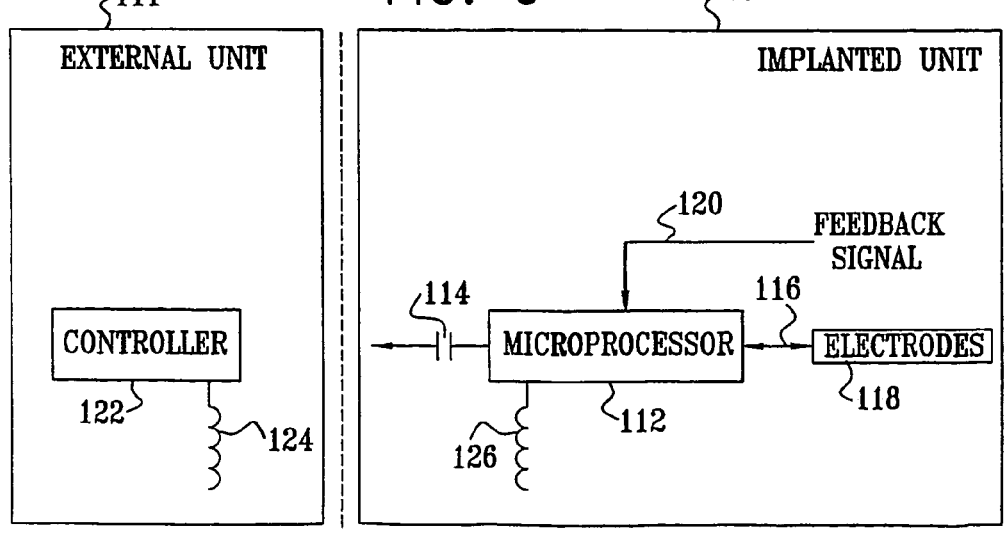

FIG. 9 is a schematic illustration of further apparatus for stimulation of the SPG, in accordance with a preferred embodiment of the present invention. In this embodiment, substantially all of the processing and signal generation is performed by circuitry in an implanted unit 110 in the patient, and, preferably, communication with a controller 122 in an external unit 111 is performed only intermittently. The implanted unit 110 preferably comprises a microprocessor 112 coupled t a battery 114. Microprocessor 112 generates a signal 116 that travels along at least one electrode 118 to stimulate the SPG. A feedback signal 120 from a biosensor (not shown) and/or from electrode 118 is received by microprocessor 112, which is adapted to modify stimulation parameters responsive thereto. Preferably, microprocessor 112 and controller 122 are operative to communicate via electromagnetic couplers 126 and 124, in order to exchange data or to change parameters. Further preferably, battery 114 is inductively rechargeable by electromagnetic coupling.

FIG. 10A is a schematic illustration of a stimulator 150, in accordance with a preferred embodiment of the present invention Preferably, substantially all of the electronic components (including an electronic circuit 158 having a rechargeable energy source) are encapsulated in a biocompatible metal case 154. An inductive coil 156 and at least one electrode 162 are preferably coupled to circuit 158 by means of a feed-through coupling 160. The inductive coil is preferably isolated by an epoxy coating 152, which allows for higher efficiency of the electromagnetic coupling.

FIG. 10B is a schematic illustration of another configuration of an implantable stimulator, in accordance with a preferred embodiment of the present invention. Preferably, substantially all of the electronic components (including an inductive coil 176 and an electronic circuit 178 having a rechargeable energy source) are encapsulated in a biocompatible metal case 174. One or more feed-throughs are preferably provided to enable coupling between at least one electrode 182 and the electronic circuit, as well as between inductive coil 176 and another inductive coil (not shown) in communication therewith.

With reference to FIGS. 10A and 10B, the energy source for electronic circuits 158 and 178 may comprise, for example, a primary battery, a rechargeable battery, or a super capacitor. For applications in which a rechargeable battery or a super capacitor is used, any kind of energizing means may be used to charge the energy source, such as (but not limited to) standard means for inductive charging or a miniature electromechanical energy converter that converts the kinetics of the patient movement into electrical charge. Alternatively, an external light source (e.g., a simple LED, a laser diode, or any other light source) may be directed at a photovoltaic cell in the electronic circuit Further alternatively, ultrasound energy is directed onto the implanted unit, and transduced to drive battery charging means.

Figure 11:
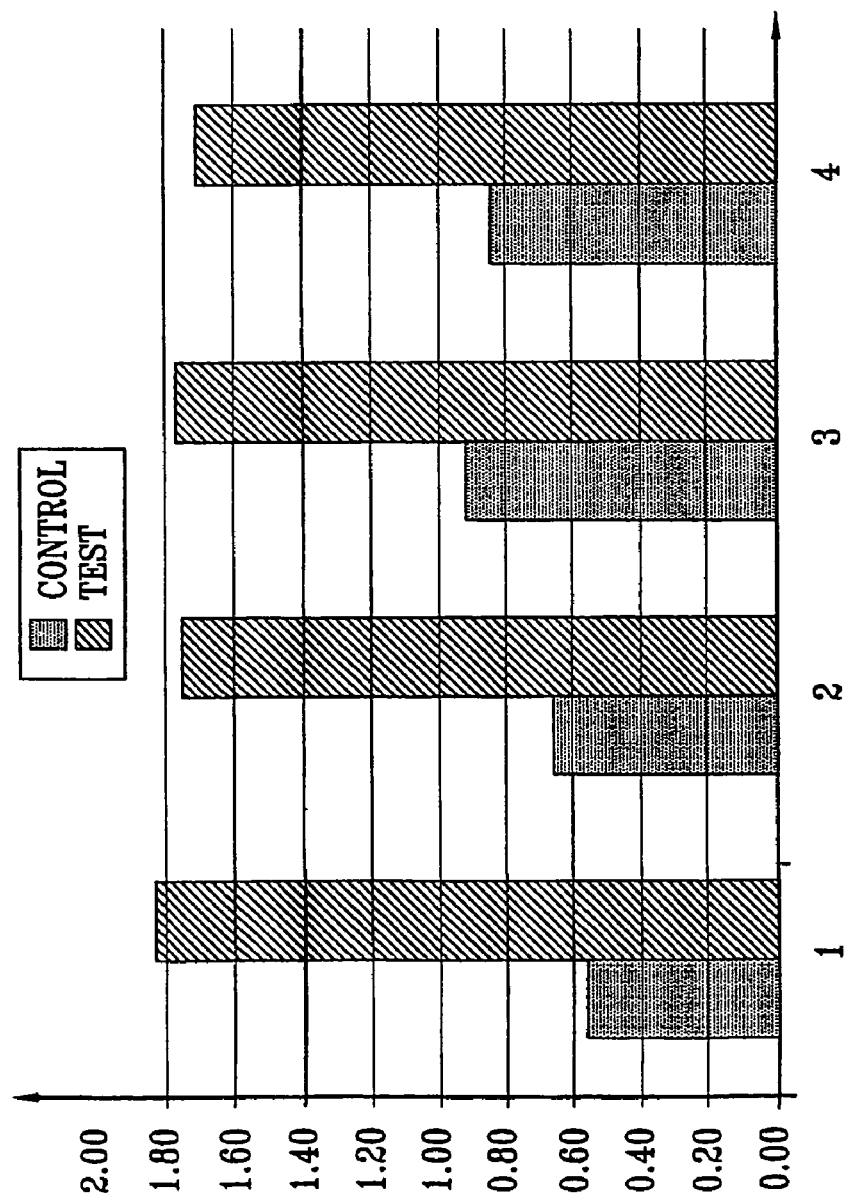
FIGS. 11 and 12 are bar graphs showing experimental data collected in accordance with a preferred embodiment of the present invention.
Figure 12:
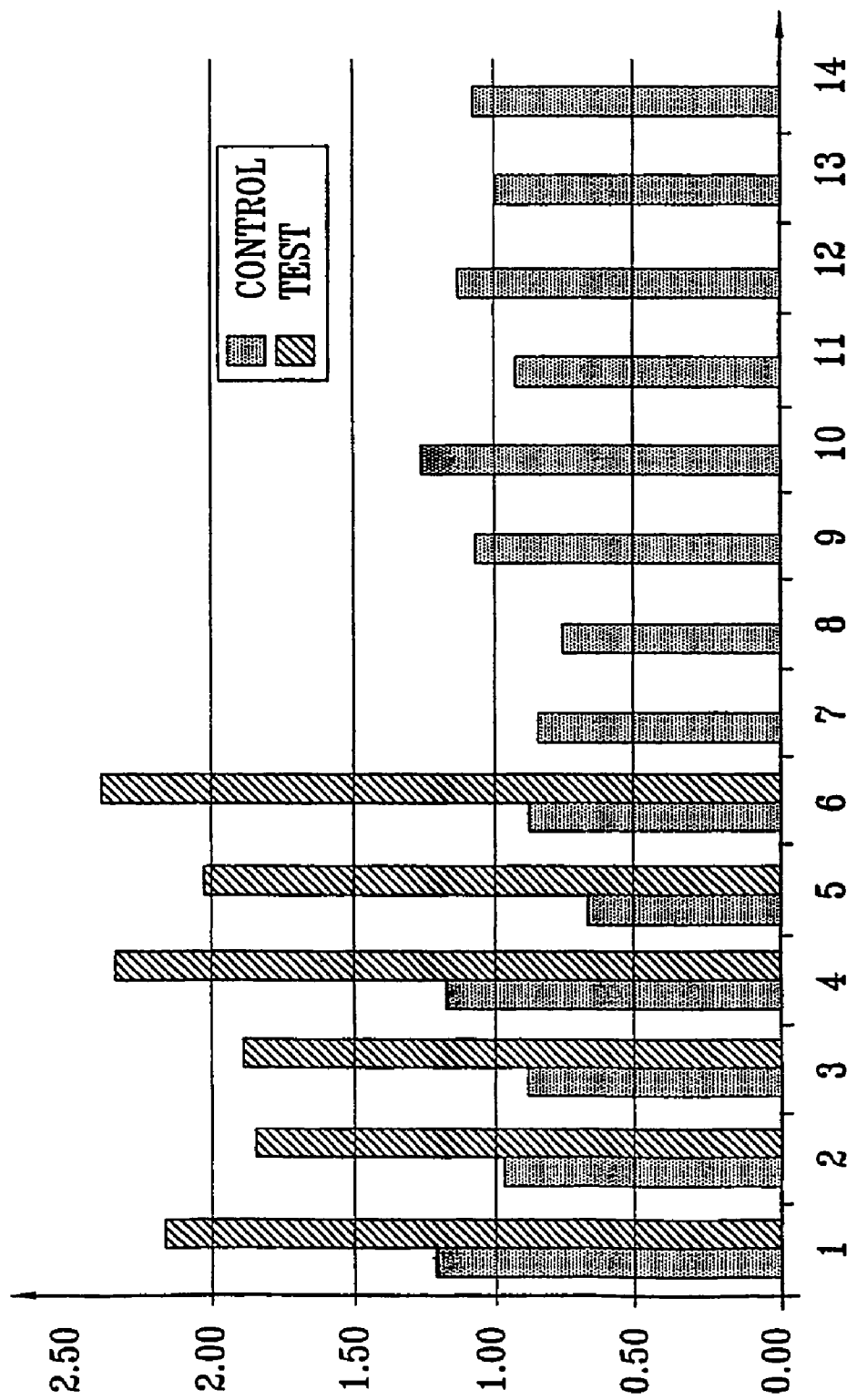

FIGS. 11 and 12 are bar graphs showing experimental results obtained during rat experiments performed in accordance with a preferred embodiment of the present invention. A common technique in monitoring bio-distribution of materials in a system includes monitoring the presence and level of radio-labeled tracers. These tracers are unstable isotopes of common elements (e.g., Tc, In, Cr, Ga, and Gd), conjugated to target materials. The chemical properties of the tracer are used as a predictor for the behavior of other materials with similar physiochemical properties, and are selected based on the particular biological mechanisms that are being evaluated. Typically, a patient or experimental animal is placed on a Gamma camera, or target tissue samples can be harvested and placed separately into a well counter. For the purpose of the present set of experiments which were performed, the well counter method was chosen due to its higher sensitivity and spatial resolution. A series of experiments using 99Tc-DTPA (DTPA molecule conjugated to a 99-Technetium isotope) were performed. The molecular weight of 99Tc-DTPA is 458 Da, its lipophilicity is negative, and its electric charge is +1. These parameters are quite similar with pharmacological agents used in standard chemotherapy, such as tamoxifen, etoposide and irinotecan.

FIGS. 11 and 12 show results obtained using 99Tc-DTPA penetration assays using ordinary brain sampling techniques (FIG. 11) and peeled brain techniques (FIG. 12). The x-axis of each graph represents different experimental runs, and the y-axis of each graph is defined as: [(hemisphere radioactivity)/(hemisphere weight)]/[(total injected radioactivity)/(total animal weight)]. The results obtained demonstrate an average 2.5-fold increase in the penetration of 99Tc-DTPA to the rat brain. It is noted that these results were obtained by unilateral stimulation of the SPG. The inventors believe that bilateral SPG stimulation will approximately double drug penetration, relative to unilateral SPG stimulation.

In both FIGS. 11 and 12, some animals were designated as control animals, and other animals were designated as test animals. In each group, the left and right hemispheres were tested separately, and the height of each bar represents, for a given animal and a given hemisphere, the normalized level of radioactivity as defined above. Thus, FIG. 11 shows results from a total of four test hemispheres and four control hemispheres. FIG. 12 shows results from six test hemispheres and fourteen control hemispheres. The juxtaposition of control and test bars in the bar graphs is not meant to imply pairing of control and test hemispheres.

Figure 13:
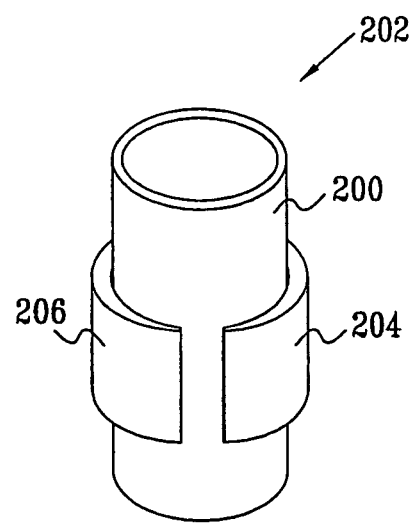
FIG. 13 is a schematic illustration of a sensor for application to a blood vessel, in accordance with a preferred embodiment of the present invention.

FIG. 13 is a schematic illustration of acoustic or optical clot detection apparatus 202, for use, for example, in providing feedback to any of the microprocessors or other circuitry described hereinabove, in accordance with a preferred embodiment of the present invention. The detection is preferably performed by coupling to a major blood vessel 200 (e.g., the internal carotid artery or aorta) a detecting element comprising an acoustic or optical transmitter/receiver 206, and an optional reflecting surface 204. Natural physiological liquids may serve as a mediating fluid between the device and the vessel. Preferably, the transmitter/receiver generates an ultrasound signal or electromagnetic signal which is reflected and returned, and a processor evaluates changes in the returned signal to detect indications of a newly-present clot. Alternatively, a transmitter is placed on side of the vessel and a receiver is placed on the other side of the vessel. In either case, for some applications, more than one such apparatus 202 are placed on the vessel, in order to improve the probability of successful clot detection for possible estimation of the clot's direction of motion within the vessel, and to lower the false alarm (i.e. false detection) rate.

Alternatively or additionally, the changes induced by electrical stimulation as described hereinabove are achieved by presenting odorants to an air passage of a patient, such as a nasal cavity or the throat There is animal evidence that some odorants, such as propionic acid, cyclohexanone, and amyl acetate, significantly increase cortical blood flow when presented to the nasal cavity. This has been interpreted by some researchers as evidence that these odorants (e.g., environmental pollutants) may be involved in the formation of various headaches by increasing cerebral blood flow. The temporal profile and other quantitative characteristics of such odorant stimulation are believed by the present inventors to have a mechanism of action that has a neuroanatomical basis overlapping with that of the electrical stimulation of the SPG. Furthermore, experimental animal evidence collected by the inventors and described in a U.S. provisional patent application to Shalev and Gross entitled, "SPG stimulation," filed Mar. 28, 2002, which is assigned to the assignee of the present invention and is incorporated herein by reference, suggest a correlation between the mechanisms of increasing cerebral blood flow and increased cerebrovascular permeability. It is hypothesized that such increased cerebral blood flow caused by odorants is a result of stimulation of parasympathetic and/or trigeminal fibers. These fibers may mediate cerebral blood flow changes directly, by communicating with the SPG, or by some other mechanism. It is also hypothesized that these odorants stimulate via reflex arcs the SPG or other autonomic neural structures that innervate the cerebrovascular system. Therefore, the inventors hypothesize, odorant "stimulation" may increase cerebral blood flow in general, and cortical blood flow in particular, by some or all of the same mechanisms as electrical stimulation, as described hereinabove. Alternatively, odorants may cause increased cortical blood flow by other mechanisms, such as by entering the blood stream and reaching the affected blood vessels in the brain or by parasympathetic stimulation via the olfactory nerve. In addition to the effect on cerebral blood flow, the introduction of odorants into an air passage is also expected to induce an increase in the permeability of the anterior two thirds of the cerebrovascular system to circulating agents of various sizes, i.e. to increase the permeability of the BBB. Similarly, presenting certain other odorants to an air passage decreases cerebral blood flow and decreases the permeability of the BBB.

Odorants that may increase or decrease cerebral blood flow and/or the permeability of the BBB include, but are not limited to, propionic acid, cyclohexanone, amyl acetate, acetic acid, citric acid, carbon dioxide, sodium chloride, ammonia, menthol, alcohol, nicotine, piperine, gingerol, zingerone, allyl isothiocyanate, cinnamaldehyde, cuminaldehyde, 2-propenyl/2-phenylethyl isothiocyanate, thymol, and eucalyptol.

According to a preferred embodiment of the instant invention, a method is provided to enhance delivery of therapeutic molecules across the BBB by presenting an odorant to an air passage of a patient, such as a nasal cavity or the throat In a preferred application, this method serves as a neurological drug delivery facilitator. The odorant is preferably presented using apparatus known in the art, such as aqueous spray nasal inhalers; metered dose nasal inhalers; or air-dilution olfactometers. Alternatively or additionally, the odorant is presented by means of an orally-dissolvable capsule that releases the active odorants upon contact with salivary liquids. The odorants reach the appropriate neural structures and induce vasodilatation, vasoconstriction and/or cerebrovascular permeability changes. Delivery of a drug can be achieved by mixing the drug with the odorant; by intravenously, intraperitoneally, or intramuscularly administering the drug, or by other delivery methods known in the art For some applications, it is desirable to combine a local analgesic with the odorant in order to diminish any possible sensation of pain or discomfort that may directly or indirectly (e.g., via a reflex arc) accompany the odorant action upon nerves in the head. For example, preventing neural transmission in the neighboring pain fibers maybe performed as a "pre-odorant" treatment, by topical administration of capsaicin together with a local analgesic for several days prior to the use of odorant stimulation. In this manner, the odorants typically induce the SPG-related response with a reduced or eliminated sensation of pain or discomfort.

FIG. 14 is a schematic sectional illustration of a nasal inhaler 300, for use in presenting an odorant to a subject, in accordance with a preferred embodiment of the present invention. Nasal inhaler 300 preferably comprises apparatus known in the art, such as an aqueous spray nasal inhaler, a metered dose nasal inhaler, or an air-dilution olfactometer. The odorant is stored in an odorant-storage vessel 302, and is delivered to a nasal passage using an odorant-delivery element 304, such as a nasal piece. Alternatively or additionally, the odorant is presented by means of an orally-dissolvable capsule that releases the active odorants upon contact with salivary liquids. The odorants reach the appropriate neural structures and induce vasodilatation, vasoconstriction and/or cerebrovascular permeability changes.

Figure 15:
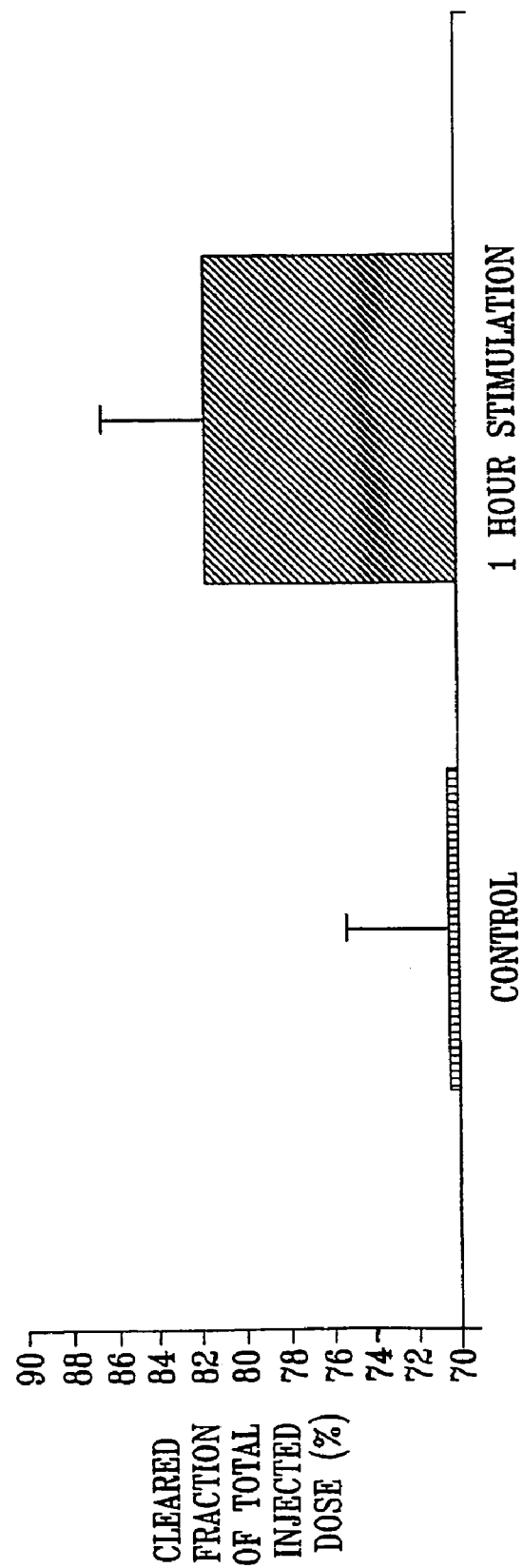

FIG. 15 is a graph showing the results of an efflux study, performed in accordance with an embodiment of the present invention. Techniques described in the following two articles, which are incorporated herein by reference, were applied for use with this embodiment:

Asaba et al., "Blood brain barrier is involved in the efflux transport of a neuroactive steroid, dehydroepiandrosterone sulfate, via organic anion transporting polypeptide 2." J. Neurochem. 75, pp. 1907-1916, (2000).

Isakovic et al., "The efflux of purine nucleobases and nucleosides from the rat brain." Neuroscience Letters 318, pp. 65-68, (2002).

Male Wistar rats (280-300 g; Harlan) were used. Six rats were in an experimental group, and six rats were in a control group. A BEI (brain efflux index) study was performed according to the method described in an article by Kakee et al., "Brain efflux index as a novel method of analyzing efflux transport at the blood brain barrier." J. Pharmacol. Exp. Ther. 277, 1550-1559. (1996), which is incorporated herein by reference. Rats were anesthetized by intraperitoneal administration of Phenobarbital, and then mounted on a stereotaxic frame. A burr hole was made 5.5 mm lateral and 0.2 mm anterior to the bregma, and a fine injection needle was advanced to a depth of 4.5 mm. Then, 0.50 ml of [3H]PNA (150,000 disintegrations per minute (dpm), 0.5'-CCGCTCCG-3', MW. 2122) dissolved in extracellular fluid (ECF) buffer (122 mM NaCl, 25 mM NaHCO3, 10 mM D-glucose, 3 mM KCl, 1.4 mM CaCl2, 1.2 mM MgSO4, 0.4 mM K2HPO4, 10 mM HEPES, pH 7.4) was administered over 1 min using a 5.0-ml microsyringe (Hamilton, Reno, Nev., U.S.A.) fitted with a fine needle at a depth of 4.5 mm from the surface of the scalp (that is, in the parietal cortex area 2 (Par2) region). At the end of the experiment (60 min), an aliquot of CSF was collected from the cisterna magna, using techniques described in Kakee et al., 1996. The whole brain was subsequently isolated, and the left cerebrum, right cerebrum, and cerebellum were isolated. After weighing, tissue samples were dissolved in 1 ml of 2 M NaOH at 50° C. for 3 h and then were mixed with 4 ml of scintillation cocktail. The associated radioactivity was measured in a liquid scintillation counter equipped with an appropriate crossover correction of 3H (LS-6500; Beckman, Fullerton, Calif., U.S.A.).

The SPG stimulation protocol included cycling between on-periods, lasting 90 seconds, and off-periods, lasting for 60 seconds. During each on-period, a 5 volt, 10 Hz signal was applied to the SPG, each pulse having a pulse width of 1 ms. The signal was applied using a concentric bipolar electrode, both poles of the electrode being inserted slightly into the SPG.

FIG. 15 clearly shows the increased clearance of the injected tracer from the animals that received electrical SPG stimulation, compared to the clearance in the non-stimulated (i.e., control) animals. The error bars represent one standard deviation. No electrodes were inserted into the SPG of the control animals.

Figure 16:
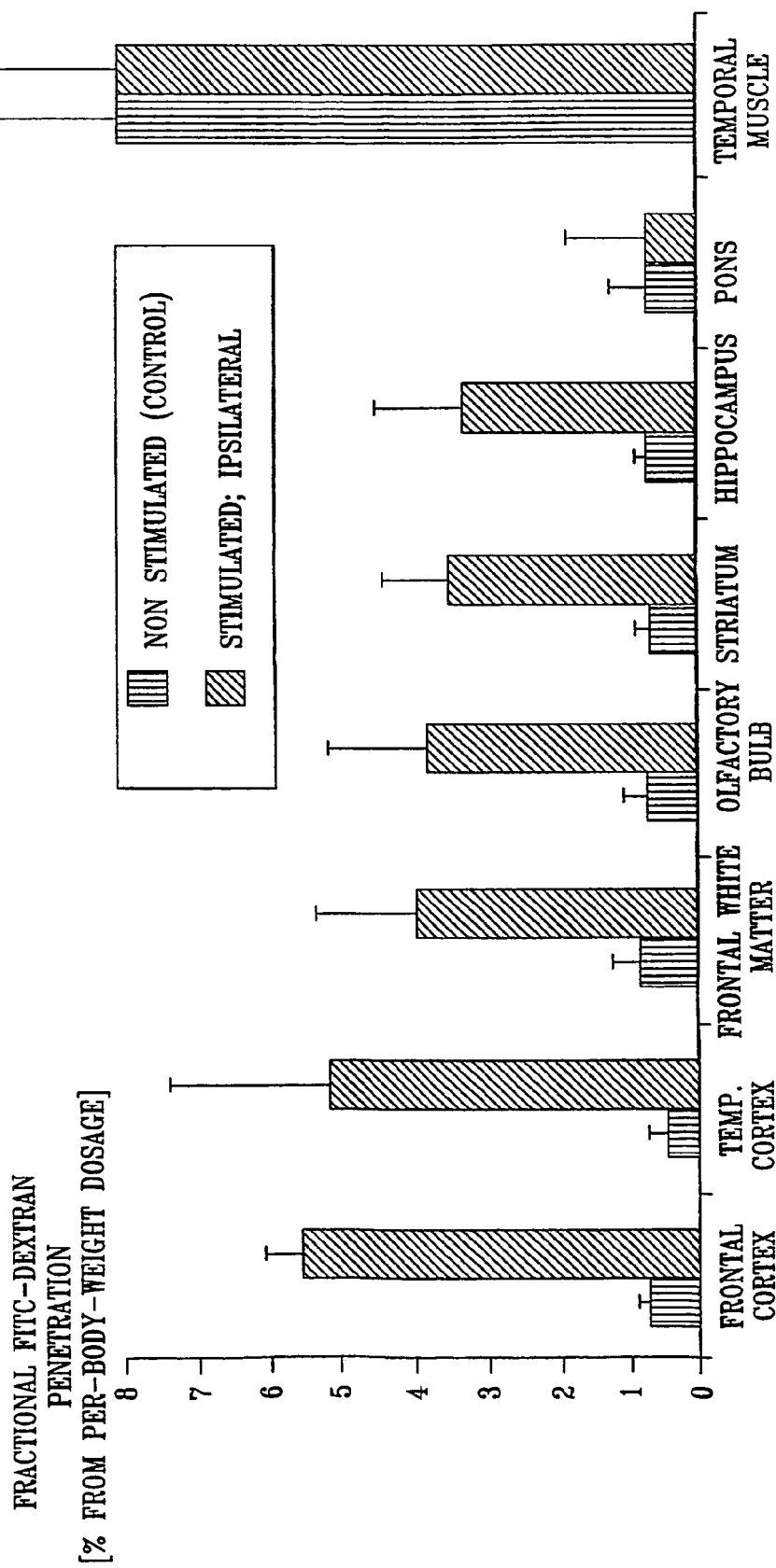

FIG. 16 is a graph showing the results of an experiment performed in accordance with an embodiment of the present invention. Four beagles were in a control (non-stimulated)

group, and four beagles were in a stimulated group. No electrodes were applied to the SPG of the animals of the control group. At time zero, a solution of 10 kDa FITC-dextran tracer was administered intravenously, and, at the same time, SPG stimulation was initiated Administration of the dextran was performed continuously over a 20 minute period, and SPG stimulation continued for 30 minutes (i.e., for 10 minutes after termination of the dextran administration). The SPG stimulation protocol included cycling between on-periods, lasting 90 seconds, and off-periods, lasting for 60 seconds. During each on-period, a 6 volt, 10 Hz signal was applied to the SPG, each pulse having a pulse width of 1 ms. The signal was applied using a concentric bipolar electrode, both poles of the electrode being inserted slightly into the SPG.

After termination of the SPG stimulation (or equivalent time period in the control group), each animal was sacrificed. Concentrations of dextran in various parts of each beagle's brain were measured. In the control group, concentrations in the left half and the right half were measured separately, such that the control results shown in FIG. 16 represent n=8, from four animals. In the experimental group, four animals were used. For each experimental animal, only one sample was taken from each brain region, ipsilateral to the stimulation (thus n=4).

FIG. 16 shows results from six brain regions known to be regulated to some extent by the SPG (the frontal cortex, the temporal cortex, frontal white matter, the olfactory bulb, the striatum, and the hippocampus). FIG. 16 also shows dextran concentrations measured in the pons, a portion of the brain regulated by the otic ganglion (and substantially not by the SPG). Notably, the results of this experiment show that dextran concentrations in each of the six regions regulated by the SPG were significantly higher in the SPG-stimulated group than in the control group. The high concentration of the dextran tracer (a large molecule), indicates that BBB permeability was substantially increased as a result of the SPG stimulation, in the brain regions regulated by the SPG. Also notable is the almost exact equivalence between the dextran levels in the pons of the SPG-stimulated animals and in the pons of the control animals. The contrast between: (a) the equivalence of the experimental and control groups, in a non-SPG-regulated brain tissue, and (b) the significant differences between the experimental and control groups in the SPG-regulated brain tissues, is a strong indication that the displayed significant effect of the experimental protocol shown in FIG. 16 is a result of modulating the functioning of the SPG and its control over BBB permeability in certain portions of the brain.

In addition to the results shown in FIG. 16 and described hereinabove, the inventor additionally assessed the concentration of the dextran tracer in temporal muscle of the animals in the SPG-stimulated group and in the control group. It is noted that temporal muscle, being outside of the brain, has no protection from the BBB. The results show that the dextran concentrations rose to high and essentially equivalent values in the temporal muscle of the animals in both the SPG-stimulated group and the control group. This, in combination with the pons data, shows that SPG stimulation as provided herein only produced a measured effect on brain tissue that is regulated by the SPG.

FIG. 17 shows results from an experiment which included one hour of continuous SPG stimulation in five rats, in accordance with an embodiment of the present invention. Prior to the initiation of SPG stimulation, cerebral blood flow (CBF) was measured, and this measurement provided a baseline for subsequent CBF measurements. CBF was continuously recorded throughout the hour of SPG stimulation, and continued to be recorded for 30 minutes after the stimulation ceased. SPG stimulation protocols were identical to those described hereinabove with reference to FIG. 15.

Three bars are shown in FIG. 17. The left bar represents the average blood flow change 20 minutes after SPG stimulation was initiated. The middle bar shows average blood flow change 40 minutes after stimulation was initiated, and the right bar shows average blood flow change 20 minutes after the termination of SPG stimulation From this figure, it is evident that during SPG stimulation, a CBF increase of around 50% (i.e. 150% of original blood flow level) is measured. This increase in cerebral blood flow is believed to be associated with improved metabolic state of brain tissue supplied by the CBF, as supported by other data collected by the inventor (not shown).

In general, it is believed that substantially all pharmacological treatments aimed at cerebral cells for neurological and psychiatric disorders are amenable for use with these embodiments of the present invention. In particular, this embodiment may be adapted for use in the treatment of disorders such as brain tumors, epilepsy, Parkinson's disease, Alzheimer's disease, multiple sclerosis, schizophrenia, depression, stress, anxiety, disorders requiring the administration of various growth factors, and other CNS disorders that are directly or indirectly affected by changes in cerebral blood flow or by BBB permeability changes.

Alternatively or additionally, a method is provided for increasing or reducing cortical blood flow and/or inducing or inhibiting vasodilation (even in the absence of BBB permeability changes) by presenting an odorant to an air passage of a patient, such as a nasal cavity or the throat, for treatment of a condition. Patients with the aforementioned disorders and other disorders are generally helped by vasodilation and the resultant improvement in oxygen supply to neurons and other tissue. For some applications, this treatment is given on a long-term basis, e.g., in the chronic treatment of Alzheimer's patients. For other applications, the treatment is performed on a short-term basis, e.g., to minimize the damage following an acute stroke event and initiate neuronal and therefore functional rehabilitation. Alternatively or additionally, the method provided above can be used for diagnostic purposes or in conjunction with other diagnostic methods and/or apparatus known in the art, in order to enhance diagnostic results, reduce procedure risk, reduce procedure time, or otherwise improve such diagnostic procedures and/or diagnostic results. For example, methods and apparatus described herein may be used to increase the uptake into the brain of a radio-opaque material, in order to facilitate a CT scan.

Decreasing cerebral blood flow by presenting certain odorants to an air passage is used in accordance with some preferred embodiments of the present invention to treat or prevent various types of headaches, especially with an autonomic nervous system (ANS) etiology, such as migraine and cluster headaches.

In a preferred embodiment of the present invention, stimulation of the SPG may be performed using direct galvanic contact, indirect electromagnetic induction, photonic excitation, chemical excitation, mechanical excitation and other methods or combinations thereof, which are known in the art of neural stimulation. Stimulation of the SPG may be performed directly on the SPG, or the nerves connected directly or indirectly with the SPG, e.g., via reflex arc.

In a preferred embodiment of the present invention, techniques described herein are applied in combination with methods and apparatus described in PCT Application IL 01/00402, filed May 7, 2001, entitled, "Method and apparatus for stimulating the sphenopalatine ganglion to modify properties of the BBB and cerebral blood flow," U.S. Provisional Patent Application 60/364,451, filed Mar. 15, 2002, entitled, "Applications of stimulating the sphenopalatine ganglion (SPG)," U.S. Provisional Patent Application 60/368,657, filed Mar. 28, 2002, entitled, "SPG stimulation," and/or U.S. Provisional Patent Application 60/376,048, filed Apr. 25, 2002, entitled, "Methods and apparatus for modifying properties of the BIB and cerebral circulation by using the neuroexcitatory and/or neuroinhibitory effects of odorants on nerves in the head," all of which are assigned to the assignee of the present invention and are incorporated herein by reference.

The better delivery of drugs, as provided in accordance with preferred embodiments of the present invention, is an important factor in the treatment of various disorders, such as Parkinson's disease, Alzheimer's disease, and other neurological diseases. For some applications, the trans-BBB delivery of various growth factors is facilitated using the techniques described herein. Growth factors are typically large molecules that stimulate the growth of neurons, and, in accordance with a preferred embodiment of the present invention, are used to treat degenerative disorders, such as Parkinson's disease, Alzheimer's disease, and Motor Neuron Diseases (e.g., Lou Gehrig's disease).

Alzheimer's disease is becoming a major source of disability and financial load with the increase in life expectancy. In recent years, vascular factors have been considered prominent in the pathophysiology of the disease. Current therapy is generally concentrated along one line—cholinomimetic medications, which typically, at most, slow down the deterioration of cognitive function in patients. SPG stimulation, as provided in accordance with preferred embodiments of the present invention, typically increases blood flow and oxygen supply to the brain, and therefore help these patients. For this use, permanent stimulators may be implanted in the nasal cavity, for long-term intermittent stimulation In a preferred embodiment, the delivery of cholinomimetic medications is facilitated by SPG stimulation.

Apart from molecular parameters, the permeability of the BBB and active transport mechanisms, a major determinant of molecular transport across the BBB is their concentration gradient—between the CNS and the cerebral circulation. In cases where a compound has a higher concentration in the brain than in the cerebral circulation, opening of the BBB, preferably, but not necessarily, using techniques described herein leads to an increased net transport of that compound from the CNS into the circulation In a preferred embodiment, this technique is used to facilitate a diagnosis, e.g., by enhancing permeability of the BBB, taking a blood sample, and testing the blood sample for increased levels of the compound.

In a preferred embodiment of the present invention, parasympathetic fibers associated with the SPG are stimulated, preferably by using electrical stimulation and/or odorant presentation techniques described herein, thereby rendering the BBB permeable to certain compounds in the CNS. One or more of such compounds are then analyzed by analyzing the blood of the patient By testing such compounds that are indicative of the presence of AD, AD is diagnosed. Advantageously, such a testing procedure is minimally invasive. Alternatively or additionally, molecular passage is increased to another body compartment and/or fluid, such as plasma, serum, ascites, or cerebrospinal fluid.

Moreover, in accordance with a preferred embodiment of the present invention, a controlled, reversible suppression of the impedance of the BBB is useful as a stand-alone treatment, when said suppression facilitates clearance of neurotoxic compounds, such as β-Amyloid, tau, PS1, and PS2, from the CNS into the systemic circulation. Once in the systemic circulation, these neurotoxic compounds may be metabolized and removed from the body with greater ease and with fewer side effects, compared to effects that accompany their presence in the CNS.

The following examples demonstrate selected therapeutic and diagnostic applications of SPG stimulation in the management of Alzheimer's disease. It should be appreciated by those of skill in the art, that the following examples are set forth for demonstrative purposes. However, those of skill in the art should, in light of the present disclosure, appreciate that many changes can be made in the specific embodiments disclosed and still obtain a like or similar result without departing from the spirit and scope of the invention. The following description relates to specific embodiments for stimulation of the SPG and related neural structures, possible system configurations for the stimulator device, variations or combinations of the therapeutic and diagnostic modalities that accompany SPG stimulation and complementary explanation for the various mechanisms of actions of such a system for AD management Furthermore, the methods described herein may be either directly, or indirectly applicable for the management of other CNS disorders, such as Parkinson's disease, epilepsy, ALS, MS and more. All references cited herein, including articles, patents, and published patent applications, are incorporated herein by reference.

EXAMPLE 1

Therapeutics (Glutamate Inhibitors)

Excitotoxicity is related to excessive activation of glutamate receptors which results in neuronal cell death. The physiological function of glutamate receptors is the mediation of ligand-gated cation channels with the concomitant influx of calcium, sodium and potassium through this receptor-gated channel. The influx of these cations is essential for maintaining membrane potentials and the plasticity of neurons which in itself plays a pivotal role in cognitive function of the central nervous system (Li, H. B. et al., Behav. Brain Res. 83:225-228, 1997; Roesler, R. et al., Neurology 50:1195, 1998; Wheal, H. V. et al., Prog. Neurobiol. 55:611-4640, 1998; Wangen, K et al., Brain Res. 99:126-130, 1997). Excitotoxicity plays an important role in neuronal cell death following acute insults such as hypoxia, ischemia, stroke and trauma, and it also plays a significant role in neuronal loss in AIDS dementia, epilepsy, focal ischemia (Coyle, J. T. et al., Science 262:689-695, 1993). Neurodegenerative disorders, such as Huntington's disease (HD), Alzheimer's disease (AD), Parkinson's disease (PD) and amyotrophic lateral sclerosis (ALS), are characterized by the progressive loss of a specific population of neurons in the central nervous system. Growing evidence suggests that glutamate-mediated excitotoxicity may be a common pathway which contributes to neuronal cell death in a wide range of neurological disorders (Coyle, J. T. et al., Science 262:689-695, 1993). The molecular mechanisms of excitotoxicity-mediated neuronal cell death remains obscure. Over-production of free radicals that lead to impairment of mitochondrial function is the most widely held hypothesis (Beal, M. F. et al., Ann. Neurol. 38:357-366, 1995; Coyle, J. T. et al., Science 262:689-695, 1993). However, it is unclear in the literature whether the increase of free radicals is the precursor that initiates neuronal degeneration or, rather, a subsequent consequence of neuronal degeneration. Interestingly, administration of antioxidants is reported as having little neuroprotective effect in patients suffering from various neurodegenerative diseases (Shults, C. W. et al., Neurology 50:793-795, 1998). Thus, some other mechanism(s) must exist for excitotoxicity-induced neuronal cell death.

A potential treatment modality for AD is the systemic administration of a JNK (c-Jun amino-terminal kinase) or MLK (Mixed lineage kinase) apoptosis inhibitor as a means for preventing AD-related apoptosis of brain cells. However, without the use of the techniques described herein, achieving a therapeutic concentration of such an inhibitor in the CNS may be accompanied by undesired dose-related side effects. Advantageously, the use of techniques described herein for enhancing drug delivery to the CNS typically enables the achievement of therapeutic results at lower dosages, which, in turn, lowers the risk of dose-related side effects.

In a preferred embodiment of the present invention, the therapeutic or prophylactic administration of such inhibitors is enhanced by stimulation of the SPG and/or its related neuroanatomical structures, by using electrical stimulation, odorant presentation, and/or other means for stimulating the SPG or for modulating permeability of the BBB.

EXAMPLE 2

Therapeutics β/γ Secretase Inhibitors

In a preferred embodiment of the present invention, methods for treatment of Alzheimer's disease target the formation of β-amyloid through the enzymes involved in the proteolytic processing of β-amyloid precursor protein. Compounds that inhibit β or γ secretase activity, either directly or indirectly, are used, in accordance with this embodiment, to control the production of β-amyloid. Advantageously, compounds that specifically target γ secretases, could control the production of β-amyloid. Typically, such inhibition of β or γ secretases reduces production of Aβ, which, in turn, reduces or prevents the neurological disorders associated with Aβ protein.

Compelling evidence accumulated during the last decade revealed that Aβ is an internal polypeptide derived from a type 1 integral membrane protein, termed b amyloid precursor protein (APP). β APP is normally produced by many cells both in vivo and in cultured cells, derived from various animals and humans. AP is derived from cleavage of β APP by as yet unknown enzyme (protease) system(s), collectively termed secretases.

The existence of at least four proteolytic activities has been postulated. They include β secretase(s), generating the N-terminus of Aβ, a secretase(s) cleaving around the 16/17 peptide bond in Aβ, and y secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. First, Aβ is the major protein found in amyloid plaques. Second, Aβ is neurotoxic and may be causally related to neuronal death observed in AD patients. Third, missense DNA mutations at position 717 in the 770 isoform of β APP can be found in affected members but not unaffected members of several families with a genetically determined (familiar) form of AD. In addition, several other β APP mutations have been described in familiar forms of AD. Fourth, similar neuropathological changes have been observed in transgenic animals overexpressing mutant forms of human β APP. Fifth, individuals with Down's syndrome have an increased gene dosage of β APP and develop early-onset AD. Taken together, these observations strongly suggest that Aβ depositions may be causally related to the AD.

It is hypothesized by the inventors that inhibiting the production of Aβ inhibits neurological degeneration by controlling the formation of amyloid plaques, reducing neurotoxicity and, generally, mediating the pathology associated with Aβ production. One method of treatment preferred by the inventors is based on drugs that inhibit the formation of Aβ in vivo, administered in combination with techniques for SPG stimulation described herein.

Methods of treatment preferably target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases could control the production of Aβ. Such inhibition of β or γ secretases could thereby reduce production of Aβ, which, in turn, could reduce or prevent the neurological disorders associated with Aβ protein.

US patent application Publication 20020055501 to Olson et al. describes pharmaceutical compositions and methods of use of such compounds, which inhibit the processing of amyloid precursor protein and, more specifically, inhibit the production of Aβ-peptide, thereby acting to prevent the formation of neurological deposits of amyloid protein.

The efficacy of administration of pharmaceutical agents that inhibit the processing of amyloid precursor protein into β-amyloid is typically substantially increased when used in conjunction with the techniques of SPG stimulation described herein.

In a preferred embodiment of the present invention, the therapeutic or prophylactic administration of such compounds targeting production of Aβ is enhanced by stimulation of the SPG and/or its related neuroanatomical structures, by using electrical stimulation, odorant presentation, and/or other means for stimulating the SPG or for modulating permeability of the BBB.

EXAMPLE 3

Therapeutics (NMDA-receptor Blocker)

US patent application Publication 20020035145 to Tsai et al., describes a method to treat various neuropsychiatric disorders, including Alzheimer's disease. Their description relates that neuropsychiatric disorders characterized by a deficit in neurotransmission via the NMDA receptor can be alleviated by a compound that acts as an agonist of the glycine site on the NMDA receptor or an inhibitor of glycine uptake. The compound is either a partial agonist such as D-cycloserine, which can be used at a dosage of 105-500 mg, or a full agonist (e.g., D-serine or D-alanine) that is selective for the NMDA receptor (compared to the inhibitory glycine receptor and other receptors), or a glycine uptake inhibitor (e.g., N-methylglycine). They describe methods for treating neuropsychiatric disorders in patients (i.e., humans). Examples of disorders that can be treated by the methods they describe include schizophrenia, Alzheimer's disease, autism, depression, benign forgetfulness, childhood learning disorders, closed head injury, and attention deficit disorder. The methods entail administering to a patient diagnosed as suffering from such a neuropsychiatric disorder a pharmaceutical composition that contains a therapeutically-effective amount of an agonist of the glycine site of the NMDA receptor or a glycine uptake inhibitor, which agonist is relatively selective for (a) the glycine site of the NMDA receptor, compared with (b) the inhibitory glycine receptor and other receptors. The pharmaceutical composition may include, for example, (i) a therapeutically effective amount of D-alanine (wherein the pharmaceutical composition is substantially free of D-cycloserine) and/or (ii) a therapeutically effective amount of D-serine, and/or (iii) D-cycloserine in an amount of 105-500 mg, and/or (iv) a therapeutically effective amount of N-methylglycine.

US patent application Publication 20010051633 to Bigge et al., describes a subtype-selective NMDA receptor ligands and the use thereof for treating or preventing neuronal loss associated with neurodegenerative diseases including Alzheimer's disease by treating or preventing the adverse consequences of the overstimulation of the excitatory amino acids.

US patent application Publication 20010047014 to Alanine et al., describes a compound of the formula 1 its R,R-, S,S-enantiomers and racemic mixtures, also suitable for the treatment of Alzheimer's disease.

In a preferred embodiment of the present invention, the therapeutic or prophylactic administration of such compounds described in this example (Example 3), and/or the diagnostic use thereof, is enhanced by stimulation of the SPG and/or its related neuroanatomical structures, by using electrical stimulation, odorant presentation, and/or other means for stimulating the SPG or for modulating permeability of the BBB.

EXAMPLE 4

Therapeutics (Cholinesterase Inhibitors)

US patent application Publication 20020028834 to Villalobos et al., describes the use of cholinesterase inhibitors for enhancing memory in patients suffering from dementia and Alzheimer's disease. It is known that acetylcholinesterase inhibitors are effective in enhancing cholinergic activity and useful in improving the memory of Alzheimer's patients. By inhibiting acetylcholinesterase enzyme, these compounds increase the level of the neurotransmitter acetylcholine in the brain and thus enhance memory. Becker et al., cited hereinabove, report that behavioral changes following cholinesterase inhibition appear to coincide with predicted peak levels of acetylcholine in the brain. They also discuss the efficacy of three known acetylcholinesterase inhibitors, physostigmine, metrifonate, and tetrahydroaminoacridine.

In a preferred embodiment of the present invention, the therapeutic or prophylactic administration of such cholinesterase inhibitors is enhanced by stimulation of the SPG and/or its related neuroanatomical structures, by using electrical stimulation, odorant presentation, and/or other means for stimulating the SPG or for modulating permeability of the BBB.

EXAMPLE 5

Therapeutics (Direct Stimulation of Neural Regeneration)

There are continuous efforts to use a Nerve Growth Factor (NGF) as a stimulant of neural regeneration, thus potentially slowing degenerative processes, or even reversing neural damage. (NGF belongs to a large family of neural growth factors, including BDNF, IGF, GDNF and other active stimulants of neural regeneration. However, for the purpose of the present patent application, the term NGF shall be used to represent any such compound, or combinations thereof). Therefore, growth factor therapy for AD is considered a potentially curative approach of disease management However, such an approach still has to overcome the challenge of administering growth factor in adequate amounts, preferably over a continuous period of time, into the CNS. In the prior art, the BBB is generally considered impermeable to high molecular weight compounds, and thus systemic administration of growth factor, without using the techniques described herein, is not generally considered a treatment option for a patient with a functional BBB.

Because the BBB is generally considered in the prior art to be impermeable to high molecular weight compounds, invasive methods have been developed to enable NGF to reach a patient's brain. For example, a possible method for AD therapy, currently being tested in clinical trials, uses gene therapy techniques for the in-situ production of growth factors. This method involves brain surgery, where a patient's own cells are genetically modified to produce the NGF. The patient's cells, called "fibroblasts," are obtained from skin biopsies. The fibroblasts are genetically modified in vitro and are then implanted into either 5 or 10 locations in the patient's brain. The eventual goal of this research effort is to determine whether NGF produced by the cells implanted into the brain can prevent the death of some nerve cells that are affected in Alzheimer's disease, and enhance the function of some remaining brain cells.

In animal studies, fibroblasts genetically modified to produce NGF have been shown to prevent the death of certain nerve cells in the brain. This effectiveness has been shown in both the rat brain and the monkey brain. The genetically-modified cells prevent cell death after injury, and prevent cell atrophy that is a natural consequence of aging in primates.

A straightforward approach to circumventing the BBB would be to pierce the meninges and directly administer growth factors into the CNS. This technique, however, has several drawbacks. First, it puts the patient in a continuous risk of inflammatory brain processes. Second, direct infusion into the brain is usually very localized, and therefore its effectiveness is limited to the close vicinity of the administration tip, especially where the active molecule is of high molecular weight, making it less mobile. It is therefore clear that a relatively safe method of transiently opening the BBB to large molecular weight molecules, such as that described herein, could make nerve growth factors a compound of choice for the treatment of AD.

In a preferred embodiment of the present invention, the therapeutic or prophylactic administration of nerve growth factor is enhanced by stimulation of the SPG and/or its related neuroanatomical structures, by using electrical stimulation, odorant presentation, and/or other means for stimulating the SPG or for modulating permeability of the BBB.

US patent application Publication 20020040052 to Ito et al., describes a method for extending neurites of neurocytes without any side effects, and a method for preventing and/or treating neurodegeneration diseases using compositions having neurite extending effect. This invention is described as being necessary because the more direct method of administering NGF directly suffers from several limitations: "However, an NGF is a protein having a molecular weight of 13000 in the form of monomer and 26000 in the form of dimer, so that it cannot pass through the blood-brain barrier. Therefore, in order to treat disorders of central function, NGFs are required to be administrated intraventricularly. Moreover, it is difficult to prepare NGFs in large quantities. In these respects, there are many problems about the use of NGF itself. As a result, it is very difficult to use NGF itself clinically."

EXAMPLE 6

Therapeutics (Indirect Stimulation of Neural Regeneration)

One of the characteristics of Alzheimer's disease (AD) is loss of presynaptic markers such as synaptophysin. Synaptophysin decreases in neurodegenerative disorders along with a decline in neurotransmission. Synaptophysin: (i) is a synaptic vesicle-associated integral membrane protein (molecular weight about 38 kDa), (ii) acts as a specific marker for the presynaptic terminal, and (iii) is involved in neuronal transmission (Scheller, R. H., "Membrane Trafficking in the Presynaptic Nerve Terminal," Neuron 14: 893-897, 1995). A combination of neurotrophic factors is most effective in providing optimal trophic support for compromised neuron functions, including neurotransmission (Rathbone M. P. et al., "AIT-082 as a potential neuroprotective and regenerative agent in stroke and central nervous system injury," Exp. Opin. Invest. Drugs. 8:1255-12652, 1999). Multiple neurotrophic factors may synergistically regulate synaptophysin levels in a manner that can lead to increased neurotransmission and improved neuronal function.

Pharmaceutical agents that increase synaptophysin synthesis and/or secretion, decrease its metabolism, increase its release or improve its effectiveness may also be of benefit in reversing the course of neurological diseases including neurodegenerative diseases, such as Alzheimer's disease, and improve function in neurodevelopmental disorders, such as Down's syndrome. US patent application Publication 0020040032 to Glasky et al. describes a method of increasing the synthesis and/or secretion of synaptophysin, comprising administering to a patient with a neurological disease or a patient at risk of developing a neurological disease an effective quantity of a purine derivative or analogue, a tetrahydroindolone derivative or analogue, or a pyrimidine derivative or analogue. If the compound is a purine derivative, the purine moiety can be guanine or hypoxanthine.

Therefore, there exists a need for methods that can stimulate the synthesis and/or secretion of synaptophysin in patients with neurological diseases, including neurodegenerative diseases such as AD and neurodevelopmental disorders such as Down's syndrome, in order to preserve, restore or improve neuronal transmission capability in such patients. Preferably, these methods are combined with methods that enable active compounds to cross the BBB, making combined therapy more efficient These methods are suitable for use with compounds or pharmaceutical compositions that can stimulate nerve growth or regeneration in patients with neurological diseases, including neurodegenerative diseases such as AD and neurodevelopmental disorders such as Down's syndrome, thus reversing the course of the disease.

In a preferred embodiment of the present invention, the therapeutic or prophylactic administration of compounds affecting synaptophysin, and/or the diagnostic use thereof, is enhanced by stimulation of the SPG and/or its related neuroanatomical structures, by using electrical stimulation, odorant presentation, and/or other means for stimulating the SPG or for modulating permeability of the BBB.

US patent application Publication 20020019519 to Bingham et al. describes the use of KIAA0551 polypeptides and polynucleotides in the design of protocols for the treatment of various neurological disorders, among which is AD.

In a preferred embodiment of the present invention, the therapeutic or prophylactic administration of KIAA0551 polypeptides and polynucleotides, and/or the diagnostic use thereof, is enhanced by stimulation of the SPG its related neuroanatomical structures, by using electrical stimulation, odorant presentation, and/or other means for stimulating the SPG or for modulating permeability of the BBB.

EXAMPLE 7

Therapeutics (Antioxidants)

A number of diseases and disorders are thought to be caused by or to be associated with alterations in mitochondrial metabolism and/or inappropriate induction or suppression of mitochondria-related functions leading to apoptosis. These include, by way of example and not limitation, chronic neurodegenerative disorders such as Alzheimer's disease (AD) and Parkinson's disease (PD); auto-immune diseases; diabetes mellitus, including Type I and Type II; mitochondria associated diseases, including but not limited to congenital muscular dystrophy with mitochondrial structural abnormalities, fatal infantile myopathy with severe mtDNA depletion and benign "later-onset" myopathy with moderate reduction in mtDNA, MELAS (mitochondrial encephalopathy, lactic acidosis, and stroke) and MIDD (mitochondrial diabetes and deafness); MERFF (myoclonic epilepsy ragged red fiber syndrome); arthritis; NARP (Neuropathy; Ataxia; Retinitis Pigmentosa); MNGIE (Myopathy and external ophthalmoplegia; Neuropathy; Gastro-Intestinal; Encephalopathy), LHON (Leber's; Hereditary; Optic; Neuropathy), Kearns-Sayre disease; Pearson's Syndrome; PEO (Progressive External Ophthalmoplegia); Wolfram syndrome DIDMOAD (Diabetes Insipidus, Diabetes Mellitus, Optic Atrophy, Deafness); Leigh's Syndrome; dystonia; schizophrenia; and hyperproliferative disorders, such as cancer, tumors and psoriasis.

According to generally accepted theories of mitochondrial function, proper ETC respiratory activity requires maintenance of an electrochemical potential (ATm) in the inner mitochondrial membrane by a coupled chemiosmotic mechanism. Conditions that dissipate or collapse this membrane potential, including but not limited to failure at any step of the ETC, may thus prevent ATP biosynthesis and hinder or halt the production of a vital biochemical energy source. Altered or defective mitochondrial activity may also result in a catastrophic mitochondrial collapse that has been termed "mitochondrial permeability transition" (MPT). In addition, mitochondrial proteins such as cytochrome c and "apoptosis inducing factor" may dissociate or be released from mitochondria due to MPT (or the action of mitochondrial proteins such as Bax), and may induce proteases known as caspases and/or stimulate other events in apoptosis (Murphy, Drug Dev. Res. 46:18-25, 1999).

Defective mitochondrial activity may alternatively or additionally result in the generation of highly-reactive free radicals that have the potential of damaging cells and tissues. These free radicals may include reactive oxygen species (ROS) such as superoxide, peroxynitrite and hydroxyl radicals, and potentially other reactive species that may be toxic to cells. For example, oxygen free radical induced lipid peroxidation is a well established pathogenetic mechanism in central nervous system (CNS) injury such as that found in a number of degenerative diseases, and in ischemia (i.e., stroke). (Mitochondrial participation in the apoptotic cascade is believed to also be a key event in the pathogenesis of neuronal death.)

There are, moreover, at least two deleterious consequences of exposure to reactive free radicals arising from mitochondrial dysfunction that adversely impact the mitochondria themselves. First, free radical mediated damage may inactivate one or more of the myriad proteins of the ETC. Second, free radical mediated damage may result in catastrophic mitochondrial collapse that has been termed "transition permeability." According to generally accepted theories of mitochondrial function, proper ETC respiratory activity requires maintenance of an electrochemical potential in the inner mitochondrial membrane by a coupled chemiosmotic mechanism. Free radical oxidative activity may dissipate this membrane potential, thereby preventing ATP biosynthesis and/or triggering mitochondrial events in the apoptotic cascade.

There is evidence that defects in oxidative phosphorylation within the mitochondria are at least a partial cause of sporadic AD. The enzyme cytochrome c oxidase (COX), which makes up part of the mitochondrial electron transport chain (ETC), is present in normal amounts in AD patients; however, the catalytic activity of This enzyme in AD patients and in the brains of AD patients at autopsy has been found to be abnormally low. This suggests that the COX in AD patients is defective, leading to decreased catalytic activity that in some fashion causes or contributes to the symptoms that are characteristic of AD.

One hallmark pathology of AD is the death of selected neuronal populations in discrete regions of the brain. Cell death in AD is presumed to be apoptotic because signs of programmed cell death (PCD) are seen and indicators of active gliosis and necrosis are not found (Smale et al., Exp. Neurolog. 133:225-230, 1995; Cotman et al., Molec. Neurobiol. 10:19-45, 1995). The consequences of cell death in AD, neuronal and synaptic loss, are closely associated with the clinical diagnosis of AD and are highly correlated with the degree of dementia in AD (DeKosky et al., Ann. Neurology 2757-464, 1990).

Mitochondrial dysfunction is thought to be critical in the cascade of events leading to apoptosis in various cell types (Kroemer et al., FASEB J 9:1277-1287, 1995), and may be a cause of apoptotic cell death in neurons of the AD brain. Altered mitochondrial physiology may be among the earliest events in PCD (Zamzami et al., J. Exp. Med. 182:367-77, 1995; Zamzami et al., J. Exp. Med. 181:1661-72, 1995) and elevated reactive oxygen species (ROS) levels that result from such altered mitochondrial function may initiate the apoptotic cascade (Ausserer et al., Mol. Cell. Biol. 14:5032-42, 1994). In several cell types, including neurons, reduction in the mitochondrial membrane potential ($\delta\psi m$) precedes the nuclear DNA degradation that accompanies apoptosis. In cell-free systems, mitochondrial, but not nuclear, enriched fractions are capable of inducing nuclear apoptosis (Newmeyer et al., Cell 70:353-64, 1994). Perturbation of mitochondrial respiratory activity leading to altered cellular metabolic states, such as elevated intracellular ROS, may occur in mitochondria associated diseases and may further induce pathogenetic events via apoptotic mechanisms.

Oxidatively-stressed mitochondria may release a preformed soluble factor that can induce chromosomal condensation, an event preceding apoptosis (Marchetti et al., Cancer Res. 56:2033-38, 1996). In addition, members of the Bcl-2 family of anti-apoptosis gene products are located within the outer mitochondrial membrane (Monaghan et al., J. Histochem. Cytochem. 40:1819-25, 1992) and these proteins appear to protect membranes from oxidative stress (Korsmeyer et al, Biochim. Biophys. Acta 1271:63, 1995). Localization of Bcl-2 to this membrane appears to be indispensable for modulation of apoptosis (Nguyen et al., J. Biol. Chem. 269: 16521-24, 1994). Thus, changes in mitochondrial physiology may be important mediators of apoptosis. To the extent that apoptotic cell death is a prominent feature of neuronal loss in AD, mitochondrial dysfunction may be critical to the progression of this disease and may also be a contributing factor in other mitochondria associated diseases.

Focal defects in energy metabolism in the mitochondria, with accompanying increases in oxidative stress, may be associated with AD. It is well-established that energy metabolism is impaired in AD brain (Palmer et al., Brain Res. 645: 338-42, 1994; Pappolla et al., Am. J. Pathol. 140:621-28, 1992; Jeandel et al., Gerontol. 35:275, 1989; Balazs et al., Neurochem. Res. 19:1131-37, 1994; Mecocci et al., Ann. Neurol. 36:747-751, 1994; Gsell et al., J. Neurochem. 64:1216-23, 1995). For example, regionally specific deficits in energy metabolism in AD brains have been reported in a number of positron emission tomography studies (Kuhl, et al., J. Cereb. Blood Flow Metab. 7:S406, 1987; Grady, et al., J. Clin. Exp. Neuropsychol. 10:576-96, 1988; Haxby et al., Arch. Neurol. 4:753-60, 1990; Azari et al., J. Cereb. Blood Flow Metab. 13:438-47, 1993). Metabolic defects in the temporoparietal neocortex of AD patients apparently presage cognitive decline by several years. Skin fibroblasts from AD patients display decreased glucose utilization and increased oxidation of glucose, leading to the formation of glycosylation end products (Yan et al., Proc. Nat. Acad. Sci. U.S.A. 91:7787-91, 1994). Cortical tissue from postmortem AD brain shows decreased activity of the mitochondrial enzymes pyruvate dehydrogenase (Sheu et al., Ann Neurol. 17:444-49, 1985) and $\alpha$-ketoglutarate dehydrogenase (Mastrogiacomo et al., J. Neurochem. 6:2007-2014, 1994), which are both key enzymes in energy metabolism. Functional magnetic resonance spectroscopy studies have shown increased levels of inorganic phosphate relative to phosphocreatine in AD brain, suggesting an accumulation of precursors that arises from decreased ATP production by mitochondria (Pettegrew et al., Neurobiol. of Aging 15:117-32, 1994; Pettigrew et al., Neurobiol. of Aging 16:973-75, 1995). In addition, the levels of pyruvate, but not of glucose or lactate, are reported to be increased in the cerebrospinal fluid of AD patients, consistent with defects in cerebral mitochondrial electron transport chain (ETC) activity (Parnetti et al., Neurosci. Lett 199:231-33, 1995).

Signs of oxidative injury are prominent features of AD pathology and, as noted above, reactive oxygen species (ROS) are critical mediators of neuronal degeneration. Indeed, studies at autopsy show that markers of protein, DNA and lipid peroxidation are increased in AD brain (Paler et al., Brain Res. 645:338-42, 1994; Pappolla et al., Am J. Pathol. 140:621-28, 1992; Jeandel et al., Gerontol. 35:275-82, 1989; Balazs et al., Arch. Neurol. 4:864, 1994; Mecocci et al., Ann. Neurol. 36:747-751, 1994; Smith et al., Proc. Nat. Acad. Sci. U.S.A. 88:10540-10543, 1991). In hippocampal tissue from AD but not from controls, carbonyl formation indicative of protein oxidation is increased in neuronal cytoplasm, and nuclei of neurons and glia (Smith et al., Nature 382:120-21, 1996). Neurofibrillary tangles also appear to be prominent sites of protein oxidation (Schweers et al., Proc. Nat. Acad. Sci. U.S.A. 92:8463, 1995; Blass et al., Arch. Veurol. 4:864, 1990). Under stressed and non-stressed conditions incubation of cortical tissue from AD brains taken at autopsy demonstrate increased free radical production relative to non-AD controls. In addition, the activities of critical antioxidant enzymes, particularly catalase, are reduced in AD (Gsell et al., J. Neurochem. 64:1216-23, 1995), suggesting that the AD brain is vulnerable to increased ROS production. Thus, oxidative stress may contribute significantly to the pathology of mitochondria associated diseases such as AD, where mitochondrial dysfunction and/or elevated ROS may be present.

Increasing evidence points to the fundamental role of mitochondrial dysfunction in chronic neurodegenerative diseases (Beal, Biochim. Biophys. Acta 1366: 211-223, 1998), and recent studies implicate mitochondria for regulating the events that lead to necrotic and apoptotic cell death (Susin et al., Biochim. Biophys. Acta 1366: 151-168, 1998). Stressed (by, e.g., free radicals, high intracellular calcium, loss of ATP, among others) mitochondria may release pre-formed soluble factors that can initiate apoptosis through an interaction with apoptosomes (Marchetti et al., Cancer Res. 56:2033-38, 1996; Li et al., Cell 91: 479-89, 1997). Release of preformed soluble factors by stressed mitochondria, like cytochrome c, may occur as a consequence of a number of events. In any event, it is thought that the magnitude of stress (ROS, intracellular calcium levels, etc.) influences the changes in mitochondrial physiology that ultimately determine whether cell death occurs via a necrotic or apoptotic pathway. To the extent that apoptotic cell death is a prominent feature of degenerative diseases, mitochondrial dysfunction may be a critical factor in disease progression.

In a preferred embodiment of the present invention, the therapeutic or prophylactic administration of antioxidant compounds, and/or the diagnostic use thereof, is enhanced by stimulation of the SPG and/or its related neuroanatomical structures, by using electrical stimulation, odorant presentation, and/or other means for stimulating the SPG or for modulating permeability of the BBB.

EXAMPLE 8

Therapeutics ($\beta$-Amyloid Inhibitors)

U.S. patent application Publication 20020042420 to Briem et. al., describes a method to prepare compounds which may be capable of interfering (preferably in an inhibitory capacity) in the process of the formation of A$\beta$ or its release from cells, or of reducing the activity of A$\beta$ by inhibiting it. Their description has the further objective of preparing compounds which can be used effectively for the prevention or treatment of Alzheimer's disease.

US patent application Publication 20020025955 to Han et al., describes the potential use of lactams that inhibit the processing of amyloid precursor protein and, more specifically, inhibit the production of A$\beta$-peptide, thereby potentially acting to prevent the formation of neurological deposits of amyloid protein.

US patent application Publication 20020022621 to Chaturvedula et al., describes a series of arylacetamidoalanyl derivatives of benzodiazepinones, which are inhibitors of $\beta$-amyloid peptide production and may be useful in the treatment of Alzheimer's disease and other conditions characterized by aberrant extract cellular deposition of amyloid.

US patent application Publication 20010020097 to Audia et al., describes compounds which inhibit $\beta$-amyloid peptide release and/or its synthesis, and, accordingly, may have utility in treating Alzheimer's disease both prophylactically and therapeutically. Introduction of the compounds into the brain, for therapeutic purposes, or out of the brain, for diagnostic purposes, may require crossing the BBB.

U.S. Pat. No. 6,211,235 to Wu et al., describes compounds which inhibit $\beta$-amyloid peptide release and/or its synthesis, and, accordingly, may have utility in treating Alzheimer's disease. It also describes pharmaceutical compositions comprising a compound which may inhibit $\beta$-amyloid peptide release and/or its synthesis when introduced either directly or indirectly into the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 to Aebischer et al. Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the BBB. Alternatively, the delivery of hydrophilic drugs may be enhanced by intra-arterial infusion of hypertonic solutions which may transiently open the BBB to some extent.

However, without using the techniques described herein, no general method is known to controllably open the BBB for the efficient delivery of large-molecular weight pharmaceutical compounds, or compounds with high plasma protein binding.

In a preferred embodiment of the present invention, the therapeutic or prophylactic administration of the compounds described in this example (Example 8), and/or the diagnostic use thereof, is enhanced by stimulation of the SPG and/or its related neuroanatomical structures, by using electrical stimulation, odorant presentation, and/or other means for stimulating the SPG or for modulating permeability of the BBB.

EXAMPLE 9

Therapeutics ($\beta$-Amyloid Polymerization Inhibitors)

Bernd Bohrmann et al. reported (J Biol Chem, Vol. 274, Issue 23, 15990-15995, Jun. 4, 1999) that certain plasma proteins, at physiological concentrations, are potent inhibitors of $\beta$-amyloid peptide polymerization. These proteins are also present in cerebrospinal fluid, but at low concentrations having little or no effect on $\beta$-amyloid. Thirteen proteins representing more than 90% of the protein content in plasma and cerebrospinal fluid were studied. Quantitatively, albumin was the most important protein, representing 60% of the total amyloid inhibitory activity, followed by $\alpha$1-antitrypsin and immunoglobulins A and G. Albumin suppressed amyloid formation by binding to the oligomeric or polymeric beta-amyloid, blocking a further addition of peptide.

The results of Bohrmann et al. suggest that several endogenous proteins are negative regulators of amyloid formation. Plasma contains at least 300 times more amyloid inhibitory activity than cerebrospinal fluid. These findings may provide one explanation as to why $\beta$-amyloid deposits are not found in peripheral tissues but are only found in the central nervous system. Moreover, the data suggest that some drugs that display an affinity for albumin may enhance $\beta$-amyloid formation and promote the development of AD.

Increased penetration of plasma proteins into the CNS may, on the other hand, have an inhibitory effect on $\beta$-amyloid polymerization, consequently slowing, or reversing, AD progression.

In a preferred embodiment of the present invention, the permeability of the BBB is enhanced by stimulation of the SPG and/or its related neuroanatomical structures, by using electrical stimulation, odorant presentation, and/or other means for stimulating the SPG or for modulating permeability of the BBB, in order to permit $\beta$-amyloid polymerization inhibitors naturally occurring in the blood, particularly albumin, to pass from the blood into the CNS.

EXAMPLE 10

Therapeutics (Microglial Activation Modulators)

Acute and chronic brain injuries can activate resident microglia (resident macrophage-like cells found in the central nervous system) as well as recruit peripheral immune cells to injured brain regions that can exacerbate neuronal damage. Inflammatory processes can induce cell death by (a) the release of proteases and free radicals that induce lipid peroxidation, (b) direct cytotoxic effects or (c) the phagocytosis of sublethally-injured neurons. The attenuation of microglia and peripheral immune cell activation has been correlated with significant neuronal protection in pre-clinical studies of ischemia, traumatic brain injury, spinal cord injury and Alzheimer's disease. U.S. patent application Publication 20020022650 to Posmantur et al. describes methods of modulating or inhibiting microglia activation comprising the administration of a compound capable of inhibiting 5-LOX, FLAP, attenuating degradation of I$\kappa$B$\alpha$ or inhibiting nuclear translocation of the NF-$\kappa$B active complex for the treatment of various disorders associated with excessive production of inflammatory mediators in the brain, among which is Alzheimer's disease.

In a preferred embodiment of the present invention, the therapeutic or prophylactic administration of the compounds described in this example (Example 10), and/or the diagnostic use thereof, is enhanced by stimulation of the SPG and/or its related neuroanatomical structures, by using electrical stimulation, odorant presentation, and/or other means for stimulating the SPG or for modulating permeability of the BBB.

EXAMPLE 11

Therapeutics (NSAID)

Studies support an inverse relationship between anti-inflammatory medications used for treating patients with rheumatoid arthritis and an associated low prevalence of Alzheimer's disease (Rich, J. B. et al., Neurology 45:51-55, 1995). Controlled studies of twin pairs having Alzheimer's disease onset greater than 3 years apart provide additional support that prior treatment with anti-inflammatory medications serves a protective role in Alzheimer's disease (Breitner, J. C. S. et al., Neurology 44:227-232, 1994). Specifically, controlled double-blinded studies have found that the anti-inflammatory agent "indomethacin" administered orally has a therapeutic benefit for mild to moderately cognitively-impaired Alzheimer's disease patients, and treatment with indomethacin during early stages of the disease has a retarding effect on disease progression compared to the placebo treated control group. (Rogers, J. et al., Neurology 43:1609-1612, 1993). Alzheimer's patients with moderate cognitive impairment treated with indomethacin also exhibit a reduction in cognitive decline. However, patients treated with oral indomethacin developed drug related adverse effects that required their treatment to be discontinued and their removal from the study.

US patent application Publication 20010027309 to Elsberry describes a method for treating Alzheimer's disease, comprising delivering indomethacin or nonsteroidal anti-inflammatory drugs (NSAIDs) having cyclooxygenase inhibitor action directly to the hippocampus or the lateral ventricle through an implanted catheter.

It may also be advantageous to allow NSAID and other anti-inflammatory drugs into the CNS in combination with immunological (vaccine) treatment of AD. A vaccine, made by Elan Corporation (Dublin, Ireland) and known by its code name AN-1792, was tested in a clinical trial. In the trial, twelve volunteers were reported to have fallen seriously ill with brain inflammation, forcing the vaccine's manufacturer to halt the trial and raising doubts about the product's clinical potential. The AN-1792 vaccine had generated unusually intense enthusiasm among scientists and patient advocates during the past two years, as experiments in mice suggested it could halt the progression of Alzheimer's and perhaps even cure the deadly disease.

In general, NSAIDs are known to be very extensively protein bound (>99%). This characteristic makes the penetration of NSAID into the CNS very scarce, since they are usually bound to plasma proteins having molecular weights of around 70 kDa.

Therefore, allowing macromolecules into the CNS is expected to allow the introduction of anti-inflammatory drugs. These, on their own, or in conjunction with immunological or other therapeutic approaches, can serve as an effective treatment for AD.

In a preferred embodiment of the present invention, the therapeutic or prophylactic administration of NSAIDs and other anti-inflammatory agents, and/or the diagnostic use thereof, is enhanced by stimulation of the SPG and/or its related neuroanatomical structures, by using electrical stimulation, odorant presentation, and/or other means for stimulating the SPG or for modulating permeability of the BBB.

In another preferred embodiment of the present invention, the administration of a vaccine is enhanced by stimulation of the SPG and/or its related neuroanatomical structures, by using electrical stimulation, odorant presentation, and/or other means for stimulating the SPG or for modulating permeability of the BBB.

EXAMPLE 12

Therapeutics (Vaccine)

US patent application Publication 20020009445 to Du et al., discusses the use of an anti-A$\beta$ antibody for diagnosing and/or treating amyloid associated diseases, especially Alzheimer's disease. They indicate that naturally-occurring A$\beta$ antibodies exist in biologically relevant fluids, i.e., CSF and plasma, and that levels of these antibodies differ between normal age-matched healthy controls and AD patients. Based on these findings it was concluded and then supported by experiments that these antibodies can be used for diagnosis and treatment of amyloid associated diseases and especially of Alzheimer's disease. In the context of this application, the terms "anti-A$\beta$ antibodies" and "A$\beta$ antibodies" are used interchangeably to designate the antibody of their invention. An embodiment of their diagnostic method uses lumbar CSF samples, on which A$\beta$ antibody levels were determined utilizing an ELISA assay in which the A$\beta$ peptide was used as the capture ligand.

In a preferred embodiment of the present invention, the therapeutic or prophylactic administration of anti-A$\beta$ antibodies, and/or the diagnostic use thereof, is enhanced by stimulation of the SPG and/or its related neuroanatomical structures, by using electrical stimulation, odorant presentation, and/or other means for stimulating the SPG or for modulating permeability of the BBB.

EXAMPLE 13

Therapeutics (Other Approaches)

US patent application Publication 20020022593 to Yue describes a method of treating neurodegenerative dysfunctions and aging symptoms by administering a therapeutically-effective amount of relaxin (a polypeptide hormone, whose molecular weight is between 5,700 to 6,500 Da) to a patient. Neurodegenerative dysfunctions potentially amenable to treatment with relaxin include Alzheimer's, attention deficit disorder, Parkinson's, and others. The aforementioned method is based on the recognition that some of the symptoms associated with aging and/or neurodegenerative dysfunctions can be alleviated by relaxin, and may in fact be caused by a decrease of relaxin in the bloodstream. This lack of relaxin in the blood stream may be congenital or the result of another mechanism which suppresses the normal production or action of relaxin.

In a preferred embodiment of the present invention, the therapeutic or prophylactic administration of relaxin, and/or the diagnostic use thereof, is enhanced by stimulation of the SPG and/or its related neuroanatomical structures, by using electrical stimulation, odorant presentation, and/or other means for stimulating the SPG or for modulating permeability of the BBB.

US patent application Publication 20020019412 to Andersen et al., describes novel inhibitors of Protein Tyrosine Phosphatases (PTPase's) such as PTP1B, CD45, SHP-1, SHP-2, PTPα, LAR and HePTP or the like, for treatment of various systemic and CNS-related disorders, including Alzheimer's disease.

In a preferred embodiment of the present invention, the therapeutic or prophylactic administration of PTPase's, and/or the diagnostic use thereof, is enhanced by stimulation of the SPG and/or its related neuroanatomical structures, by using electrical stimulation, odorant presentation, and/or other means for stimulating the SPG or for modulating permeability of the BBB.

US patent application Publication 20020006959 to Henderson describes a method of potentially treating or preventing dementia of Alzheimer's type, or other loss of cognitive function caused by reduced neuronal metabolism, comprising administering an effective amount of medium chain triglycerides to a patient in need thereof.

In a preferred embodiment of the present invention, the therapeutic or prophylactic administration of medium chain triglycerides, and/or the diagnostic use thereof is enhanced by stimulation of the SPG and/or its related neuroanatomical structures, by using electrical stimulation, odorant presentation, and/or other means for stimulating the SPG or for modulating permeability of the BBB.

EXAMPLE 14

Diagnostics

Accurate diagnosis of AD during life is highly desirable. However, clinical evaluation is at best only about 80% accurate. Therefore, there exists a need to identify specific biochemical markers of AD. So far, analysis of blood or cerebrospinal fluid (CSF) has not yielded a biochemical marker of sufficient diagnostic value (Blass et al., 1998), although detectable differences are reported in the levels of certain proteins (Motter et al., Ann. Neurol. 38, 643-648, 1995).

Although recent reports of using positron-emission tomography (PET) (Reiman, E. M., et al., New Eng. J Med., 334: 752-758, 1996), determining the genotype of an individual's ApoE, or measuring the levels of β-amyloid protein in cerebral spinal fluid may be promising, diagnosis of AD is currently confirmed only upon autopsy to determine the presence of β-amyloid senile plaques.

Moreover, recent studies have shown that damage to CNS neurons due to Alzheimer's disease begins years before clinical symptoms are evident (Reiman, E. M. et al., New Eng. J Med., 334:752-758, 1996), suggesting that therapy could begin in the pre-symptomatic phase of the disease if a sensitive diagnostic test and targeted therapies were available. There exists a great need to determine the physiological mechanisms involved with the disease and for an accurate and easy to perform assay to evaluate the risk of developing Alzheimer's disease.

US patent application Publication 20020042121 to Riesner et al., describes a method for the diagnostic detection of diseases associated with protein depositions (pathological protein depositions) by measuring an association of substructures of the pathological protein depositions, structures forming pathological protein depositions, structures corresponding to pathological protein depositions and/or pathological protein depositions as a probe or a target.

US patent application Publication 20020028462 to Tanzi et al., describes a diagnostic method for AD based on genotyping the Alpha-2-Macroglobulin locus. A statistically-significant correlation was found between inheritance of particular alleles of the Alpha-2-Macroglobulin gene and the occurrence of AD. The diagnostic method involves the isolation of nucleic acid from an individual and subsequent genotyping by means such as sequencing or restriction fragment length polymorphism analysis. The invention also describes a means for genotype analysis through protein isotyping Alpha-2-Macroglobulin variant proteins. Finally, kits for nucleic acid analysis or protein analysis are described.

US patent application Publication 20020022242 to Small et al., describes a method for the diagnosis of AD in a patient by detecting the presence of BuChE with an altered glycosylation pattern in an appropriate body fluid sample. It has been established that on average approximately 93.6% of the BuChE in the CSF of AD patients binds to Concanavalin (Con A). All embodiments of this method are described as using either CSF or brain tissue as the sample, thereby adding a risk factor to the diagnostic procedure.

US patent application Publication 20020019519 to Bingham et al., describes the use of KIAA0551 polypeptides and polynucleotides in the design of protocols for the treatment of and also for diagnostics assays of AD.

US patent application Publication 20010044126 to Holtzman et al., describes a diagnostic method for identifying individuals at risk for developing Alzheimer's disease, which relies on elevated levels of the ratio of $A\beta_{40}/A\beta_{42}$ associated with lipoproteins in the cerebrospinal fluid of individuals at risk as compared to this ratio in the overall population. It is based on the assessment that the lipoprotein fraction of CSF in such individuals has such increased ratios.

US patent application Publication 20020019016 to Vanmechelen et al., describes a method for the differential diagnosis of an individual suffering from AD versus an individual suffering from another neurological disease (dementia with Lewy bodies, Parkinson's disease without dementia, multisystem atrophy and/or progressive supranuclear palsy), where phospho-tau is used as a neurological marker, the level of which is measured in a CSF sample.

US patent application Publication 20020009445 to Du et al., cited and summarized hereinabove, describes the use of an anti-Aβ antibody for diagnosing and/or treating amyloid associated diseases, especially Alzheimer's disease.

US patent application Publication 20020006627 to Reitz et al., describes a method for diagnosing Alzheimer's disease involving analysis of a test sample in such a way that β-amyloid$_{1-42}$ or Aβ3pE is completely or nearly completely (i.e., thoroughly) dissociated from binding proteins prior to the analysis of the levels of β-amyloid$_{1-42}$ or Aβ3pE.

US patent application Publication 20020002270 to Zinkowski et al., describes a preparation comprising Alzheimer's disease antigen (A68), as well as methods of obtaining this purified antigen (Ag), and methods using the purified Ag, for instance, for diagnosing Alzheimer's Disease, and also describes treatments of these Ags that enhance their reactivity with autoantibodies directed against A68. These treatments include treatment with hypericin, free fatty acids, and/or hydroxynonenal or other advanced glycation end products.

US patent application Publication 20010026916 to Ginsberg et al., describes a method of identifying senile plaques, neurofibrillary tangles and neuropil threads in brain tissue which comprises contacting brain tissue with a fluorescent dye capable of intercalating selectively into nucleic acids and detecting any fluorescence in the brain tissue indicative of senile plaques, neurofibrillary tangles and neuropil threads in the brain tissue.

U.S. Pat. No. 6,238,892 to Mercken et al., describes the use of a monoclonal antibody which forms an immunological complex with a phosphorylated epitope of an antigen belonging to human abnormally phosphorylated tau protein. The tau protein can be obtained from a brain homogenate, itself isolated from the cerebral cortex of a patient having Alzheimer's disease. Methods for in-vivo diagnosis of AD using the latter mAb, should preferably employ techniques that leaves the meninges intact Such methods are described in this patent as being yet undeveloped.

The '892 patent provides an overview of tau (complete references have been provided):

Tau is a microtubule-associated protein which is synthesized in the neurons (Kosik, K S. et al., Ann. Neurol. 26, 352-361, 1989) of several species, including humans, and which is abundantly present in the axonal compartment of these neurons (Binder, L. I. et al., J. Cell Biol., 101:1371-1378, 1985). Functionally the tau protein is involved in the polymerization of tubulin (Weingarten, M. D. et al., Proc. Natl. Acad. Sci. U.S.A. 72, 1868-1862, 1975) and presumably in reducing mictotubule instability (Bre, M. H. et al., Cell Motil. Cytoskeleton 15, 88-98, 1990).

Tau protein is also the major constituent of paired helical filaments (PHF), characteristic structures found as neurofibrillary tangles in tissue sections of the brain of Alzheimer patients (Greenberg, S. et al., Proc. Natl. Acad. Sci. U.S.A., 87, 5827-5831, 1990; Lee, V. M.-Y. et al., Science, 251, 675-678, 1991). The protein exists as a family of different isoforms of which 4 to 6 isoforms are found in normal adult brain but only 1 isoform is detected in fetal brain (Goedert, M. et al., Neuron 3, 519-526, 1989). The diversity of the isoforms is generated from a single gene by alternative mRNA splicing (Himmler, A., Mol. Cell. Biol., 9, 1389-1396, 1989). The most string feature of tau protein as predicted from molecular cloning is a stretch of 31 or 32 amino acids occurring in the carboxy-terminal part of the molecule that is repeated 3 or 4 times. Additional diversity is generated through 29 or 58 amino acid long insertions in the NH$_2$-terminal part of the molecules (Goedert, A et al., Neuron 3, 519-526, 1989).

Tau variants of 64 and 69 kDa, which are abnormally phosphorylated as revealed by the decrease in their molecular mass observed after alkaline phosphatase treatment, have been detected exclusively in brain areas showing neurofibrillary tangles and senile plaques (Flament, S. et al., A., J. Neurol. Sci. 92, 133-141, 1989; Flament, S. et al., Brain Res. 516, 15-19, 1990; and Flament, S. et al., Nature 346, 6279, 1990). The sites of phosphorylation by 4 different kinases have been mapped in the C-terminal microtubule-binding half of tau and it could be shown that the action of a calcium calmodulin-dependent kinase on bacterially expressed tau resulted in a phosphorylation of Ser(405) which induced a lower electrophoretical mobility (Steiner, B. et al., The EMBO Journal 9, 3539-3544, 1990).

Several antibodies are reported that show reactivity to human tau either because they are directed to nonspecific phosphorylated epitopes present on neurofilament and subsequently shown to cross-react with normal and abnormally phosphorylated tau (Nukina, N. et al., Proc. Natl. Acad. Sci. U.S.A. 84, 3415-3419, 1987; Ksiezak-Reding et al., Proc. Natl. Acad. Sci. U.S.A., 84, 3410-3414, 1987) or because they recognized specific epitopes on normal and abnormally phosphorylated tau.

The Alz50 monoclonal antibody (Wolozin, B. L. et al., Science 232, 648-650, 1986; Nukina et al., Neurosci. Lett 87, 240-246, 1988) recognizing a phosphate-independent epitope present on tau variants of bovine origin and of normal and abnormally phosphorylated tau from human origin (Ksiezak-Reding, H. et al., J. Biol. Chem., 263, 7943-7947, 1988, Flament, S. et al., Brain Res. 516, 15-19, 1990; and Flament, S. et al., Nature 346, 6279, 1990) belongs to the latter class of antibodies. The epitope recognized by this monoclonal is specifically expressed in the somatodendritic domain of degenerating cortical neurons during Alzheimer disease (Delacourte, A. et al., Acta Neuropathol. 80, 111-117, 1990).

The Alz50 epitope has recently been mapped to the NH$_2$-terminal part of the tau molecule (Ksiezak-Reding, H. et al., J. Neurosci. Res., 25, 412-419, 1990; Goedert, M. et al., Neurosci. Lett., 126, 149-154, 1991). Due to its cross-reactivity with normal tau, this antibody is only able to discriminate normal from abnormally phosphorylated tau by the use of Western blotting detection of brain homogenates or by ammonium sulfate-concentrated CSF, or also by using a sandwich immunoassay on brain homogenates (Ghanbari et al., J. Clin. Laboratory Anal. 4, 189-192, 1990; Wolozin, B. et al, Ann Neurol. 22, 521-526, 1987; European Patent Application Publication EP 0 444 856 to Ghanbari et al.). A CSF-based assay using antibodies directed against PHF was first described by Mehta et al., The Lancet, July, 35, 1985, but shows considerable overlap between Alzheimer CSF and CSF from controls. The epitope recognized by this antibody was identified as part of ubiquitin (Perry et al., J. Neurochem. 52, 1523-1528, 1989).

Other monoclonal antibodies have been developed to recognize tau protein. For instance, monoclonal antibody 5E2 was raised by immunization with human fetal heat-stable microtubule-associated proteins and recognizes an epitope spanning amino acids 156-175 which is present in normal and abnormally phosphorylated tau (Kosik, K. S. et al., Neuron., 1, 817-825, 1988).

Other antibodies such as tau 1 and several others were raised by immunization with bovine tau, bovine heat-stable microtubule-associated protein, or rat brain extracts (Binder, L. I. et al., J. Cell Biol. 101, 1371-1378, 1985; Kosik, K S. et al., Neuron., 1, 817-825, 1988), and most of the antibodies recognize the normal and the abnormally phosphorylated tau (Ksiezak-Reding, H. et al., J. Neurosci. Res., 25, 412-419, 1990).

An antibody named "423", raised against the core of PHF, reacted specifically with a 9.5 and 12-kDa fragment of the tau protein, localized in the repetitive elements of tau, but recognized neither normal human tau nor the abnormally phosphorylated tau in Alzheimer's brain (Wischik, C. H. et al., Proc. Natl. Acad. Sci. U.S.A., 85, 4884-4888, 1988). This antibody has been used to discriminate Alzheimer PHF pathology from normal controls in brain homogenates (Harrington, C. R. et al., J. Immunol. Methods 134, 261-271, 1990; PCT Publication WO089/03993 to Wischik et al.).

Thus far, none of all the antibodies described heretofore has had an absolute specificity for the abnormally phosphorylated tau either by immunohistology, Western blotting, or ELISA. Quantitative measurements of normal and abnormally phosphorylated tau have until now only been able to detect tau in brain homogenates, in brain extracts containing PHF, or in concentrated CSF samples after Western blotting (Ghanbari H. A et al., J. Clin. Laboratory Anal. 4, 189-192, 1990; Harrington C. R. et al., J. Immunol. Methods 134, 261-271, 1990, Wisniewski, H. M. et al., *Biological Markers of Alzheimer's Disease*, Boller, Katzman, Rascol, Signoret & Christian eds., 23-29, 1989; Wolozin, B. et al., Ann. Neurol. 22, 521-526, 1987).

US patent application Publication 20010018191 to Mercken et al., describes monoclonal antibodies which are described as specifically able to detect only abnormally-phosphorylated tau present in brain tissue sections, in brain extracts, or in body fluids such as cerebrospinal fluid. It is required that a method for bypassing the BBB be employed in order to introduce the monoclonal antibodies into the CNS.

US patent application Publication 20010014670 to Balin et al., describes a method of treating Alzheimer's disease in a mammal comprising administering to the mammal an anti-microbial agent having anti-Chlamydia pneumoniae activity. The description also relates to a method of diagnosing Alzheimer's disease in a mammal comprising measuring the serum anti-Chlamydia pneumoniae antibody titer in a patient suspected of having Alzheimer's disease. It is required that a method for bypassing the BBB be employed in order to communicate the therapeutic compounds, antibodies, into the CNS, or to be able to evaluate presence of diagnostic agents (e.g. C. Pneumoniae) in a minimally invasive method.

U.S. Pat. No. 6,287,793 to Schenk et al., describes methods for the identification of key diagnostic antibodies, antigens, diagnostic kits and methods for diagnosis for AD, where the diagnostic procedure uses a biological fluid from a subject—most preferred are plasma and CSF sample.

Inducing changes in BBB permeability, as provided by preferred embodiments of the present invention, is useful for detecting acetylcholinesterase in human patients. Loss of acetylcholinesterase in humans is associated with brain disorders, such as dementia and epilepsy, muscle disorders, and disorders of the digestive system. The methods of some embodiments of the present invention are particularly useful for detecting acetylcholinesterase in the brain of a patient suspected of suffering from a dementia, such as Alzheimer's disease, thereby allowing the diagnosis, estimating the severity of, and monitoring the progression of the dementia. Certain brain disorders and dementia, including Alzheimer's disease, are known to be accompanied by a decrease in acetylcholinesterase concentration in the brain. Thus, monitoring the concentration of acetylcholinesterase in the brain of a patient suspected of suffering from a brain disorder or dementia typically allows diagnosis of the disorder or dementia, monitoring its progression, and/or estimating its severity. Advantageously, this diagnosis and monitoring is simply performed, for example, by stimulating the SPG using techniques described herein, and, simultaneously or shortly thereafter, extracting a blood sample using standard lab techniques. Since the increase in BBB permeability allows the acetylcholinesterase to pass therethrough, it is quickly in the systemic bloodstream and detectable in the blood sample. It is to be understood that other compounds of diagnostic value can be extracted using essentially the same technique.

The methods of some embodiments of the present invention can be used to provide a brain image that shows the distribution and relative concentrations of acetylcholinesterase (or other compounds of diagnostic value) in a patient's brain, thereby allowing diagnosis, estimating the severity of, and analysis of the progression of a disorder or dementia in a patient. The methods of some embodiments of the invention can therefore be used to diagnosis, estimate the severity, and monitor the progression of any dementia, known or to be discovered, that is accompanied by a detectable change in concentration of acetylcholinesterase or other compounds of diagnostic value in the brain. In a preferred embodiment, a molecule such as an antibody which is attracted to acetylcholinesterase is injected, swallowed, or otherwise introduced systemically, and its passage into the CNS is facilitated by techniques described herein for increasing permeability of the BBB. Imaging techniques which are able to detect the introduced molecule are then utilized to determine the locations or quantities of acetylcholinesterase or other diagnostic compounds to which the molecule is attached.

Some of the diagnostic techniques mentioned above indicate to the inventors that there is a need for performing diagnostic tests on certain bio-chemical characteristics of the CSF by using a simple blood test Other diagnostic techniques mentioned above indicate to the inventors that there is a need for increasing the permeability of the BBB using techniques described herein in order to facilitate the passage of diagnostic molecules into the CNS, where the molecules can be detected, such as by imaging. Diagnostic procedures, which are on one hand highly accurate and on the other minimally invasive, typically substantially improve the management of AD, when applied in accordance with a preferred embodiment of the present invention. In a preferred embodiment of the present invention, the diagnostic techniques described in this example (Example 14) are enhanced and/or enabled by stimulation of the SPG and/or its related neuroanatomical structures, by using electrical stimulation, odorant presentation, and/or other means for stimulating the SPG or for modulating permeability of the BBB.

Techniques described in the present patent application may be practiced in combination with methods and apparatus described in one or more of the following patent applications, which are assigned to the assignee of the present patent application and are incorporated herein by reference:

PCT Publication WO 01/85094, filed May 7, 2001, entitled, "Method and apparatus for stimulating the sphenopalatine ganglion to modify properties of the BBB and cerebral blood flow"

U.S. Provisional Patent Application 60/364,451, filed Mar. 15, 2002, entitled, "Applications of stimulating the sphenopalatine ganglion (SPG)"

U.S. Provisional Patent Application 60/368,657, filed Mar. 28, 2002, entitled, "SPG Stimulation"

U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head"

U.S. Provisional Patent Application 60/388,931, filed Jun. 14, 2002, entitled "Methods and systems for management of Alzheimer's disease"

U.S. Provisional Patent Application 60/400,167, filed Jul. 31, 2002, entitled, "Delivering compounds to the brain by modifying properties of the BBB and cerebral circulation"

a U.S. Provisional Patent Application, filed Nov. 14, 2002, entitled, "Surgical tools and techniques for sphenopalatine ganglion stimulation"

a U.S. Provisional Patent Application, filed Nov. 14, 2002, entitled, "Stimulation circuitry and control of electronic medical device"

a U.S. Patent Application, filed Nov. 14, 2002, entitled, "SPG stimulation for treating eye pathologies"

a U.S. Patent Application, filed Nov. 14, 2002, entitled, "Administration of anti-inflammatory drugs into the CNS"

a U.S. Provisional Patent Application, filed Nov. 14, 2002, entitled, "Stimulation for treating ear pathologies"

a U.S. Provisional Patent Application, filed Feb. 20, 2003, entitled, "Stimulation for treating autoimmune-related disorders of the CNS"

a U.S. Provisional Patent Application to Gross et al., filed Apr. 8, 2003, entitled, "Treating abnormal conditions of the mind and body by modifying properties of the blood-brain barrier and cephalic blood flow"

a PCT patent application to Shalev, filed Apr. 25, 2003, entitled, "Methods and apparatus for modifying properties of the BBB and cerebral circulation by using the neuroexcitatory and/or neuroinhibitory effects of odorants on nerves in the head"

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, elements which are shown in a figure to be housed within one integral unit may, for some applications, be disposed in a plurality of distinct units. Similarly, apparatus for communication and power transmission which are shown to be coupled in a wireless fashion may be, alternatively, coupled in a wired fashion, and apparatus for communication and power transmission which are shown to be coupled in a wired fashion may be, alternatively, coupled in a wireless fashion.

The invention claimed is:

1. A method comprising:
   directly applying an electrical signal to a sphenopalatine ganglion (SPG) of a subject suffering from Alzheimer's disease (AD); and
   treating the AD by configuring the electrical signal to stimulate the SPG.

2. The method according to claim 1, wherein configuring comprises configuring the electrical signal so as to cause an increase in cerebral blood flow (CBF) of the subject, so as to treat the AD.

3. The method according to claim 1, wherein configuring the electrical signal comprises configuring the electrical signal to induce parasympathetic activation of the SPG.

4. The method according to claim 1, wherein applying the electrical signal comprises applying long-term stimulation to the SPG.

5. The method according to claim 4, wherein applying the long-term stimulation comprises applying long-term intermittent stimulation to the SPG.

6. The method according to claim 1, wherein directly applying the electrical signal comprises implanting an electrical stimulator in a nasal cavity of the subject, and applying the electrical signal using the stimulator.

7. The method according to claim 1, wherein directly applying the electrical signal comprises directly attaching an electrical stimulator to the SPG, and applying the electrical signal using the stimulator.

* * * * *